US009499494B2

(12) United States Patent
Kirsch et al.

(10) Patent No.: US 9,499,494 B2
(45) Date of Patent: Nov. 22, 2016

(54) PYRIMIDINE-2,4,6-TRIONES FOR USE IN THE TREATMENT OF AMYOTROPHIC LATERAL SCLEROSIS

(71) Applicant: Northwestern University, Evanston, IL (US)

(72) Inventors: Donald R. Kirsch, Bedford, MA (US); Radhia Benmohamed, Tewksbury, MA (US); Anthony C. Arvanites, Medford, MA (US); Richard I. Morimoto, Evanston, IL (US); Guoyao Xia, Chicago, IL (US); Richard B. Silverman, Winnetka, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/046,333

(22) Filed: Oct. 4, 2013

(65) Prior Publication Data

US 2015/0203456 A1 Jul. 23, 2015

Related U.S. Application Data

(63) Continuation of application No. 13/318,429, filed as application No. PCT/US2010/033714 on May 5, 2010, now abandoned.

(60) Provisional application No. 61/175,783, filed on May 5, 2009.

(51) Int. Cl.
*C07D 239/62* (2006.01)
*C07D 403/06* (2006.01)
*C07D 403/14* (2006.01)
*C07D 409/06* (2006.01)
*C07D 413/06* (2006.01)

(52) U.S. Cl.
CPC ........... *C07D 239/62* (2013.01); *C07D 403/06* (2013.01); *C07D 403/14* (2013.01); *C07D 409/06* (2013.01); *C07D 413/06* (2013.01)

(58) Field of Classification Search
CPC ................. C07C 239/62; C07C 403/06; C07C 403/14; C07C 409/06; C07C 413/06
USPC .......................................... 544/299, 300, 303
See application file for complete search history.

(56) References Cited

U.S. PATENT DOCUMENTS

| 4,826,983 A * | 5/1989 | Neilan ................. C08K 5/3477 524/101 |
| 4,925,938 A | 5/1990 | Neilan et al. |
| 2005/0107414 A1 | 5/2005 | Noe |
| 2007/0135437 A1 | 6/2007 | Benjamin et al. |
| 2009/0163545 A1 | 6/2009 | Goldfarb |
| 2011/0237907 A1* | 9/2011 | Kirsch ................... A61B 5/412 600/301 |
| 2012/0196883 A1* | 8/2012 | Surmeier, Jr. ........ C07D 239/62 514/270 |

FOREIGN PATENT DOCUMENTS

| JP | 2002301872 | 10/2002 |
| JP | 2002301872 A * | 10/2002 |
| WO | 03030841 | 4/2003 |
| WO | 2005077918 | 8/2005 |
| WO | 2006089221 | 8/2006 |
| WO | 2007150011 | 12/2007 |
| WO | WO 2010059241 A2 * | 5/2010 ............. A61B 5/412 |

OTHER PUBLICATIONS

Goodman & Gilman's, Manual of Pharmacology and Therapeutics 336-348 (L.L. Bruton et al., eds., 2008).*
CAS Reg No. 500282-45-1 (Mar. 23, 2003).*
International Preliminary Report on Patentability, PCT/US2010/033714 (Nov. 9, 2011).
Kienzle, F. et al., 176. Die synthese von 6, 7-Dihydro-2H-pyrimido [6,1-a] isochinolin-4(3H)-onen und analogen Verbindungen und deren Wirkung als Bluplattchenaggregationshemmer, Helvetica Chimica Acta, vol. 69, 1671-1680 (1986).
Palwinder, S. et al., A Practical Approach for Spiro- and 5-Monoalkylated Barbuturic Acids, J. Heterocyclic Chem., vol. 43, 607-612 (2006).
Supplementary European Search Report for EP 10772761, 7 pages (Oct. 12, 2012).
Takanaka, K. et al., Enantioselective Synthesis of C2-Symmetric Spirobilactams via PD-Catalyzed Intramolecular Double N-Arylation, Organic Letters., vol. 11, No. 7, 2009, pp. 1483-1486.
Volonterio, Alessandro and Matteo Zanda, Multicomponent One-Pot Sequential Synthesis of 1,3,5,- and 1,3,5,5 Substituted Barbiturates, Journal of Organic Chemistry, vol. 72, No. 19, 2008, pp. 7486-7497.
Gan, Kim-Hong et al., Direct palladium/carboxylic acid-catalyzed C-allylation of cyclic 1 ,3-diones with allyic alcohols in water, Tetrahedron vol. 64, No. 7, 2008, pp. 1204-1212.
Forgacs, Esther and Tibor Cserhati., Solvent Strength and Selectivity on a Porous Graphitized Carbon Column Separated by a Spectral Mapping Technique Using Barbiturates as Solutes, Analytical Sciences, vol. 17, No. 2, 2001, pp. 307-312.
Cowden, William and Noel W. Jacobsen, Pyrimidine N-Oxides. IV* the N,N'-Dihydroxy of Phenobarbital and Veronal, Australian Journal of Chemistry, vol. 35, No. 4, 1982, pp. 795-797.
International Search Report and Written Opinion, PCT/US10/33714, mailed on Feb. 9, 2011, published on Nov. 11, 2010 as WO2010/129665.

* cited by examiner

*Primary Examiner* — Alexander R Pagano
(74) *Attorney, Agent, or Firm* — Reinhart Boerner Van Deuren s.c.

(57) ABSTRACT

The present invention relates to the identification of inventive pyrimidine-2,4,6-triones (PYT compounds) and pharmaceutical compositions thereof for treating subjects with amyotrophic lateral sclerosis (ALS) and other neurodegenerative diseases. The invention also provides methods of preparing the inventive PYT compounds.

23 Claims, 11 Drawing Sheets

PYRIMIDINE-2,4,6-TRIONES FOR USE IN THE TREATMENT OF AMYOTROPHIC LATERAL SCLEROSIS

CROSS-REFERENCE TO RELATED APPLICATIONS

This application claims priority to U.S. provisional application Ser. No. 61/175,783, filed May 5, 2009, the entirety of which is hereby incorporated herein by reference.

GOVERNMENT SUPPORT

This invention was made with government support under Grant No. R43 NS057849 awarded by the National Institutes of Health. The government has certain rights in this invention.

BACKGROUND OF THE INVENTION

Amyotrophic lateral sclerosis (ALS) is a fatal neurodegenerative disorder caused by motor neuron death (Rowland et al., *N. Engl. J. Med.,* 2001, 334, 1688-1700) and characterized in part by the presence of abnormal aggregates of insoluble protein in selectively vulnerable populations of neurons and glia. ALS, an orphan disease, is estimated to afflict about 87,000 people worldwide, but its prevalence would be much higher were it not for the fact that ALS patients survive for only 3 to 5 years on average after diagnosis. Approximately 10% of ALS cases are familial, with the rest of the cases being sporadic (Rowland et al., *N. Engl. J. Med.,* 2001, 334, 1688-1700). Approximately 20% of the cases of familial ALS are caused by inherited mutations in the protein Cu/Zn superoxide dismutase (SOD1) (Rosen et al., *Nature,* 1993, 362, 59-62). Rodent models in mutant SOD1 are often used as a disease model because of its phenotypic and pathologic resemblance to sporadic and familial human ALS (Dal Canto et al., *Brain Res.,* 1995, 676, 25-40; Wong, et al. *Neuron,* 1995, 14, 1105-1116; Bruijin et al., *Science,* 1998, 281, 1851-1854; Bruijn et al., *Neuron,* 1997, 18, 327-338; Wang et al., *Hum. Mol. Genet.,* 2003, 12, 2753-2764; Wang et al., *Neurobiol. Dis.,* 2002, 10, 128-138; Jonsson et al., *Brain,* 2004, 127, 73-88).

The causes of sporadic ALS remain unknown, and the clinical courses are variable, suggesting that multiple factors are involved. Different hypotheses have been proposed, such as glutamate-mediated excitotoxicity, impaired mitochondrial function, oxidative stress, and aberrant protein aggregation (Dib et al., *Drugs,* 2003, 63, 289-310; Strong et al., *Pharmacology & Therapeutics,* 2003, 98, 379-414; Kunst et al., *Am. J. Hum. Genet.,* 2004, 75, 933-947; Bruijn et al., *Annu. Rev. Neurosci,* 2004, 27, 723-749; Dibernardo et al., *Biochimica et Biophysica Acta,* 2006, 1762, 1139-1149). Riluzole, which decreases glutamate excitotoxicity, is the only FDA approved ALS drug (Jimonet et al., *J. Med. Chem.,* 1999, 42, 2828-2843.). However, it can only extend median survival life for 2 to 3 months, suggesting mechanisms other than glutamate-mediated excitotoxicity should be considered during ALS drug development (Miller et al., *ALS and Other Motor Neuron Disorders,* 2003, 4, 191-206; Taylor et al., *Neurology* 2006, 67, 20-27).

SUMMARY OF THE INVENTION

The present invention encompasses the recognition that there exists a need for new compounds and methods for treating patients with amyotrophic lateral sclerosis (ALS) or other neurodegenerative diseases characterized by the presence of aberrant protein aggregates.

The present invention relates to the identification of pyrimidine-2,4,6-trione compounds (PYT compounds) and pharmaceutical compositions thereof to treat neurodegenerative diseases. Among other things, the present invention provides methods of treating amyotrophic lateral sclerosis (ALS) with provided PYT compounds. Without wishing to be bound by any particular theory, provided PYT compounds may be useful in the treatment of ALS or other neurodegenerative diseases where abnormal protein aggregation has been implicated, as they may prevent the aggregation of protein in a cell or limit the toxicity of such aggregates.

In one aspect, the invention provides PYT compounds of the formula:

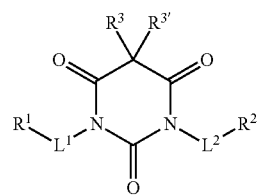

wherein $R^1$, $R^2$, $R^3$, $R^{3'}$, $L^1$, and $L^2$ are as defined herein, or pharmaceutically acceptable salts thereof. In some embodiments, such PYT compounds, or pharmaceutically acceptable salts thereof, are used in the treatment of neurodegenerative diseases.

In some embodiments, the present invention provides methods of treating a subject suffering from or susceptible to a neurodegenerative disease, disorder or condition (e.g., ALS) with provided PYT compounds. In certain embodiments, the subject is an adult human.

In some embodiments, the present invention provides methods of inhibiting or reversing abnormal protein aggregation (e.g., SOD1 protein aggregates) using provided PYT compounds. Inhibiting or reversing abnormal protein aggregation may occur in vivo (e.g., in a subject as described herein) or in vitro (e.g., in a cell).

In some embodiments, the invention provides methods of protecting cells from the cytotoxic effects of aggregated protein (e.g., SOD1) using provided PYT compounds. Protection of cells may occur in vivo (e.g., in a subject as described herein) or in vitro (e.g., in a cell).

In some embodiments, the invention provides methods of modulating proteasome activity in vivo (e.g., in a subject as described herein) or in vitro (e.g., in a cell) using provided PYT compounds. In certain embodiments, the cells are mammalian cells.

All publications and patent documents cited in this application are incorporated herein by reference in their entirety

DEFINITIONS

Aliphatic: The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

Alkylene: The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

Alkenylene: The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, a genetically-engineered animal, and/or a clone.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). In some embodiments, use of the term "about" in reference to dosages means±5 mg/kg/day.

Aryl: The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

Characteristic portion: As used herein, the phrase a "characteristic portion" of a protein or polypeptide is one that contains a continuous stretch of amino acids, or a collection of continuous stretches of amino acids, that together are characteristic of a protein or polypeptide. Each such continuous stretch generally will contain at least two amino acids. Furthermore, those of ordinary skill in the art will appreciate that typically at least 5, 10, 15, 20 or more amino acids are required to be characteristic of a protein. In general, a characteristic portion is one that, in addition to the sequence identity specified above, shares at least one functional characteristic with the relevant intact protein.

Characteristic sequence: A "characteristic sequence" is a sequence that is found in all members of a family of polypeptides or nucleic acids, and therefore can be used by those of ordinary skill in the art to define members of the family.

Heteroaryl: The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

Heteroatom: The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

Heterocycle: As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Intraperitoneal: The phrases "intraperitoneal administration" and "administered intraperitoncaly" as used herein have their art-understood meaning referring to administration of a compound or composition into the peritoneum of a subject.

In vitro: As used herein, the term "in vitro" refers to events that occur in an artificial environment, e.g., in a test tube or reaction vessel, in cell culture, etc., rather than within an organism (e.g., animal, plant, and/or microbe).

In vivo: As used herein, the term "in vivo" refers to events that occur within an organism (e.g., animal, plant, and/or microbe).

Lower alkyl: The term "lower alkyl" refers to a $C_{1-4}$ straight or branched alkyl group. Exemplary lower alkyl groups are methyl, ethyl, propyl, isopropyl, butyl, isobutyl, and tert-butyl.

Lower haloalkyl: The term "lower haloalkyl" refers to a $C_{1-4}$ straight or branched alkyl group that is substituted with one or more halogen atoms.

Optionally substituted: As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$ C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$ NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^{\bullet}$, -(haloR$^{\bullet}$), —(CH$_2$)$_{0-2}$OH, —(CH$_2$)$_{0-2}$OR$^{\bullet}$, —(CH$_2$)$_{0-2}$CH(OR$^{\bullet}$)$_2$; —O(haloR$^{\bullet}$), —CN, —N$_3$, —(CH$_2$)$_{0-2}$C(O)R$^{\bullet}$, —(CH$_2$)$_{0-2}$C(O)OH, —(CH$_2$)$_{0-2}$C(O)OR$^{\bullet}$, —(CH$_2$)$_{0-2}$SR$^{\bullet}$, —(CH$_2$)$_{0-2}$SH, —(CH$_2$)$_{0-2}$NH$_2$, —(CH$_2$)$_{0-2}$NHR$^{\bullet}$, —(CH$_2$)$_{0-2}$NR$^{\bullet}$$_2$, —NO$_2$, —SiR$^{\bullet}$$_3$, —OSiR$^{\bullet}$$_3$, —C(O)SR$^{\bullet}$, —(C$_{1-4}$ straight or branched alkylene)C(O)OR$^{\bullet}$, or —SSR$^{\bullet}$ wherein each R$^{\bullet}$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*2))$_{2-3}$S—, wherein each independent occurrence of R* is selected from hydrogen, C$_1$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^{\bullet}$, -(haloR$^{\bullet}$), —OH, —OR$^{\bullet}$, —O(haloR$^{\bullet}$), —CN, —C(O)OH, —C(O)OR$^{\bullet}$, —NH$_2$, —NHR—, —NR$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Partially unsaturated: As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Patient: As used herein, the term "patient", "subject", or "test subject" refers to any organism to which provided PYT compound is administered in accordance with the present invention e.g., for experimental, diagnostic, prophylactic, and/or therapeutic purposes. Typical subjects include animals (e.g., mammals such as mice, rats, rabbits, non-human primates, and humans; insects; worms; etc.). In some embodiments, a subject may be suffering from, and/or susceptible to a disease, disorder, and/or condition (e.g., a neurodegenerative disease, a disease, disorder or condition associated with protein aggregation, ALS, etc.).

Pharmaceutically acceptable: The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Prodrug: A general, a "prodrug", as that term is used herein and as is understood in the art, is an entity that, when administered to an organism, is metabolized in the body to deliver a therapeutic agent of interest. Various forms of "prodrugs" are known in the art. For examples of such prodrug derivatives, see:

a) *Design of Prodrugs*, edited by H. Bundgaard, (Elsevier, 1985) and *Methods in Enzymology*, 42:309-396, edited by K. Widder, et al. (Academic Press, 1985);

b) A Textbook of Drug Design and Development, edited by Krogsgaard-Larsen;

c) Bundgaard, Chapter 5 "Design and Application of Prodrugs", by H. Bundgaard, p. 113-191 (1991);

d) Bundgaard, *Advanced Drug Delivery Reviews*, 8:1-38 (1992);

e) Bundgaard, et al., *Journal of Pharmaceutical Sciences*, 77:285 (1988); and f) Kakeya, et al., *Chem. Pharm. Bull.*, 32:692 (1984).

The methods and structures described herein relating to the provided compounds also apply to pharmaceutically acceptable salts thereof.

Protecting group: The term "protecting group," as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4 nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, 0-nitrobenzyl, p-nitrobenzyl, p-halobenzyl, 2,6-dichlorobenzyl, p-cyanobenzyl), and 2- and 4-picolyl.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

Protein: As used herein, the term "protein" refers to a polypeptide (i.e., a string of at least two amino acids linked to one another by peptide bonds). In some embodiments, proteins include only naturally-occurring amino acids. In some embodiments, proteins include one or more non-naturally-occurring amino acids (e.g., moieties that form one or more peptide bonds with adjacent amino acids). In some embodiments, one or more residues in a protein chain contains a non-amino-acid moiety (e.g., a glycan, etc). In some embodiments, a protein includes more than one polypeptide chain, for example linked by one or more disulfide bonds or associated by other means. In some embodiments, proteins contain L-amino acids, D-amino acids, or both; in some embodiments, proteins contain one or more amino acid modifications or analogs known in the art. Useful modifications include, e.g., terminal acetylation, amidation, methylation, etc. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

PYT compound: The term "PYT compound", as used herein, refers to a compound of formula I:

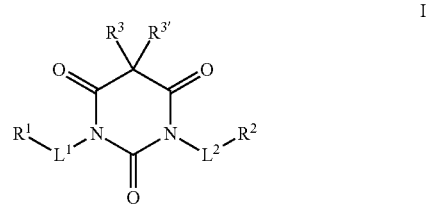

or a pharmaceutically acceptable salt thereof, wherein:

$L^1$ is a valence bond or a bivalent optionally substituted saturated, partially saturated, or unsaturated hydrocarbon chain, wherein 1-3 methylene units of $L^1$ are optionally and independently replaced by —NR—, —N(R)C(O)—, —C(O)N(R)—, —N(R)SO$_2$—, —SO$_2$N(R)—, —O—, —C(O)—, —OC(O)—, —C(O)O—, —S—, —S(O)— or —SO$_2$—; or wherein $L^1$ is —(C(R)$_2$)$_n$— and wherein n is 1 to 6, inclusive;

$R^1$ is —R, —OR, —CN, —NO$_2$, —SR, —S(O)R, —SO$_2$R, —C(O)R, —CO$_2$R, —C(O)N(R)$_2$, —NRC(O)R, —NRC(O)N(R)$_2$, —NRSO$_2$R, —N(R)$_2$, or wherein $R^1$ is phenyl, a 5-6 membered monocyclic saturated, partially saturated, or aromatic ring having 1-4 heteroatoms independently selected from nitrogen, oxygen, or sulfur, or an 8-10 membered saturated, partially saturated, or aromatic bicyclic ring having 0-4 heteroatoms independently selected from nitrogen, oxygen, or sulfur, and wherein $R^1$ is optionally substituted with p occurrences of $R^a$, wherein p is 0 to 5, inclusive;

each $R^a$ is independently selected from the group consisting of —R, —OR, —CN, —NO$_2$, —SR, —S(O)R, —SO$_2$R, —C(O)R, —CO$_2$R, —C(O)N(R)$_2$, —NRC(O)R, —NRC(O)N(R)$_2$, —NRSO$_2$R, —N(R)$_2$, or wherein $R^a$ is an optionally substituted 5-6 membered monocyclic saturated, partially saturated, or aromatic ring having 1-4 heteroatoms independently selected from nitrogen, oxygen, or sulfur, or an optionally substituted 8-10 membered saturated, partially saturated, or aromatic bicyclic ring having 0-4 heteroatoms independently selected from nitrogen, oxygen, or sulfur;

each R is independently hydrogen, halogen, optionally substituted $C_{1-6}$ aliphatic, optionally substituted phenyl, optionally substituted benzyl, or two R on the same nitrogen are taken together to form a 5-6 membered saturated, partially saturated, or aromatic ring having 1-3 heteroatoms independently selected from nitrogen, oxygen, and sulfur;

$L^2$ is a valence bond or a bivalent optionally substituted saturated, partially saturated, or unsaturated hydrocarbon chain, wherein 1-3 methylene units of $L^2$ are optionally and independently replaced by —NR—, —N(R)C(O)—, —C(O)N(R)—, —N(R)SO$_2$—, —SO$_2$N(R)—, —O—, —C(O)—, —OC(O)—, —C(O)O—, —S—, —S(O)— or —SO$_2$—; or wherein $L^2$ is —(C(R)$_2$)$_m$— and wherein m is 1 to 6, inclusive;

$R^2$ is —R, —OR, —CN, —NO$_2$, —SR, —S(O)R, —SO$_2$R, —C(O)R, —CO$_2$R, —C(O)N(R)$_2$, —NRC(O)R, —NRC(O)N(R)$_2$, —NRSO$_2$R, —N(R)$_2$, or wherein $R^2$ is phenyl, a 5-6 membered monocyclic saturated, partially saturated, or aromatic ring having 1-4 heteroatoms independently selected from nitrogen, oxygen, or sulfur, or an 8-10 membered saturated, partially saturated, or aromatic bicyclic ring having 0-4 heteroatoms independently selected from nitrogen, oxygen, or sulfur, and wherein $R^2$ is optionally substituted with q occurrences of $R^b$, wherein q is 0 to 5, inclusive;

each $R^b$ is independently selected from the group consisting of —R, —OR, —CN, —NO$_2$, —SR, —S(O)R, —SO$_2$R, —C(O)R, —CO$_2$R, —C(O)N(R)$_2$, —NRC(O)R, —NRC(O)N(R)$_2$, —NRSO$_2$R, —N(R)$_2$, or wherein $R^b$ is an optionally substituted 5-6 membered monocyclic saturated, partially saturated, or aromatic ring having 1-4 heteroatoms independently selected from nitrogen, oxygen, or sulfur, or an optionally substituted 8-10 membered saturated, partially saturated, or aromatic bicyclic ring having 0-4 heteroatoms independently selected from nitrogen, oxygen, or sulfur;

$R^3$ and $R^{3'}$ are independently hydrogen, halogen, or optionally substituted $C_{1-6}$ aliphatic, or $R^3$ and $R^{3'}$ are taken together to form a $C_1$ alkenylene optionally substituted with one or two $R^c$ groups;

each $R^c$ is independently —R, —OR, —CN, —NO$_2$, —SR, —S(O)R, —SO$_2$R, —C(O)R, —CO$_2$R, —C(O)N(R)$_2$, —NRC(O)R, —NRC(O)N(R)$_2$, —NRSO$_2$R, —N(R)$_2$, or wherein $R^c$ is phenyl, a 5-6 membered monocyclic saturated, partially saturated, or aromatic ring having 1-4 heteroatoms independently selected from nitrogen, oxygen, or sulfur, or an 8-10 membered saturated, partially saturated, or aromatic bicyclic ring having 0-4 heteroatoms independently selected from nitrogen, oxygen, or sulfur, and wherein $R^c$ is optionally substituted with t occurrences of $R^d$, wherein t is 0 to 5, inclusive; and each $R^d$ is independently —R, —OR, —CN, —C(R)$_3$, —NO$_2$, —SR, —S(O)R, —SO$_2$R, —C(O)R, —CO$_2$R, —C(O)N(R)$_2$, —NRC(O)R, —NRC(O)N(R)$_2$, —NRSO$_2$R, or —N(R)$_2$.

In some embodiments, the term "PYT compound" may encompass prodrugs and/or esters of compounds of formula I. As discussed herein, PYT compounds may be provided in salt form. In particular, in some embodiments, a PYT compound is provided as a pharmaceutically acceptable salt of a compound of formula I.

The provided PYT compounds may exist in particular geometric or stereoisomeric forms. The present invention contemplates all such PYT compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. In certain embodiments, the present invention relates to a PYT compound represented by any of the structures outlined herein, wherein the compound is a single stereoisomer.

The terms acid or base addition salt also comprise the hydrates and the solvent addition forms which the compounds are able to form. Examples of such forms are, e.g., hydrates, alcoholates and the like.

Contemplated equivalents of the compounds described above include compounds which otherwise correspond thereto, and which have the same general properties thereof, wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants, which are in themselves known, but are not mentioned here.

Stereochemically isomeric forms: The phrase "stereochemically isomeric forms," as used herein, refers to different compounds made up of the same atoms bonded by the same sequence of bonds but having different three-dimensional structures which are not interchangeable. In some embodiments of the invention, chemical compositions may be provided as pure preparations of individual stereochemically isomeric forms of a compound; in some embodiments, chemical compositions may be provided that are or include mixtures of two or more stereochemically isomeric forms of the compound. In certain embodiments, such mixtures contain equal amounts of different stereochemically isomeric forms; in certain embodiments, such mixtures contain different amounts of at least two different stereochemically isomeric forms. In some embodiments, a chemical composition may contain all diastereomers and/or enantiomers of the compound. In some embodiments, a chemical composition may contain less than all diastereomers and/or enantiomers of a compound. Unless otherwise indicated, the present invention encompasses all stereochemically isomeric forms of relevant compounds, whether in pure form or in admixture with one another. If a particular enantiomer of a compound of the present invention is desired, it may be prepared, for example, by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, diastereomeric salts are formed with an appropriate optically-active acid, and resolved, for example, by fractional crystallization.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Suffering from: An individual who is "suffering from" a disease, disorder, and/or condition has been diagnosed with and/or displays one or more symptoms of a disease, disorder, and/or condition.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Tautomeric forms: The phrase "tautomeric forms," as used herein, is used to describe different isomeric forms of organic compounds that are capable of facile interconversion. Tautomers may be characterized by the formal migration of a hydrogen atom or proton, accompanied by a switch of a single bond and adjacent double bond. In some embodiments, tautomers may result from prototropic tautomerism (i.e., the relocation of a proton). In some embodiments, tautomers may result from valence tautomerism (i.e., the rapid reorganization of bonding electrons). All such tautomeric forms are intended to be included within the scope of the present invention. In some embodiments, tautomeric forms of a compound exist in mobile equilibrium with each other, so that attempts to prepare the separate substances results in the formation of a mixture. In some embodiments, tautomeric forms of a compound are separable and isolatable compounds. In some embodiments of the invention, chemical compositions may be provided that are or include pure preparations of a single tautomeric form of a compound. In some embodiments of the invention, chemical compositions may be provided as mixtures of two or more tautomeric forms of a compound. In certain embodiments, such mixtures contain equal amounts of different tautomeric forms; in certain embodiments, such mixtures contain different amounts of at least two different tautomeric forms of a compound. In some embodiments of the invention, chemical compositions may contain all tautomeric forms of a compound. In some embodiments of the invention, chemical compositions may contain less than all tautomeric forms of a compound. In some embodiments of the invention, chemical compositions may contain one or more tautomeric forms of a compound in amounts that vary over time as a result of interconversion. Unless otherwise indicated, the present invention encompasses all tautomeric forms of relevant compounds, whether in pure form or in admixture with one another.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Systemic: The phrases "systemic administration," "administered systemically," "peripheral administration," and "administered peripherally" as used herein have their art-understood meaning referring to administration of a compound or composition such that it enters the recipient's system.

Unsaturated: The term "unsaturated," as used herein, means that a moiety has one or more units of unsaturation.

For purposes of this invention, the chemical elements are identified in accordance with the Periodic Table of the Elements, CAS version, *Handbook of Chemistry and Physics*, 67th Ed., 1986-87, inside cover.

The methods and structures described herein relating to compounds and compositions of the invention also apply to the pharmaceutically acceptable acid or base addition salts and all stereoisomeric forms of these compounds and compositions.

DETAILED DESCRIPTION OF THE INVENTION

Pyrimidine-2,4,6-trione ("PYT" compounds)

Figure 1:
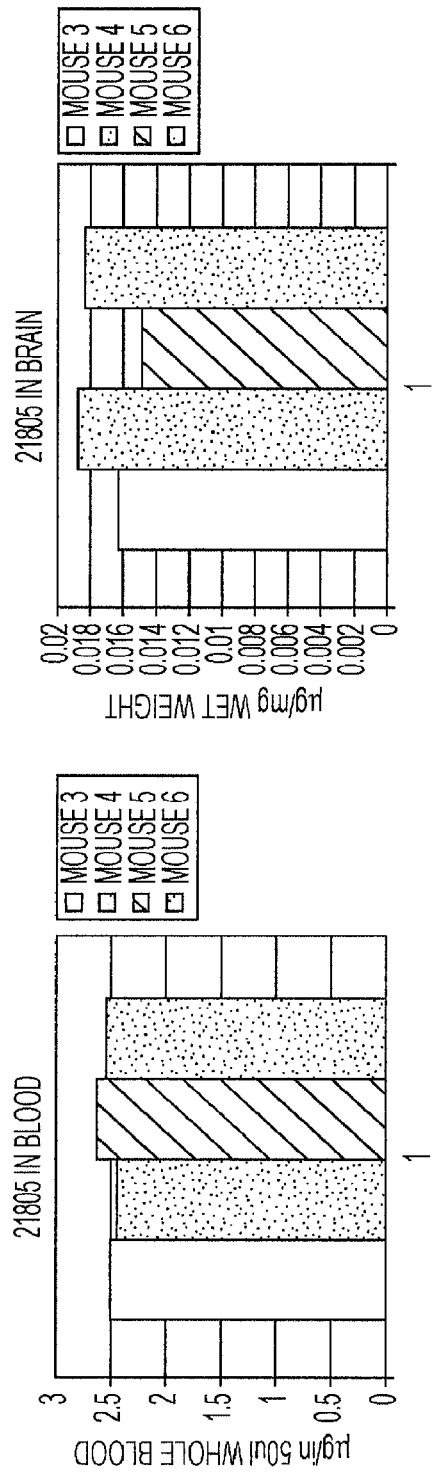
FIG. 1. Blood-brain barrier penetration of CMB-021805.

The present invention provides novel pyrimidine-2,4,6-trione compounds (herein referred to as PYT compounds), compositions, and methods for treating patients suffering from or susceptible to amyotrophic lateral sclerosis (ALS) or other neurodegenerative diseases. Without wishing to be bound by any particular theory or mechanism of action, provided PYT compounds and compositions thereof are useful in inhibiting or reversing abnormal protein aggregation or reducing the toxicity of protein aggregation (e.g., SOD1). In certain embodiments, provided PYT compounds and compositions thereof are useful in modulating proteosome function. The present invention provides methods for treating a subject suffering from or susceptible to ALS or other neurodegenerative disease including the step of administering to the subject a therapeutically effective amount of a provided PYT compound or composition thereof. In certain embodiments, the subject is a mammal (e.g., a human).

In one aspect, the present invention provides a compound or composition comprising a compound of Formula I:

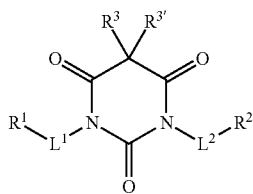

I or a pharmaceutically acceptable salt thereof, wherein:

$L^1$ is a valence bond or a bivalent optionally substituted saturated, partially saturated, or unsaturated hydrocarbon chain, wherein 1-3 methylene units of $L^1$ are optionally and independently replaced by —NR—, —N(R)C(O)—, —C(O)N(R)—, —N(R)SO$_2$—, —SO$_2$N(R)—, —O—, —C(O)—, —OC(O)—, —C(O)O—, —S—, —S(O)— or —SO$_2$—; or wherein $L^1$ is —(C(R)$_2$)$_n$— and wherein n is 1 to 6, inclusive;

$R^1$ is —R, —OR, —CN, —NO$_2$, —SR, —S(O)R, —SO$_2$R, —C(O)R, —CO$_2$R, —C(O)N(R)$_2$, —NRC(O)R, —NRC(O)N(R)$_2$, —NRSO$_2$R, —N(R)$_2$, or wherein $R^1$ is phenyl, a 5-6 membered monocyclic saturated, partially saturated, or aromatic ring having 1-4 heteroatoms independently selected from nitrogen, oxygen, or sulfur, or an 8-10 membered saturated, partially saturated, or aromatic bicyclic ring having 0-4 heteroatoms independently selected from nitrogen, oxygen, or sulfur, and wherein $R^1$ is optionally substituted with p occurrences of $R^a$, wherein p is 0 to 5, inclusive;

each $R^a$ is independently selected from the group consisting of —R, —OR, —CN, —NO$_2$, —SR, —S(O)R, —SO$_2$R, —C(O)R, —CO$_2$R, —C(O)N(R)$_2$, —NRC(O)R, —NRC(O)N(R)$_2$, —NRSO$_2$R, —N(R)$_2$, or wherein $R^a$ is an optionally substituted 5-6 membered monocyclic saturated, partially saturated, or aromatic ring having 1-4 heteroatoms independently selected from nitrogen, oxygen, or sulfur, or an optionally substituted 8-10 membered saturated, partially saturated, or aromatic bicyclic ring having 0-4 heteroatoms independently selected from nitrogen, oxygen, or sulfur;

each R is independently hydrogen, halogen, optionally substituted $C_{1-6}$ aliphatic, optionally substituted phenyl, optionally substituted benzyl, or two R on the same nitrogen are taken together to form a 5-6 membered saturated, partially saturated, or aromatic ring having 1-3 heteroatoms independently selected from nitrogen, oxygen, and sulfur;

$L^2$ is a valence bond or a bivalent optionally substituted saturated, partially saturated, or unsaturated hydrocarbon chain, wherein 1-3 methylene units of $L^2$ are optionally and independently replaced by —NR—, —N(R)C(O)—, —C(O)N(R)—, —N(R)SO$_2$—, —SO$_2$N(R)—, —O—, —C(O)—, —OC(O)—, —C(O)O—, —S—, —S(O)— or —SO$_2$—; or wherein $L^2$ is —(C(R)$_2$)$_m$— and wherein m is 1 to 6, inclusive;

$R^2$ is —R, —OR, —CN, —NO$_2$, —SR, —S(O)R, —SO$_2$R, —C(O)R, —CO$_2$R, —C(O)N(R)$_2$, —NRC(O)R, —NRC(O)N(R)$_2$, —NRSO$_2$R, —N(R)$_2$, or wherein $R^2$ is phenyl, a 5-6 membered monocyclic saturated, partially saturated, or aromatic ring having 1-4 heteroatoms independently selected from nitrogen, oxygen, or sulfur, or an 8-10 membered saturated, partially saturated, or aromatic bicyclic ring having 0-4 heteroatoms independently selected from nitrogen, oxygen, or sulfur, and wherein $R^2$ is optionally substituted with q occurrences of $R^b$, wherein q is 0 to 5, inclusive;

each $R^b$ is independently selected from the group consisting of —R, —OR, —CN, —NO$_2$, —SR, —S(O)R, —SO$_2$R, —C(O)R, —CO$_2$R, —C(O)N(R)$_2$, —NRC(O)R, —NRC(O)N(R)$_2$, —NRSO$_2$R, —N(R)$_2$, or wherein $R^b$ is an optionally substituted 5-6 membered monocyclic saturated, partially saturated, or aromatic ring having 1-4 heteroatoms independently selected from nitrogen, oxygen, or sulfur, or an optionally substituted 8-10 membered saturated, partially saturated, or aromatic bicyclic ring having 0-4 heteroatoms independently selected from nitrogen, oxygen, or sulfur;

$R^3$ and $R^{3'}$ are independently hydrogen, halogen, or optionally substituted $C_{1-6}$ aliphatic, or $R^3$ and $R^{3'}$ are taken together to form a $C_1$ alkenylene optionally substituted with one or two $R^c$ groups;

each $R^c$ is independently —R, —OR, —CN, —NO$_2$, —SR, —S(O)R, —SO$_2$R, —C(O)R, —CO$_2$R, —C(O)N(R)$_2$, —NRC(O)R, —NRC(O)N(R)$_2$, —NRSO$_2$R, —N(R)$_2$, or wherein $R^c$ is phenyl, a 5-6 membered monocyclic saturated, partially saturated, or aromatic ring having 1-4 heteroatoms independently selected from nitrogen, oxygen, or sulfur, or an 8-10 membered saturated, partially saturated, or aromatic bicyclic ring having 0-4 heteroatoms independently selected from nitrogen, oxygen, or sulfur, and wherein $R^c$ is optionally substituted with t occurrences of $R^d$, wherein t is 0 to 5, inclusive; and each $R^d$ is independently —R, —OR, —CN, —C(R)$_3$, —NO$_2$, —SR, —S(O)R, —SO$_2$R, —C(O)R, —CO$_2$R, —C(O)N(R)$_2$, —NRC(O)R, —NRC(O)N(R)$_2$, —NRSO$_2$R, or —N(R)$_2$.

In some embodiments, $L^1$ is a valence bond. In some embodiments, $L^1$ is a bivalent optionally substituted saturated, partially saturated, or unsaturated hydrocarbon chain, wherein 1-3 methylene units of $L^1$ are optionally and independently replaced by —NR—, —N(R)C(O)—, —C(O)N(R)—, —N(R)SO$_2$—, —SO$_2$N(R)—, —O—, —C(O)—, —OC(O)—, —C(O)O—, —S—, —S(O)— or —SO$_2$—. In some embodiments, $L^1$ is a bivalent optionally substituted saturated hydrocarbon chain, wherein 1 methylene unit of $L^1$ is replaced by —NR—, —N(R)C(O)—, —C(O)N(R)—, —N(R)SO$_2$—, —SO$_2$N(R)—, —O—, —C(O)—, —OC (O)—, —C(O)O—, —S—, —S(O)— or —SO₂—. In some embodiments, L¹ is a bivalent optionally substituted saturated hydrocarbon chain, wherein 1 methylene unit of L is replaced by —NR—, —O—, or —S—. In some embodiments, L¹ is a bivalent optionally substituted saturated hydrocarbon chain, wherein 1 methylene unit of L¹ is replaced by —O—. In certain embodiments, L¹ is —(C(R)₂)$_n$— and n is 1, 2, 3, 4, 5, or 6. In some embodiments, L¹ is —(C(R)₂)$_n$— wherein at least one R is independently halogen. In some embodiments, L¹ is —(C(R)₂)$_n$— wherein at least one R is independently fluorine. In some embodiments, L¹ is —(C(R)₂)$_n$— wherein at least two R are independently fluorine. In certain embodiments, L¹ is —(C(R)₂)₂—. In some embodiments, L¹ is —(C(R)₂)₂— wherein at least two R are independently fluorine. In certain embodiments, L¹ is —(C(R)₂)₃— wherein one methylene unit of L is replaced by —O—.

In some embodiments, R¹ is —R, hydrogen, halogen, —OR, —CN, —NO₂, —SR, —S(O)R, —SO₂R, —C(O)R, —CO₂R, —C(O)N(R)₂, —NRC(O)R, —NRC(O)N(R)₂, —NRSO₂R, or —N(R)₂. In some embodiments, R¹ is unsubstituted phenyl. In some embodiments, R¹ is phenyl substituted with p occurrences of R$^a$. In certain embodiments, p is 0, 1, 2, 3, 4, or 5.

In some embodiments, R¹ is of the formula:

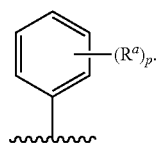

In some embodiments, R¹ is of one of the formulae:

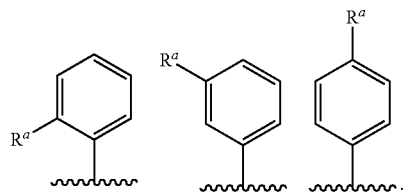

In some embodiments, R¹ is of one of the formulae:

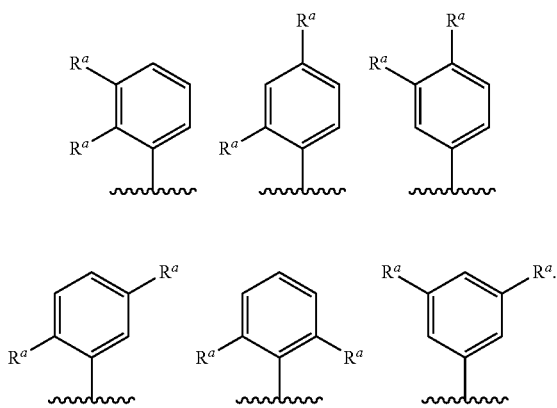

In some embodiments, R¹ is of one of the formulae:

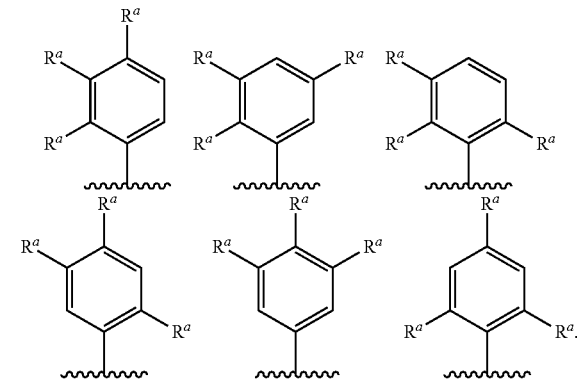

In some embodiments, R¹ is of one of the formulae:

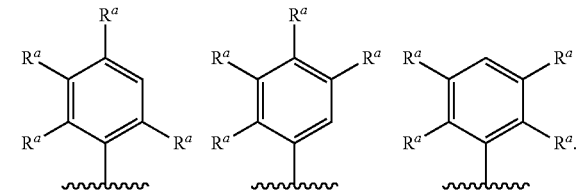

In some embodiments, R¹ is of the formula:

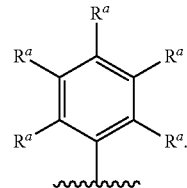

In some embodiments, R¹ is an optionally substituted 5-membered monocyclic saturated, partially saturated, or aromatic ring having 1-4 heteroatoms independently selected from nitrogen, oxygen, or sulfur. In some embodiments, R¹ is an unsubstituted 5-membered aromatic ring having 1-3 heteroatoms independently selected from nitrogen, oxygen, or sulfur. In some embodiments, R¹ is a substituted 5-membered aromatic ring having 1-3 heteroatoms independently selected from nitrogen, oxygen, or sulfur. In some embodiments, R¹ is optionally substituted thiophene. In some embodiments, R¹ is optionally substituted furan.

In some embodiments, R¹ is an unsubstituted 6-membered monocyclic saturated, partially saturated, or aromatic ring having 1-4 heteroatoms independently selected from nitrogen, oxygen, or sulfur. In some embodiments, R¹ is a substituted 6-membered monocyclic saturated, partially saturated, or aromatic ring having 1-4 heteroatoms independently selected from nitrogen, oxygen, or sulfur. In certain embodiments, R¹ is a substituted 6-membered monocyclic saturated ring having 1-3 heteroatoms independently selected from nitrogen, oxygen, or sulfur. In certain embodiments, R¹ is a substituted 6-membered monocyclic partially saturated ring having 1-3 heteroatoms independently selected from nitrogen, oxygen, or sulfur. In some embodiments, R¹ is a substituted 6-membered monocyclic aromatic ring containing one nitrogen.

In some embodiments, $R^1$ is an unsubstituted 8 membered saturated, partially saturated, or aromatic bicyclic ring having 0-4 heteroatoms independently selected from nitrogen, oxygen, or sulfur. In some embodiments, $R^1$ is a substituted 8 membered saturated, partially saturated, or aromatic bicyclic ring having 0-4 heteroatoms independently selected from nitrogen, oxygen, or sulfur. In some embodiments, $R^1$ is an optionally substituted 8 membered saturated bicyclic ring having 1-3 heteroatoms independently selected from nitrogen, oxygen, or sulfur. In some embodiments, $R^1$ is an optionally substituted 8 membered partially saturated bicyclic ring having 1-3 heteroatoms independently selected from nitrogen, oxygen, or sulfur.

In some embodiments, $R^1$ is an unsubstituted 9 membered saturated, partially saturated, or aromatic bicyclic ring having 0-4 heteroatoms independently selected from nitrogen, oxygen, or sulfur. In some embodiments, $R^1$ is a substituted 9 membered saturated, partially saturated, or aromatic bicyclic ring having 0-4 heteroatoms independently selected from nitrogen, oxygen, or sulfur. In some embodiments, $R^1$ is an optionally substituted 9 membered saturated bicyclic ring having 1-3 heteroatoms independently selected from nitrogen, oxygen, or sulfur. In some embodiments, $R^1$ is an optionally substituted 9 membered partially saturated bicyclic ring having 1-3 heteroatoms independently selected from nitrogen, oxygen, or sulfur. In some embodiments, $R^1$ is an optionally substituted 9 membered aromatic bicyclic ring having 1-3 heteroatoms independently selected from nitrogen, oxygen, or sulfur.

In some embodiments, $R^1$ is an unsubstituted 10 membered saturated, partially saturated, or aromatic bicyclic ring having 0-4 heteroatoms independently selected from nitrogen, oxygen, or sulfur. In some embodiments, $R^1$ is a substituted 10 membered saturated, partially saturated, or aromatic bicyclic ring having 0-4 heteroatoms independently selected from nitrogen, oxygen, or sulfur. In some embodiments, $R^1$ is an optionally substituted 10 membered saturated bicyclic ring having 1-3 heteroatoms independently selected from nitrogen, oxygen, or sulfur. In some embodiments, $R^1$ is an optionally substituted 10 membered partially saturated bicyclic ring having 1-3 heteroatoms independently selected from nitrogen, oxygen, or sulfur. In some embodiments, $R^1$ is an optionally substituted 10 membered aromatic bicyclic ring having 1-3 heteroatoms independently selected from nitrogen, oxygen, or sulfur.

In some embodiments, $R^1$ is not a nitrogen-containing heteroaryl or heterocyclic moiety. In some embodiments, $R^1$ is not an amide or lactam. In certain embodiments, $R^1$ is not a pyrrolidine, piperidine, or morpholine. In certain embodiments, $R^1$ is not pyridine or indole.

In some embodiments, $R^1$ is R. In some embodiments, $R^1$ is hydrogen, methyl, ethyl, propyl, butyl, pentyl, or hexyl. In some embodiments, $R^1$ is cyclopropyl, cyclobutyl, cyclopentyl, or cyclohexyl. In certain embodiments, $R^1$ is $C_{1-6}$ optionally substituted aliphatic.

In some embodiments, $R^a$ is independently selected from the group consisting of —R, halogen, —OR, —CN, —NO$_2$, —SR, —S(O)R, —SO$_2$R, —C(O)R, —CO$_2$R, —C(O)N(R)$_2$, —NRC(O)R, —NRC(O)N(R)$_2$, —NRSO$_2$R, —N(R)$_2$. In some embodiments, $R^a$ is an optionally substituted 5-6 membered monocyclic saturated, partially saturated, or aromatic ring having 1-4 heteroatoms independently selected from nitrogen, oxygen, or sulfur. In some embodiments, $R^a$ is an optionally substituted 8-10 membered saturated, partially saturated, or aromatic bicyclic ring having 0-4 heteroatoms independently selected from nitrogen, oxygen, or sulfur.

In some embodiments, at least one $R^a$ is independently halogen. In some embodiments, at least two $R^a$ are independently halogen. In some embodiments, at least one $R^a$ is independently fluorine. In some embodiments, at least two $R^a$ are independently fluorine. In some embodiments, at least one $R^a$ is independently —OR. In some embodiments, least two $R^a$ are independently —OR. In some embodiments, at least one $R^a$ is independently —OMe. In some embodiments, at least two $R^a$ are independently —OMe. In some embodiments, $R^a$ is substituted phenyl. In some embodiments, $R^a$ is unsubstituted phenyl. In some embodiments, $R^a$ is substituted naphthyl. In some embodiments, $R^a$ is unsubstituted naphthyl.

In some embodiments, $L^2$ is a valence bond. In some embodiments, $L^2$ is a bivalent optionally substituted saturated, partially saturated, or unsaturated hydrocarbon chain, wherein 1-3 methylene units of $L^2$ are optionally and independently replaced by —NR—, —N(R)C(O)—, —C(O)N(R)—, —N(R)SO$_2$—, —SO$_2$N(R)—, —O—, —C(O)—, —OC(O)—, —C(O)O—, —S—, —S(O)— or —SO$_2$—. In some embodiments, $L^2$ is a bivalent optionally substituted saturated hydrocarbon chain, wherein 1 methylene unit of $L^2$ is replaced by —NR—, —N(R)C(O)—, —C(O)N(R)—, —N(R)SO$_2$—, —SO$_2$N(R)—, —O—, —C(O)—, —OC(O)—, —C(O)O—, —S—, —S(O)— or —SO$_2$—. In some embodiments, $L^2$ is a bivalent optionally substituted saturated hydrocarbon chain, wherein 1 methylene unit of $L^2$ is replaced by —NR—, —O—, or —S—. In some embodiments, $L^2$ is a bivalent optionally substituted saturated hydrocarbon chain, wherein 1 methylene unit of $L^2$ is replaced by —O—. In certain embodiments, $L^2$ is —(C(R)$_2$)$_n$— and n is 1, 2, 3, 4, 5, or 6. In some embodiments, $L^2$ is —(C(R)$_2$)$_n$— wherein at least one R is independently halogen. In some embodiments, $L^2$ is —(C(R)$_2$)$_n$— wherein at least one R is independently fluorine. In some embodiments, $L^2$ is —(C(R)$_2$)$_n$— wherein at least two R are independently fluorine. In certain embodiments, $L^2$ is —(C(R)$_2$)$_2$—. In some embodiments, $L^2$ is —(C(R)$_2$)$_2$— wherein at least two R are independently fluorine. In certain embodiments, $L^2$ is —(C(R)$_2$)$_3$— wherein one methylene unit of $L^2$ is replaced by —O—.

In certain embodiments, $L^1$ and $L^2$ are the same. In certain embodiments, $L^1$ and $L^2$ are not the same.

In some embodiments, $R^2$ is —R, hydrogen, halogen, —OR, —CN, —NO$_2$, —SR, —S(O)R, —SO$_2$R, —C(O)R, —CO$_2$R, —C(O)N(R)$_2$, —NRC(O)R, —NRC(O)N(R)$_2$, —NRSO$_2$R, or —N(R)$_2$. In some embodiments, $R^2$ is unsubstituted phenyl. In some embodiments, $R^2$ is phenyl substituted with q occurrences of $R^b$. In certain embodiments, q is 0, 1, 2, 3, 4, or 5.

In some embodiments, $R^2$ is of the formula:

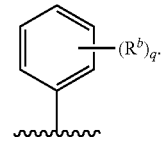

In some embodiments, R² is of one of the formulae:

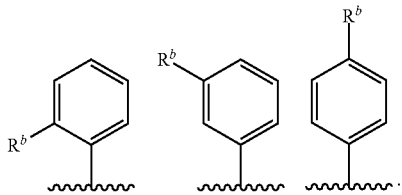

In some embodiments, R² is of one of the formulae:

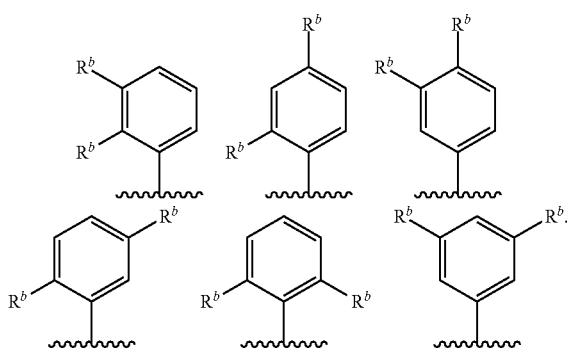

In some embodiments, R² is of one of the formulae:

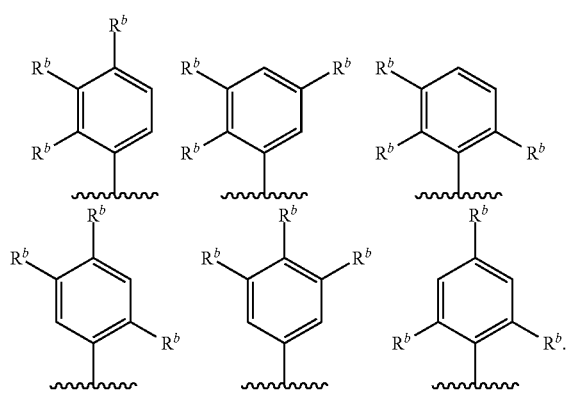

In some embodiments, R² is of one of the formulae:

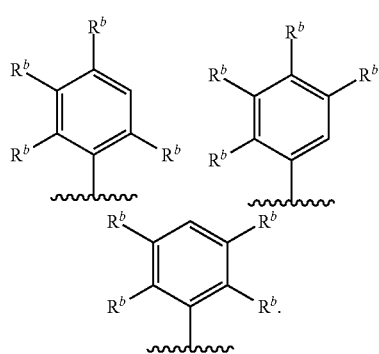

In some embodiments, R² is of the formula:

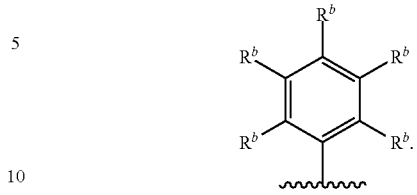

In some embodiments, R² is an optionally substituted 5-membered monocyclic saturated, partially saturated, or aromatic ring having 1-4 heteroatoms independently selected from nitrogen, oxygen, or sulfur. In some embodiments, R² is an unsubstituted 5-membered aromatic ring having 1-3 heteroatoms independently selected from nitrogen, oxygen, or sulfur. In some embodiments, R² is a substituted 5-membered aromatic ring having 1-3 heteroatoms independently selected from nitrogen, oxygen, or sulfur. In some embodiments, R² is optionally substituted thiophene. In some embodiments, R² is optionally substituted furan.

In some embodiments, R² is an unsubstituted 6-membered monocyclic saturated, partially saturated, or aromatic ring having 1-4 heteroatoms independently selected from nitrogen, oxygen, or sulfur. In some embodiments, R² is a substituted 6-membered monocyclic saturated, partially saturated, or aromatic ring having 1-4 heteroatoms independently selected from nitrogen, oxygen, or sulfur. In certain embodiments, R² is a substituted 6-membered monocyclic saturated ring having 1-3 heteroatoms independently selected from nitrogen, oxygen, or sulfur. In certain embodiments, R² is a substituted 6-membered monocyclic partially saturated ring having 1-3 heteroatoms independently selected from nitrogen, oxygen, or sulfur. In some embodiments, R² is a substituted 6-membered monocyclic aromatic ring containing one nitrogen.

In some embodiments, R² is an unsubstituted 8 membered saturated, partially saturated, or aromatic bicyclic ring having 0-4 heteroatoms independently selected from nitrogen, oxygen, or sulfur. In some embodiments, R² is a substituted 8 membered saturated, partially saturated, or aromatic bicyclic ring having 0-4 heteroatoms independently selected from nitrogen, oxygen, or sulfur. In some embodiments, R² is an optionally substituted 8 membered saturated bicyclic ring having 1-3 heteroatoms independently selected from nitrogen, oxygen, or sulfur. In some embodiments, R² is an optionally substituted 8 membered partially saturated bicyclic ring having 1-3 heteroatoms independently selected from nitrogen, oxygen, or sulfur.

In some embodiments, R² is an unsubstituted 9 membered saturated, partially saturated, or aromatic bicyclic ring having 0-4 heteroatoms independently selected from nitrogen, oxygen, or sulfur. In some embodiments, R² is a substituted 9 membered saturated, partially saturated, or aromatic bicyclic ring having 0-4 heteroatoms independently selected from nitrogen, oxygen, or sulfur. In some embodiments, R² is an optionally substituted 9 membered saturated bicyclic ring having 1-3 heteroatoms independently selected from nitrogen, oxygen, or sulfur. In some embodiments, R² is an optionally substituted 9 membered partially saturated bicyclic ring having 1-3 heteroatoms independently selected from nitrogen, oxygen, or sulfur. In some embodiments, R² is an optionally substituted 9 membered aromatic bicyclic ring having 1-3 heteroatoms independently selected from nitrogen, oxygen, or sulfur.

In some embodiments, R² is an unsubstituted 10 membered saturated, partially saturated, or aromatic bicyclic ring having 0-4 heteroatoms independently selected from nitrogen, oxygen, or sulfur. In some embodiments, R² is a substituted 10 membered saturated, partially saturated, or aromatic bicyclic ring having 0-4 heteroatoms independently selected from nitrogen, oxygen, or sulfur. In some embodiments, R² is an optionally substituted 10 membered saturated bicyclic ring having 1-3 heteroatoms independently selected from nitrogen, oxygen, or sulfur. In some embodiments, R² is an optionally substituted 10 membered partially saturated bicyclic ring having 1-3 heteroatoms independently selected from nitrogen, oxygen, or sulfur. In some embodiments, R² is an optionally substituted 10 membered aromatic bicyclic ring having 1-3 heteroatoms independently selected from nitrogen, oxygen, or sulfur.

In some embodiments, R² is not a nitrogen-containing heteroaryl or heterocyclic moiety. In some embodiments, R² is not an amide or lactam. In certain embodiments, R² is not a pyrrolidine, piperidine, or morpholine. In certain embodiments, R² is not pyridine or indole.

In some embodiments, R² is R. In some embodiments, R² is hydrogen, methyl, ethyl, propyl, butyl, pentyl, or hexyl. In some embodiments, R² is cyclopropyl, cyclobutyl, cyclopentyl, or cyclohexyl. In certain embodiments, R² is $C_{1-6}$ optionally substituted aliphatic.

In certain embodiments, R² and R¹ are the same. In certain embodiments, R² and R¹ are not the same.

In some embodiments, $R^b$ is independently selected from the group consisting of —R, halogen, —OR, —CN, —NO₂, —SR, —S(O)R, —SO₂R, —C(O)R, —CO₂R, —C(O)N(R)₂, —NRC(O)R, —NRC(O)N(R)₂, —NRSO₂R, —N(R)₂. In some embodiments, $R^b$ is an optionally substituted 5-6 membered monocyclic saturated, partially saturated, or aromatic ring having 1-4 heteroatoms independently selected from nitrogen, oxygen, or sulfur. In some embodiments, $R^b$ is an optionally substituted 8-10 membered saturated, partially saturated, or aromatic bicyclic ring having 0-4 heteroatoms independently selected from nitrogen, oxygen, or sulfur. In some embodiments, at least one $R^b$ is independently halogen. In some embodiments, at least two $R^b$ are independently halogen. In some embodiments, at least one $R^b$ is independently fluorine. In some embodiments, at least two $R^b$ are independently fluorine. In some embodiments, at least one $R^b$ is independently —OR. In some embodiments, at least two $R^b$ are independently —OR. In some embodiments, at least one $R^b$ is independently —OMe. In some embodiments, at least two $R^b$ are independently —OMe. In some embodiments, $R^b$ is substituted phenyl. In some embodiments, $R^b$ is unsubstituted phenyl. In some embodiments, $R^b$ is substituted naphthyl. In some embodiments, $R^b$ is unsubstituted naphthyl.

As defined above, R³ and R³' are independently hydrogen, halogen, optionally substituted $C_{1-6}$ aliphatic, or R³ and R³' are taken together to form $C_1$ alkenylene optionally substituted with one or two $R^c$ groups. In certain embodiments, R³ is hydrogen. In certain embodiments, R³ is hydrogen. In certain embodiments, at least one of R or R³' is hydrogen. In certain embodiments, both R³ and R³' are hydrogen. In certain embodiments, at least one of R³ or R³' is halogen. In certain embodiments, R³ is fluorine. In certain embodiments, R³' is fluorine. In certain embodiments, R³ and R³' are taken together to form $C_1$ alkenylene optionally substituted with one $R^c$ group.

As defined above, R is independently —R, —OR, —CN, —NO₂, —SR, —S(O)R, —SO₂R, —C(O)R, —CO₂R, —C(O)N(R)₂, —NRC(O)R, —NRC(O)N(R)₂, —NRSO₂R, —N(R)₂, phenyl, a 5-6 membered monocyclic saturated, partially saturated, or aromatic ring having 1-4 heteroatoms independently selected from nitrogen, oxygen, or sulfur, or an 8-10 membered saturated, partially saturated, or aromatic bicyclic ring having 0-4 heteroatoms independently selected from nitrogen, oxygen, or sulfur, and wherein $R^c$ is optionally substituted with t occurrences of $R^d$, wherein t is 0 to 5, inclusive. In some embodiments, $R^c$ is —R, hydrogen, halogen, —OR, —CN, —NO₂, —SR, —S(O)R, —SO₂R, —C(O)R, —CO₂R, —C(O)N(R)₂, —NRC(O)R, —NRC(O)N(R)₂, —NRSO₂R, or —N(R)₂. In some embodiments, $R^c$ is unsubstituted phenyl. In some embodiments, $R^c$ is phenyl substituted with t occurrences of $R^d$. In certain embodiments, t is 0, 1, 2, 3, 4, or 5.

In some embodiments, $R^c$ is of the formula:

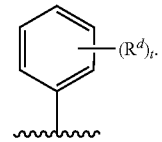

In some embodiments, $R^c$ is of one of the formulae:

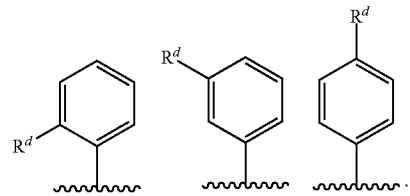

In some embodiments, $R^c$ is of one of the formulae:

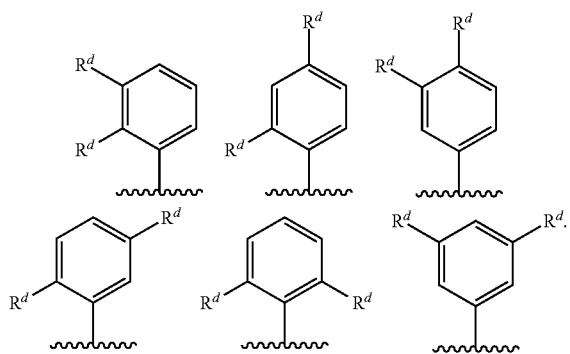

In some embodiments, $R^c$ is of one of the formulae:

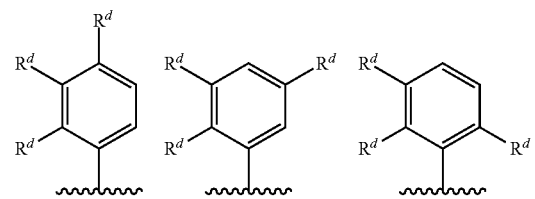

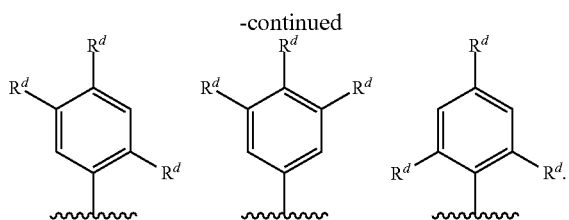

In some embodiments, $R^c$ is of one of the formulae:

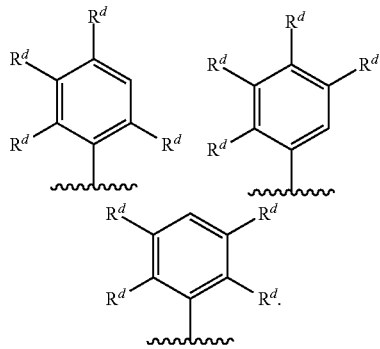

In some embodiments, $R^c$ is of the formula:

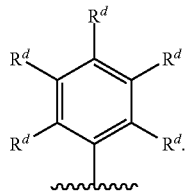

In some embodiments, $R^c$ is an optionally substituted 5-membered monocyclic saturated, partially saturated, or aromatic ring having 1-4 heteroatoms independently selected from nitrogen, oxygen, or sulfur. In some embodiments, $R^c$ is an unsubstituted 5-membered aromatic ring having 1-3 heteroatoms independently selected from nitrogen, oxygen, or sulfur. In some embodiments, $R^c$ is a substituted 5-membered aromatic ring having 1-3 heteroatoms independently selected from nitrogen, oxygen, or sulfur. In some embodiments, $R^c$ is optionally substituted thiophene. In some embodiments, $R^c$ is optionally substituted furan.

In some embodiments, $R^c$ is an unsubstituted 6-membered monocyclic saturated, partially saturated, or aromatic ring having 1-4 heteroatoms independently selected from nitrogen, oxygen, or sulfur. In some embodiments, $R^c$ is a substituted 6-membered monocyclic saturated, partially saturated, or aromatic ring having 1-4 heteroatoms independently selected from nitrogen, oxygen, or sulfur. In certain embodiments, $R^c$ is a substituted 6-membered monocyclic saturated ring having 1-3 heteroatoms independently selected from nitrogen, oxygen, or sulfur. In certain embodiments, $R^c$ is a substituted 6-membered monocyclic partially saturated ring having 1-3 heteroatoms independently selected from nitrogen, oxygen, or sulfur. In some embodiments, $R^c$ is a substituted 6-membered monocyclic aromatic ring containing one nitrogen.

In some embodiments, $R^c$ is an unsubstituted 8 membered saturated, partially saturated, or aromatic bicyclic ring having 0-4 heteroatoms independently selected from nitrogen, oxygen, or sulfur. In some embodiments, $R^c$ is a substituted 8 membered saturated, partially saturated, or aromatic bicyclic ring having 0-4 heteroatoms independently selected from nitrogen, oxygen, or sulfur. In some embodiments, $R^c$ is an optionally substituted 8 membered saturated bicyclic ring having 1-3 heteroatoms independently selected from nitrogen, oxygen, or sulfur. In some embodiments, $R^c$ is an optionally substituted 8 membered partially saturated bicyclic ring having 1-3 heteroatoms independently selected from nitrogen, oxygen, or sulfur.

In some embodiments, $R^c$ is an unsubstituted 9 membered saturated, partially saturated, or aromatic bicyclic ring having 0-4 heteroatoms independently selected from nitrogen, oxygen, or sulfur. In some embodiments, $R^c$ is a substituted 9 membered saturated, partially saturated, or aromatic bicyclic ring having 0-4 heteroatoms independently selected from nitrogen, oxygen, or sulfur. In some embodiments, $R^c$ is an optionally substituted 9 membered saturated bicyclic ring having 1-3 heteroatoms independently selected from nitrogen, oxygen, or sulfur. In some embodiments, $R^c$ is an optionally substituted 9 membered partially saturated bicyclic ring having 1-3 heteroatoms independently selected from nitrogen, oxygen, or sulfur. In some embodiments, $R^c$ is an optionally substituted 9 membered aromatic bicyclic ring having 1-3 heteroatoms independently selected from nitrogen, oxygen, or sulfur.

In some embodiments, $R^c$ is an unsubstituted 10 membered saturated, partially saturated, or aromatic bicyclic ring having 0-4 heteroatoms independently selected from nitrogen, oxygen, or sulfur. In some embodiments, $R^c$ is a substituted 10 membered saturated, partially saturated, or aromatic bicyclic ring having 0-4 heteroatoms independently selected from nitrogen, oxygen, or sulfur. In some embodiments, $R^c$ is an optionally substituted 10 membered saturated bicyclic ring having 1-3 heteroatoms independently selected from nitrogen, oxygen, or sulfur. In some embodiments, $R^c$ is an optionally substituted 10 membered partially saturated bicyclic ring having 1-3 heteroatoms independently selected from nitrogen, oxygen, or sulfur. In some embodiments, $R^c$ is an optionally substituted 10 membered aromatic bicyclic ring having 1-3 heteroatoms independently selected from nitrogen, oxygen, or sulfur.

In some embodiments, $R^c$ is:

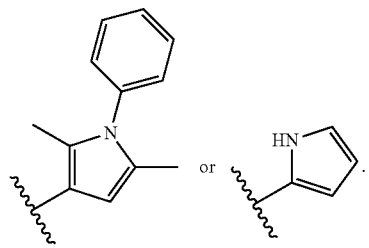 [SMILES: *c1cc(C)n(-c2ccccc2)c1C ; *c1ccc[nH]1]

In some embodiments, each $R^d$ is independently —R, —OR, —CN, —C(R)$_3$, —NO$_2$, —SR, —S(O)R, —SO$_2$R, —C(O)R, —CO$_2$R, —C(O)N(R)$_2$, —NRC(O)R, —NRC(O)N(R)$_2$, —NRSO$_2$R, or —N(R)$_2$. In certain embodiments, $R^d$ is fluorine, chlorine, bromine, or iodine. In certain embodiments, at least one $R^d$ is independently fluorine, chlorine, bromine, or iodine. In certain embodiments, at least two $R^d$ are independently fluorine, chlorine, bromine, or iodine. In some embodiments, $R^d$ is —OR. In certain embodiments, at least one $R^d$ is —OR. In certain embodiments, at least two $R^d$ are —OR. In certain embodiments wherein $R^d$ is —OR, R is methyl. In certain embodiments wherein $R^d$ is —OR, R is phenyl. In certain embodiments wherein $R^d$ is —OR, R is benzyl. In certain embodiments wherein $R^d$ is —OR, R is optionally substituted $C_{1-6}$ aliphatic.

In some embodiments, the present invention provides a compound of one of the formulae:

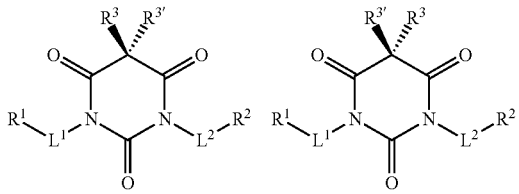

or a pharmaceutically acceptable salt thereof, wherein $R^1$, $L^1$, $R^2$, $L^2$, $R^3$, and $R^{3'}$ are as defined and described herein.

In some embodiments, the provided compound is of one of the formulae:

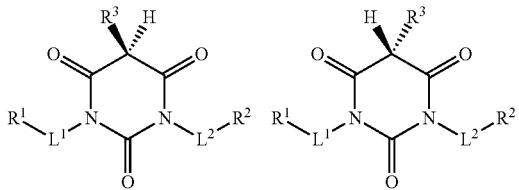

or a pharmaceutically acceptable salt thereof, wherein $R^1$, $L^1$, $R^2$, $L^2$, $R^3$, and $R^{3'}$ are as defined and described herein.

In some embodiments, the provided compound is of the formula:

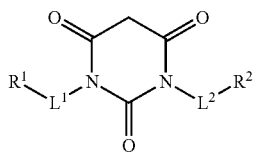

or a pharmaceutically acceptable salt thereof, wherein $R^1$, $L^1$, $R^2$, and $L^2$ are as defined and described herein.

In some embodiments, the provided compound is of one of the formulae:

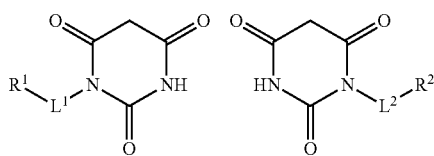

or a pharmaceutically acceptable salt thereof, wherein $R^1$, $L^1$, $R^2$, and $L^2$ are as defined above.

In some embodiments, the provided compound is of one of the formulae:

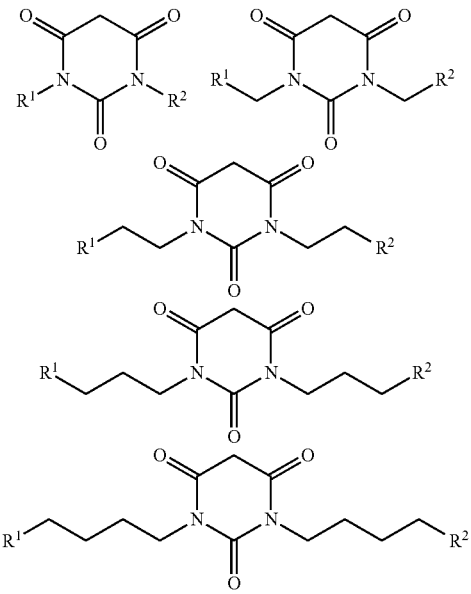

or a pharmaceutically acceptable salt thereof, wherein $R^1$ and $R^2$ are as defined and described herein.

In some embodiments, the provided compound is of one of the formulae:

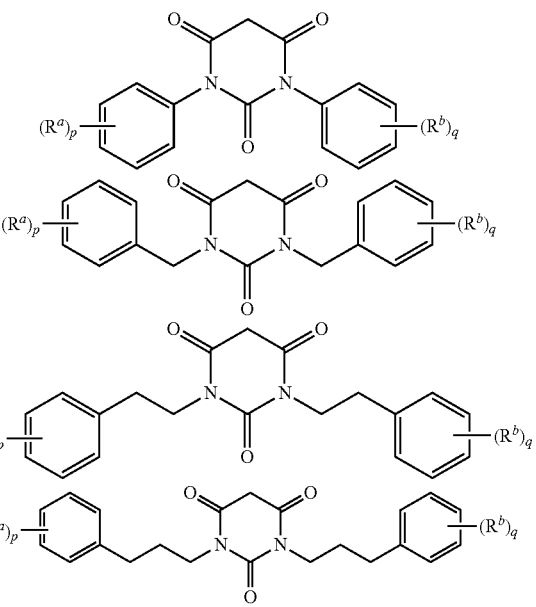

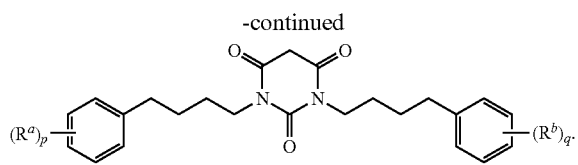

or a pharmaceutically acceptable salt thereof, wherein $R^a$, p, $R^b$, and q are as defined and described herein.

In some embodiments, the provided compound is of one of the formulae:

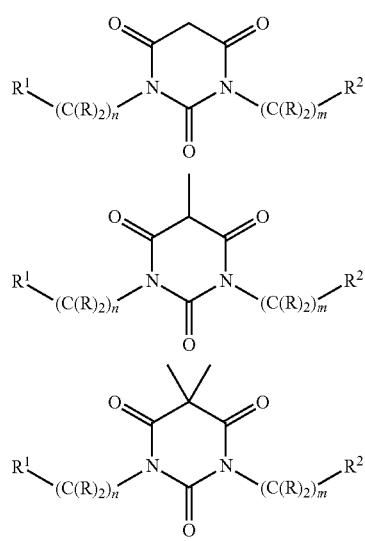

or a pharmaceutically acceptable salt thereof, wherein $R^1$, n, $R^2$, m, and R are as defined and described herein.

In some embodiments, the provided compound is of formula:

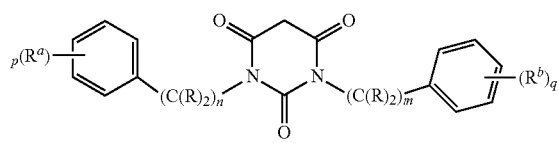

or a pharmaceutically acceptable salt thereof, wherein $R^a$, p, n, $R^b$, q, m, and R are as defined and described herein.

In some embodiments, the provided compound is of formula:

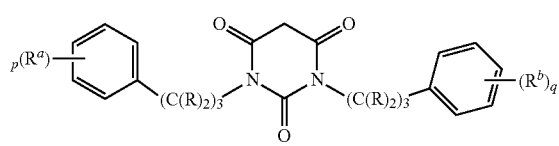

or a pharmaceutically acceptable salt thereof, wherein $R^a$, p, $R^b$, q, and R are as defined and described herein.

In some embodiments, the provided compound is of either of the formulae:

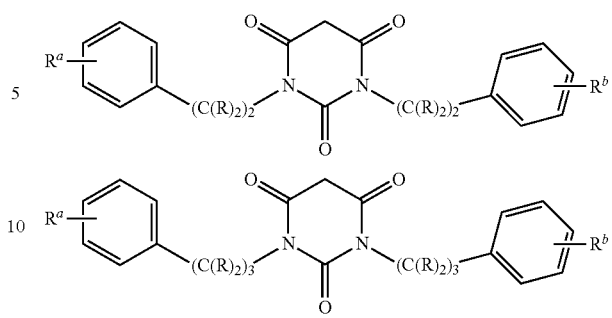

or a pharmaceutically acceptable salt thereof, wherein $R^a$, $R^b$, and R are as defined and described herein.

In some embodiments, the provided compound is of one of the formulae:

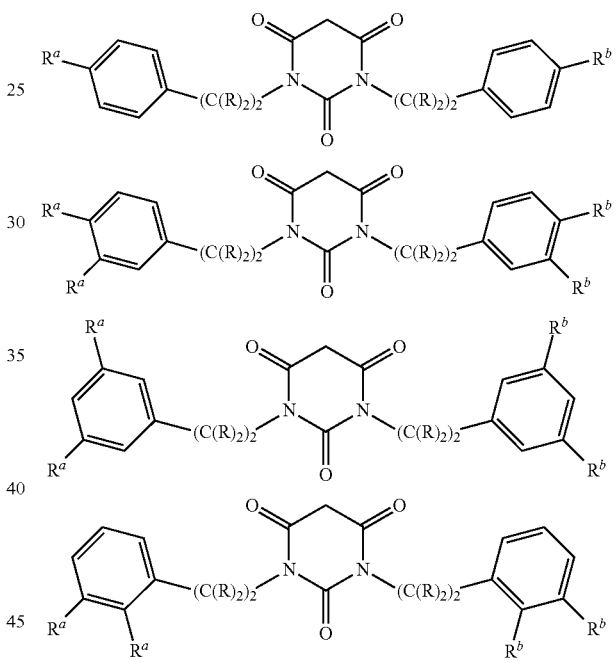

or a pharmaceutically acceptable salt thereof, wherein $R^a$, $R^b$, and R are as defined and described herein.

In some embodiments, the provided compound is of one of the formulae:

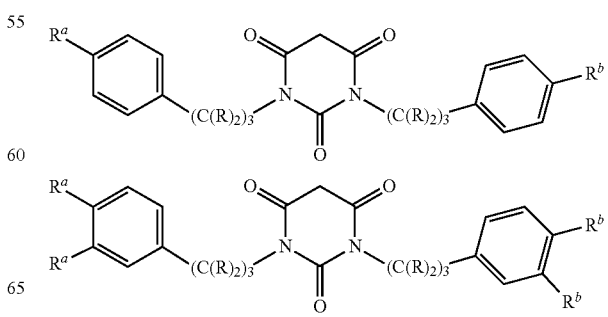

-continued

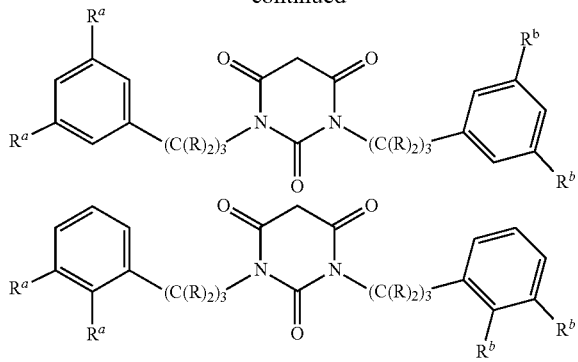

or a pharmaceutically acceptable salt thereof, wherein $R^a$, $R^b$, and R are as defined and described herein.

In some embodiments, the provided compound is of the formula:

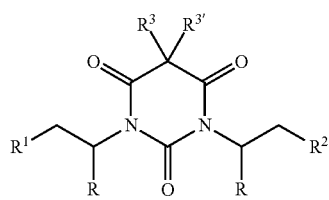

or a pharmaceutically acceptable salt thereof, wherein $R^1$, $R^2$, $R^3$, $R^{3'}$, and R are as defined and described herein.

In some embodiments, the provided compound is of the formula:

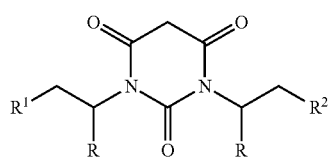

or a pharmaceutically acceptable salt thereof, wherein $R^1$, $R^2$, and R are as defined and described herein.

In some embodiments, the provided compound is of either of the formulae:

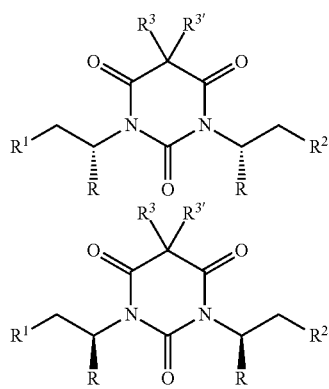

or a pharmaceutically acceptable salt thereof, wherein $R^1$, $R^2$, $R^3$, $R^{3'}$, and R are as defined and described herein.

In some embodiments, the provided compound is of either of the formulae:

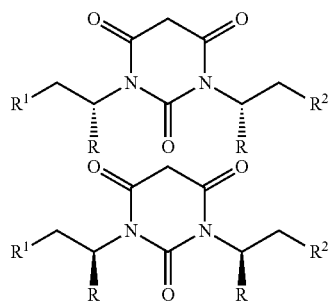

or a pharmaceutically acceptable salt thereof, wherein R, $R^2$, and R are as defined and described herein.

In some embodiments, the provided compound is of either of the formulae:

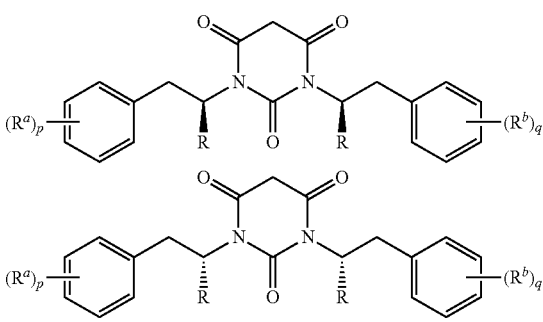

or a pharmaceutically acceptable salt thereof, wherein $R^a$, p, $R^b$, q, and R are as defined and described herein.

In some embodiments, the provided compound is of either of the formulae:

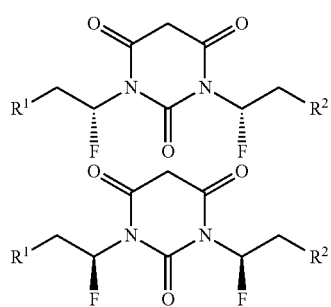

or a pharmaceutically acceptable salt thereof, wherein $R^1$ and $R^2$ are as defined and described herein.

In some embodiments, the provided compound is of either of the formulae:

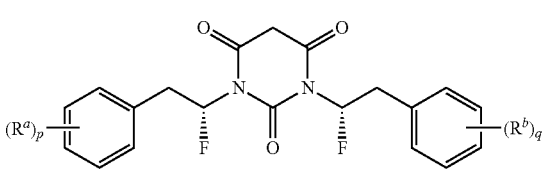

-continued

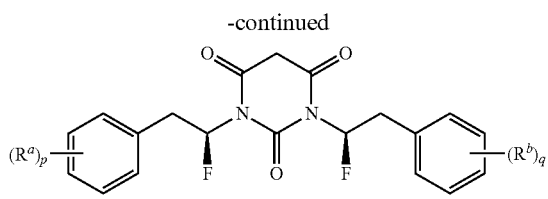

or a pharmaceutically acceptable salt thereof, wherein $R^a$, p, $R^b$, and q are as defined and described herein.

In some embodiments, the provided compound is of either of the formulae:

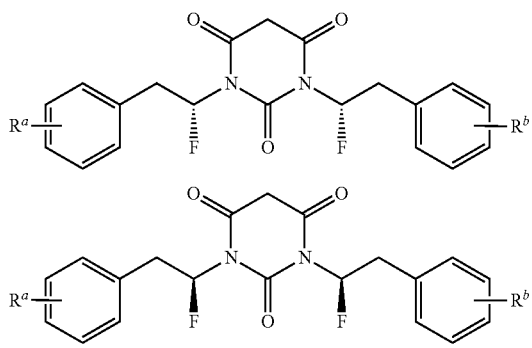

or a pharmaceutically acceptable salt thereof, wherein $R^a$ and $R^b$ are as defined and described herein.

In some embodiments, the provided compound is of either of the formulae:

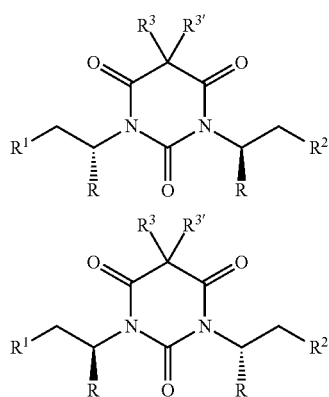

or a pharmaceutically acceptable salt thereof, wherein $R^1$, $R^2$, $R^3$, $R^{3'}$, and R are as defined and described herein.

In some embodiments, the provided compound is of either of the formulae:

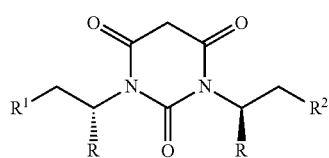

-continued

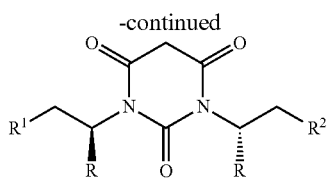

or a pharmaceutically acceptable salt thereof, wherein $R^1$, $R^2$, and R are as defined and described herein.

In some embodiments, the provided compound is of either of the formulae:

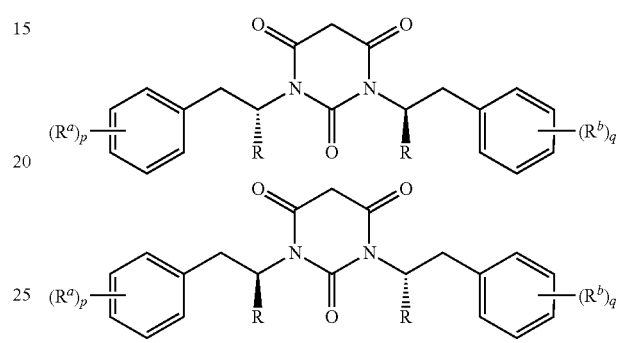

or a pharmaceutically acceptable salt thereof, wherein $R^a$, p, $R^b$, q, and R are as defined and described herein.

In some embodiments, the provided compound is of either of the formulae:

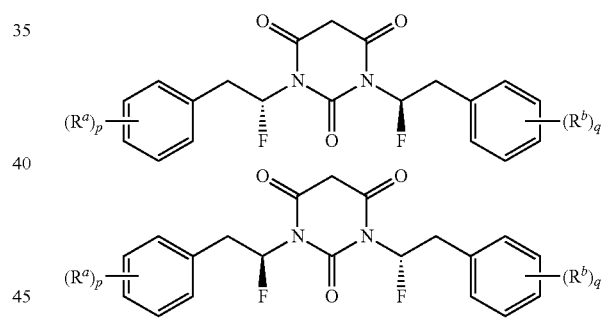

or a pharmaceutically acceptable salt thereof, wherein $R^a$, p, $R^b$, and q are as defined and described herein.

In some embodiments, the provided compound is of either of the formulae:

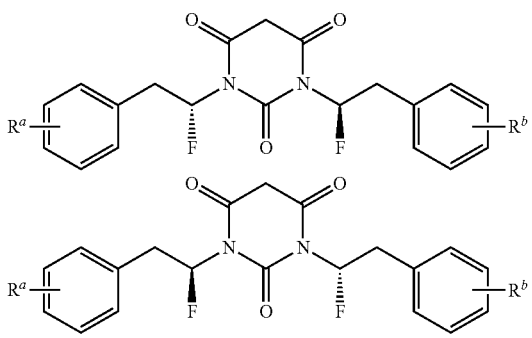

or a pharmaceutically acceptable salt thereof, wherein $R^a$ and $R^b$ are as defined and described herein.

In some embodiments, the provided compound is of the formula:

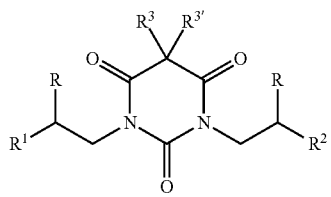

or a pharmaceutically acceptable salt thereof, wherein $R^1$, $R^2$, $R^3$, $R^{3'}$, and R are as defined and described herein.

In some embodiments, the provided compound is of the formula:

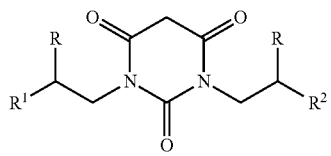

or a pharmaceutically acceptable salt thereof, wherein $R^1$, $R^2$, and R are as defined and described herein.

In some embodiments, the provided compound is of either of the formulae:

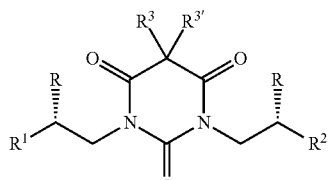

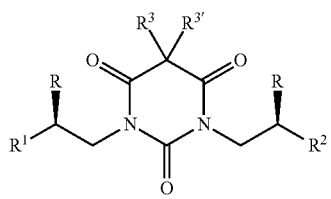

or a pharmaceutically acceptable salt thereof, wherein $R^1$, $R^2$, $R^3$, $R^{3'}$, and R are as defined and described herein.

In some embodiments, the provided compound is of either of the formulae:

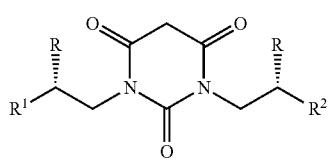

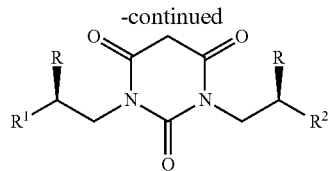

or a pharmaceutically acceptable salt thereof, wherein $R^1$, $R^2$, and R are as defined and described herein.

In some embodiments, the provided compound is of either of the formulae:

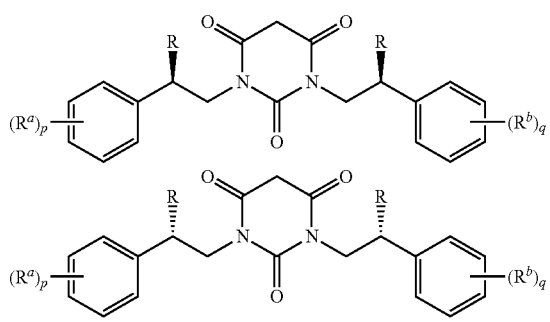

or a pharmaceutically acceptable salt thereof, wherein $R^a$, p, $R^b$, q, and R are as defined and described herein.

In some embodiments, the provided compound is of either of the formulae:

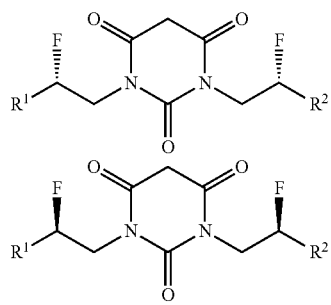

or a pharmaceutically acceptable salt thereof, wherein $R^1$ and $R^2$ are as defined and described herein.

In some embodiments, the provided compound is of either of the formulae:

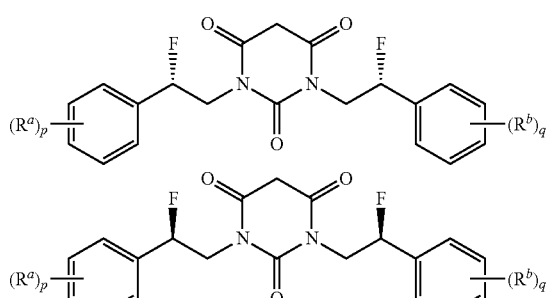

or a pharmaceutically acceptable salt thereof, wherein $R^a$, p, $R^b$, and q are as defined and described herein.

In some embodiments, the provided compound is of either of the formulae:

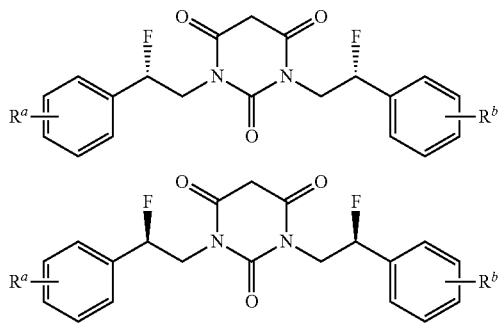

or a pharmaceutically acceptable salt thereof, wherein $R^a$ and $R^b$ are as defined and described herein.

In some embodiments, the provided compound is of either of the formulae:

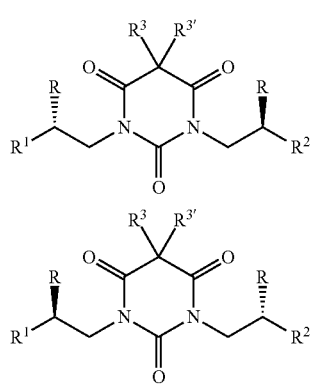

or a pharmaceutically acceptable salt thereof, wherein R, $R^2$, $R^3$, $R^{3'}$, and R are as defined and described herein.

In some embodiments, the provided compound is of either of the formulae:

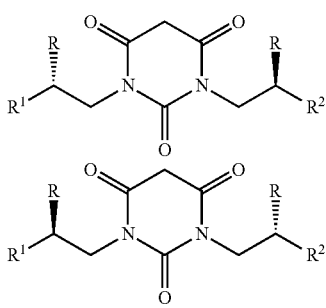

or a pharmaceutically acceptable salt thereof, wherein $R^1$, $R^2$, and R are as defined and described herein.

In some embodiments, the provided compound is of either of the formulae:

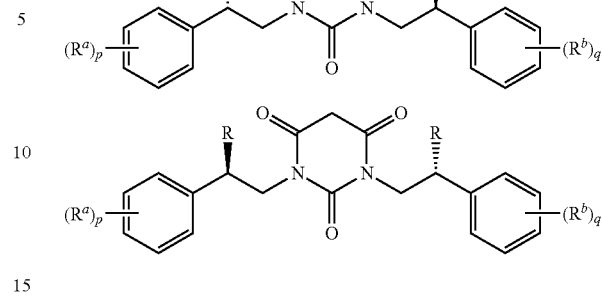

or a pharmaceutically acceptable salt thereof, wherein $R^a$, p, $R^b$, q, and R are as defined and described herein.

In some embodiments, the provided compound is of either of the formulae:

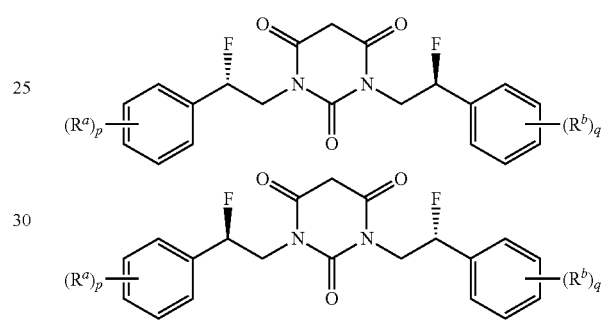

or a pharmaceutically acceptable salt thereof, wherein $R^a$, p, $R^b$, and q are as defined and described herein.

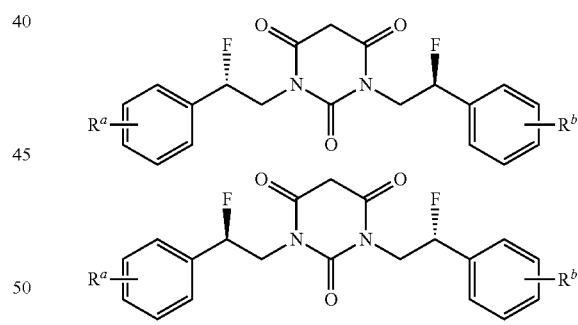

or a pharmaceutically acceptable salt thereof, wherein $R^a$ and $R^b$ are as defined and described In some embodiments, the provided compound is of either of the formulae:

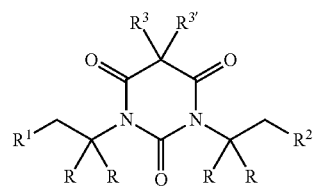

-continued

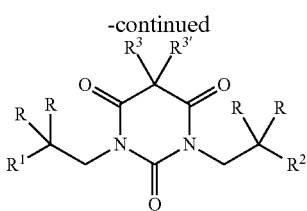

or a pharmaceutically acceptable salt thereof, wherein $R^1$, $R^2$, $R^3$, $R^{3'}$, and R are as defined and described herein.

In some embodiments, the provided compound is of either of the formulae:

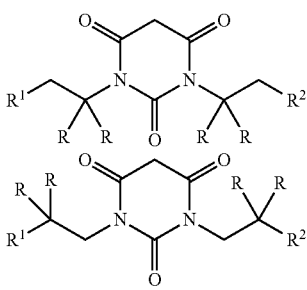

or a pharmaceutically acceptable salt thereof, wherein R, $R^2$, and R are as defined and described herein.

In some embodiments, the provided compound is of either of the formulae:

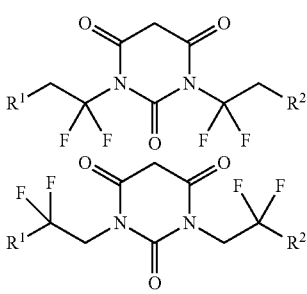

or a pharmaceutically acceptable salt thereof wherein $R^1$ and $R^2$ are as defined and described herein.

In some embodiments, the provided compound is of either of the formulae:

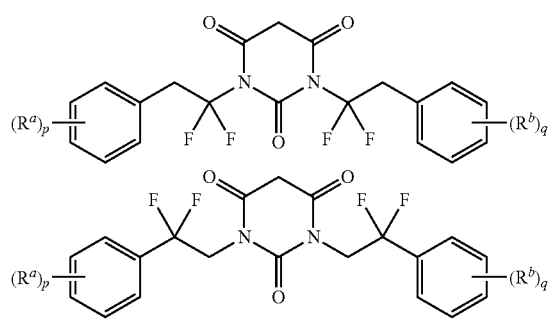

or a pharmaceutically acceptable salt thereof, wherein $R^a$, p, $R^b$, and q are as defined and described herein. In certain embodiments, the compound is as depicted above and p and q are each 2.

In some embodiments, the provided compound is of either of the formulae:

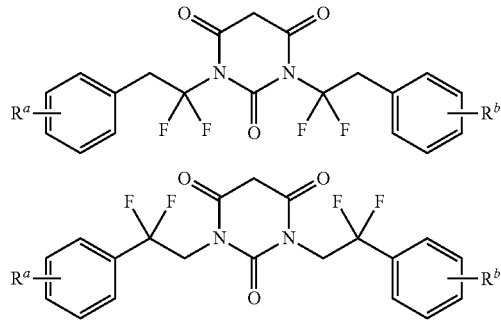

or a pharmaceutically acceptable salt thereof, wherein $R^a$ and $R^b$ are as defined and described herein.

In some embodiments, the provided compound is of any one of the formulae:

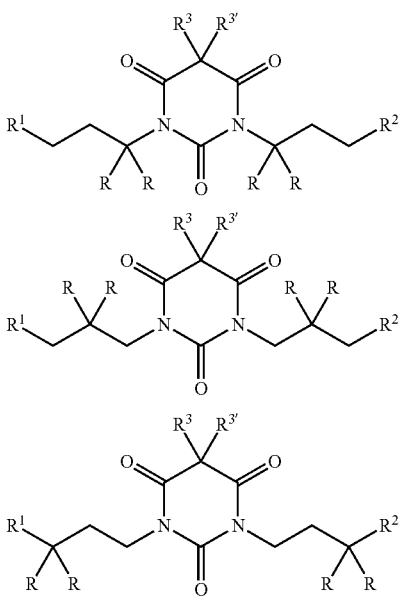

or a pharmaceutically acceptable salt thereof, wherein $R^1$, $R^2$, $R^3$, $R^{3'}$, and R are as defined and described herein.

In some embodiments, the provided compound is of any one of the formulae:

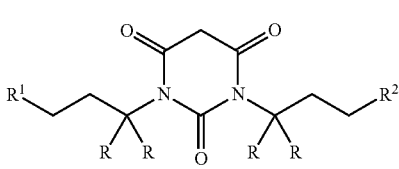

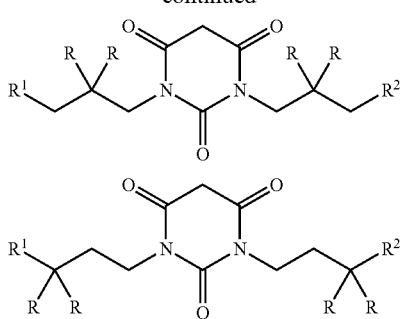

or a pharmaceutically acceptable salt thereof, wherein $R^1$, $R^2$, and R are as defined and described herein.

In some embodiments, the provided compound is of any one of the formulae:

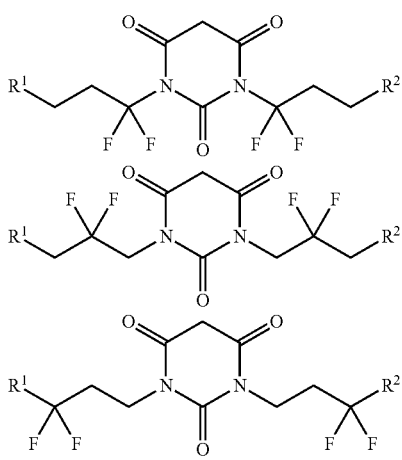

or a pharmaceutically acceptable salt thereof wherein $R^1$ and $R^2$ are as defined and described herein.

In some embodiments, the provided compound is of any one of the formulae:

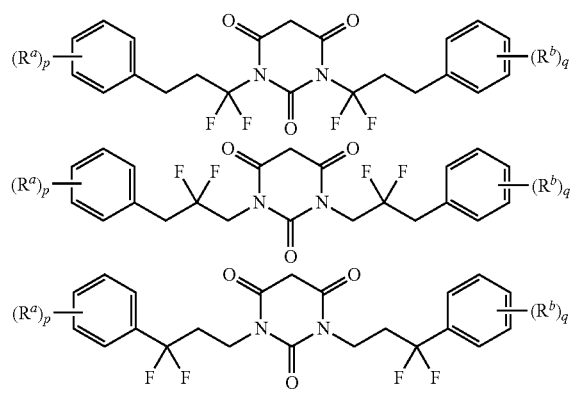

or a pharmaceutically acceptable salt thereof, wherein $R^a$, p, $R^b$, and q are as defined and described herein.

In some embodiments, the provided compound is of any one of the formulae:

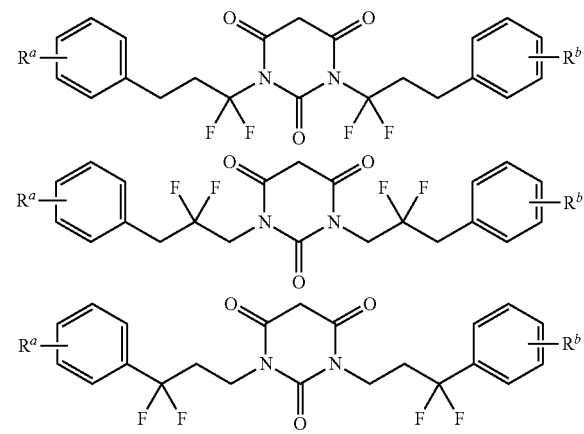

or a pharmaceutically acceptable salt thereof, wherein $R^a$ and $R^b$ are as defined and described herein.

In some embodiments, the provided compound is of any one of the formulae:

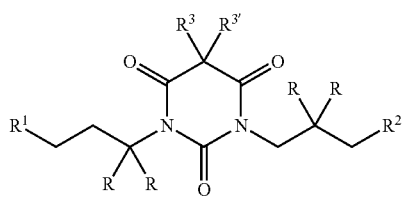

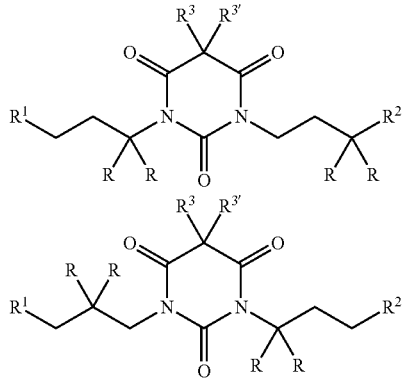

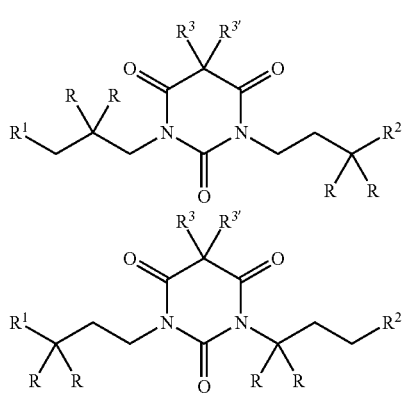

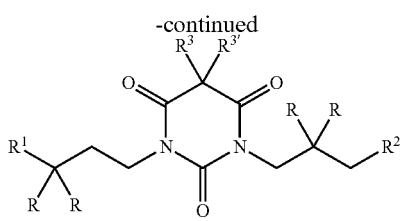

or a pharmaceutically acceptable salt thereof, wherein $R^1$, $R^2$, $R^3$, $R^{3'}$, and R are as defined and described herein. In some embodiments, the provided compound is as depicted above and each occurrence of R is independently hydrogen or halogen. In certain embodiments, the provided compound is as depicted above and each occurrence of R is independently hydrogen or fluorine.

In some embodiments, the provided compound is of the formula:

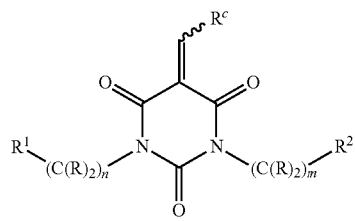

or a pharmaceutically acceptable salt thereof, wherein $R^1$, n, $R^2$, m, $R^c$, and R are as defined and described herein.

In some embodiments, the provided compound is of the formula:

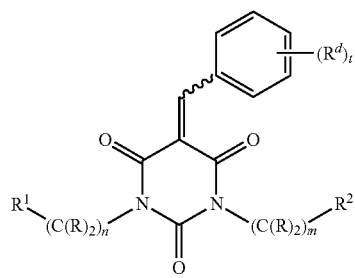

or a pharmaceutically acceptable salt thereof, wherein $R^1$, n, $R^2$, m, $R^d$, t, and R are as defined and described herein.

In some embodiments, the provided compound is of any one of the formulae:

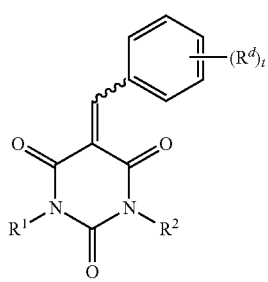

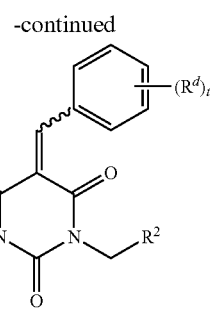

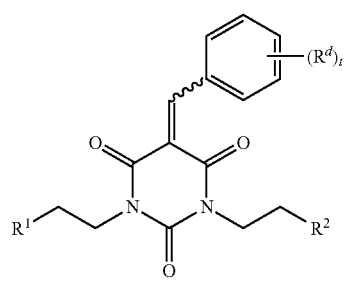

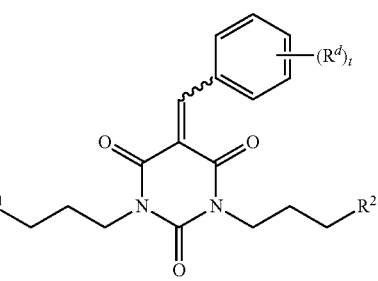

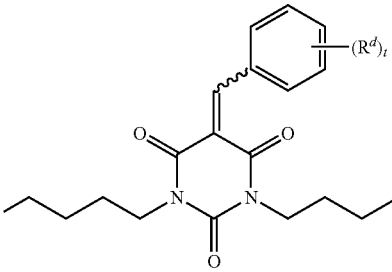

or a pharmaceutically acceptable salt thereof, wherein $R^1$, $R^2$, $R^d$, and t are as defined and described herein.

In some embodiments, the provided compound is of the formula:

or a pharmaceutically acceptable salt thereof, wherein $R^a$, p, n, $R^b$, q, m, $R^c$, and R are as defined and described herein.

In some embodiments, the provided compound is of the formula:

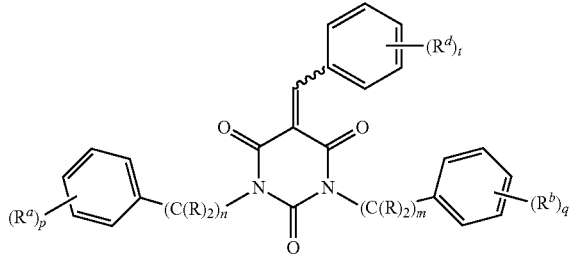

or a pharmaceutically acceptable salt thereof, wherein $R^a$, p, n, $R^b$, q, m, $R^d$, t, and R are as defined and described herein.

In some embodiments, the provided compound is of either of the formulae:

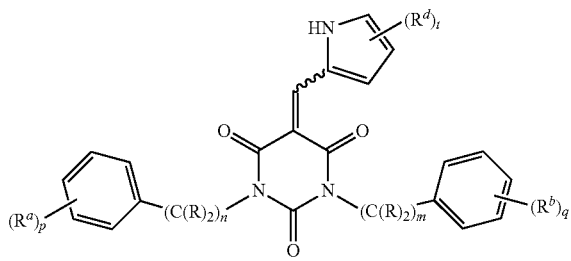

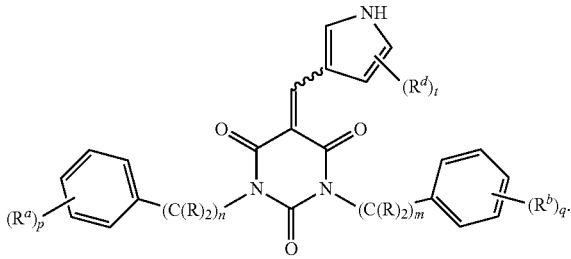

or a pharmaceutically acceptable salt thereof, wherein $R^a$, p, n, $R^b$, q, m, $R^d$, t, and R are as defined and described herein.

In some embodiments, the provided compound is of either of the formulae:

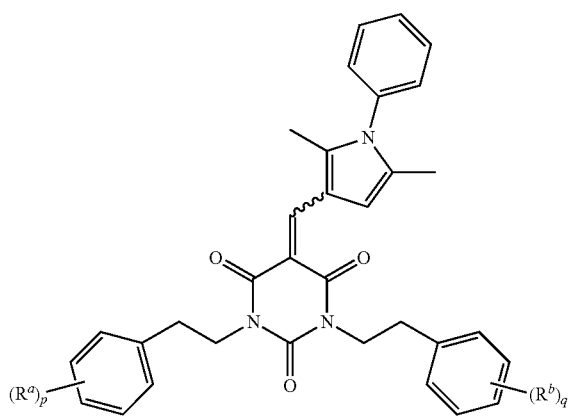

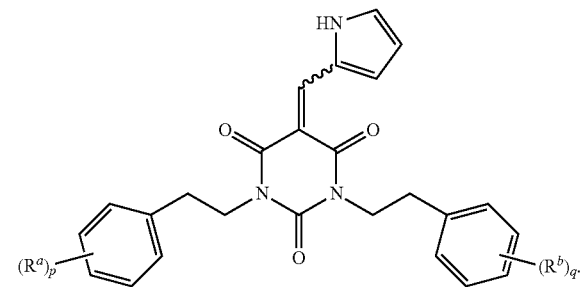

or a pharmaceutically acceptable salt thereof, wherein $R^a$, p, $R^b$, and q are as defined and described herein.

In some embodiments, the provided compound is of either of the formulae:

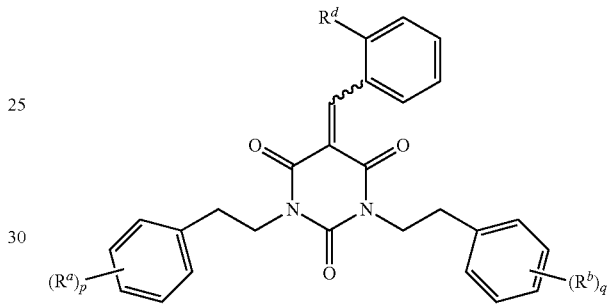

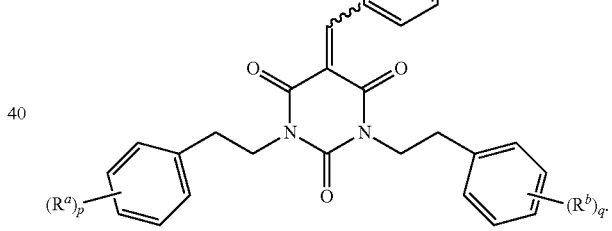

or a pharmaceutically acceptable salt thereof, wherein $R^a$, p, $R^b$, q, and $R^d$ are as defined and described herein.

In some embodiments, the provided compound is of either of the formulae:

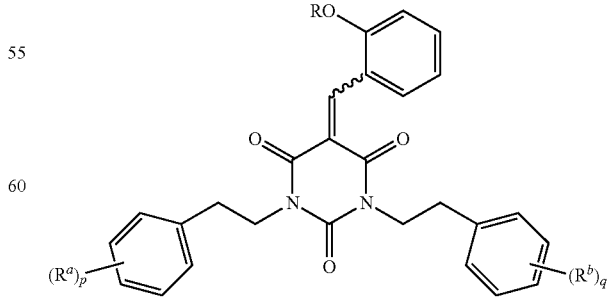

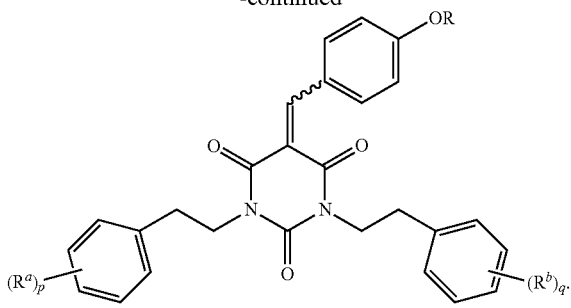

or a pharmaceutically acceptable salt thereof, wherein $R^a$, p, $R^b$, q, and R are as defined and described herein.

In some embodiments, the provided compound has a structure depicted in any one of the following formulae:

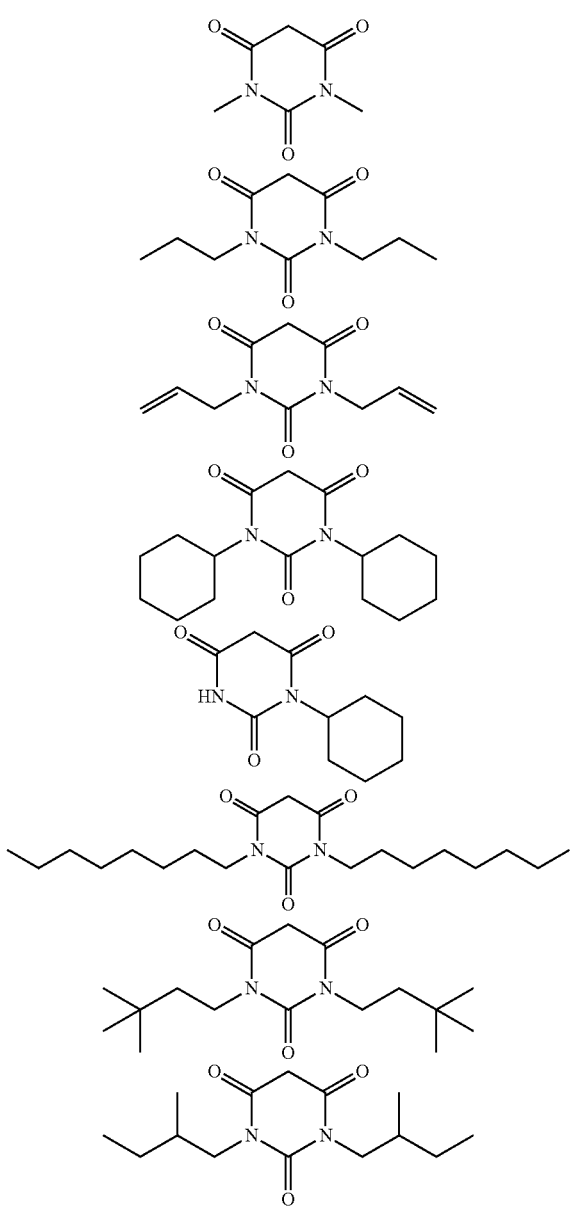

or a pharmaceutically acceptable salt thereof.

In some embodiments, the provided compound has a structure depicted in any one of the following formulae:

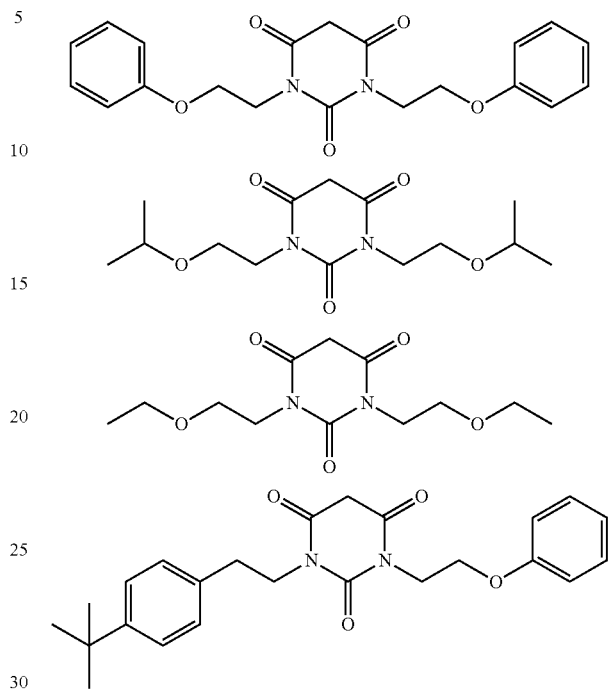

or a pharmaceutically acceptable salt thereof.

In some embodiments, the provided compound has a structure depicted in any one of the following formulae:

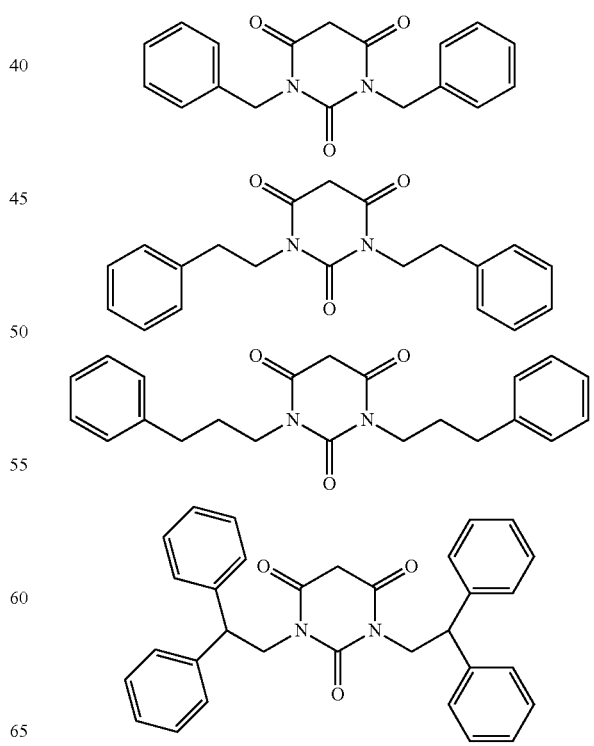

51
-continued
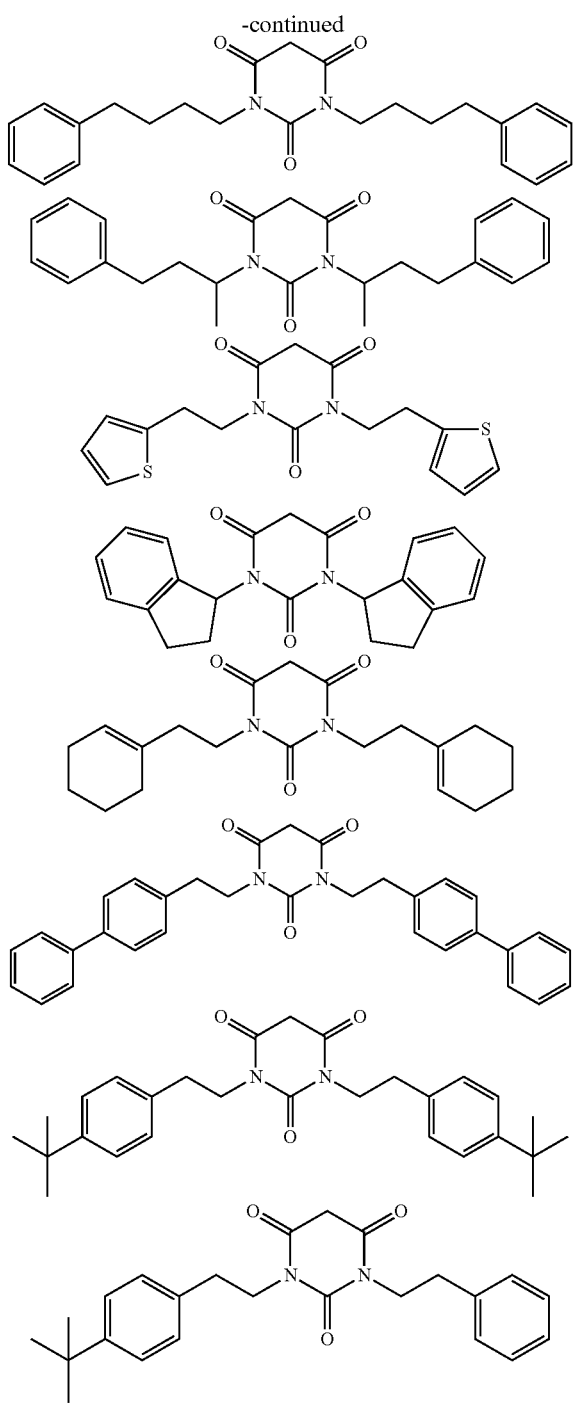
or a pharmaceutically acceptable salt thereof.
In some embodiments, the provided compound has a structure depicted in any one of the following formulae:
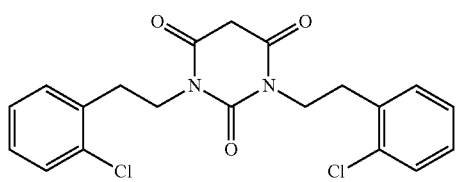
52
-continued
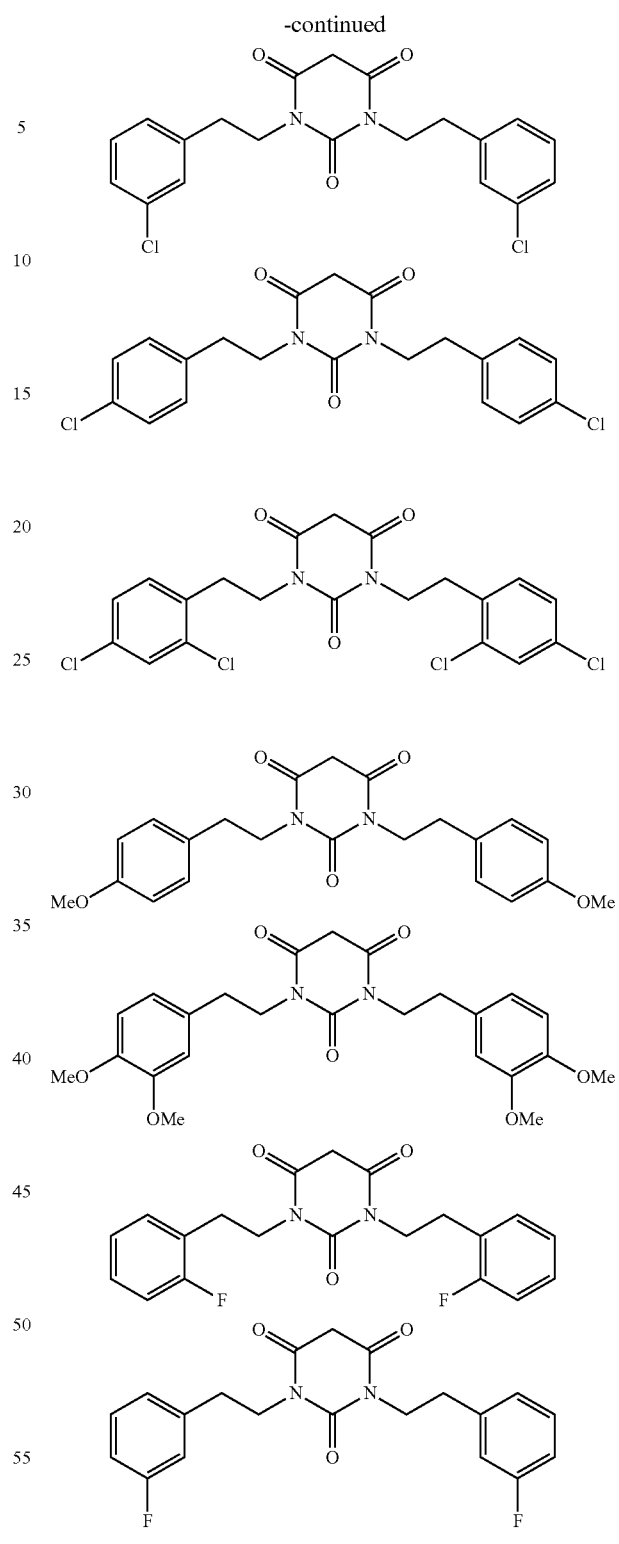
or a pharmaceutically acceptable salt thereof.

In some embodiments, the provided compound has a structure depicted in any one of the following formulae:
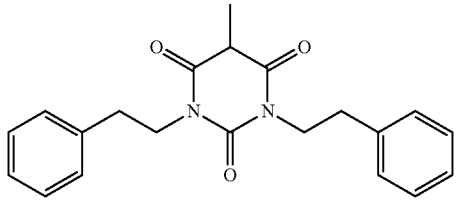
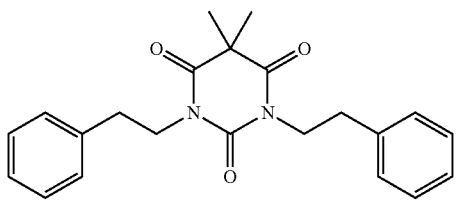
or a pharmaceutically acceptable salt thereof.
In some embodiments, the provided compound has a structure depicted in any one of the following formulae:
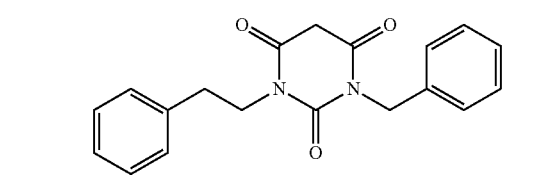
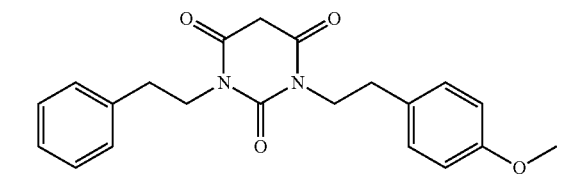
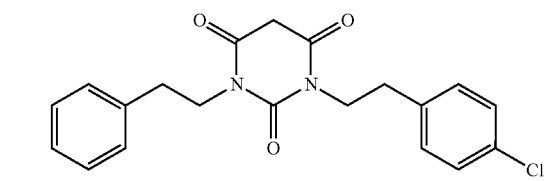
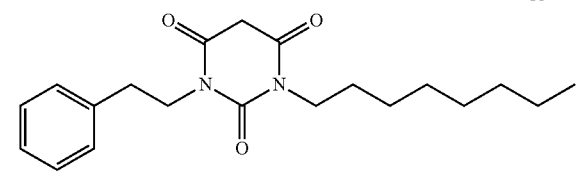
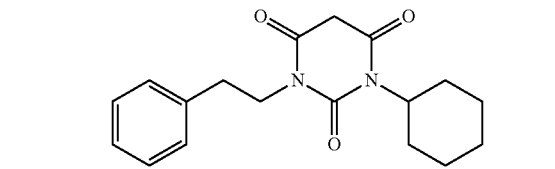
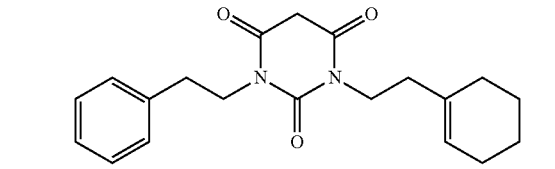
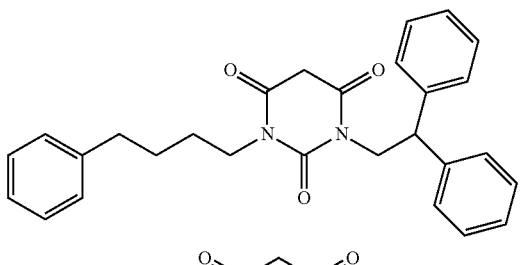
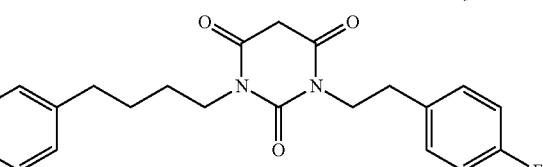
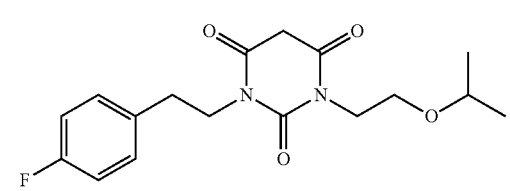
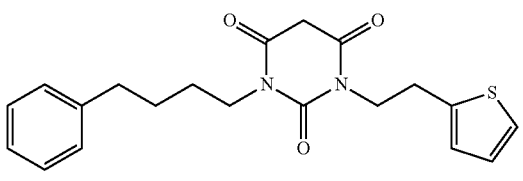
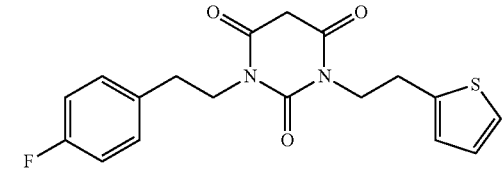
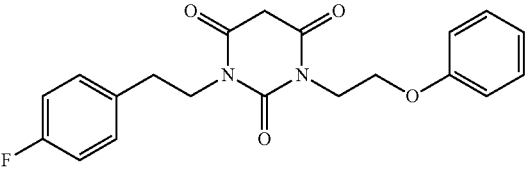
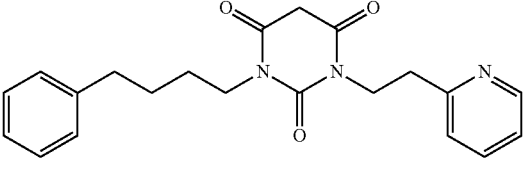
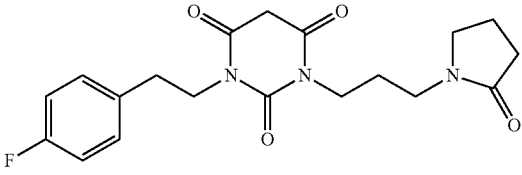
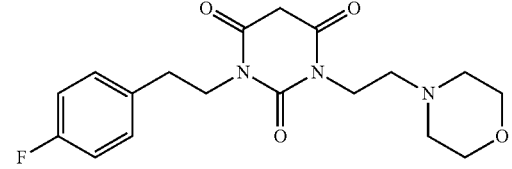

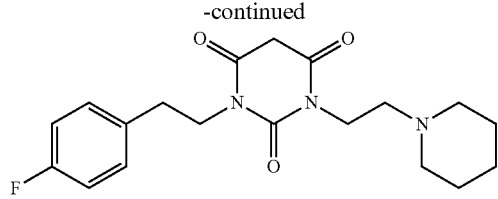
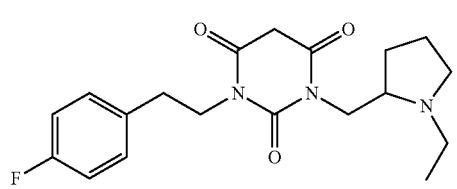
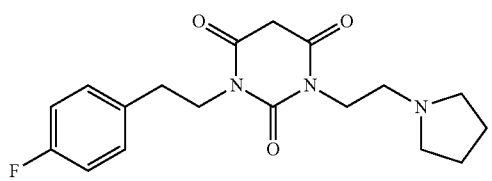
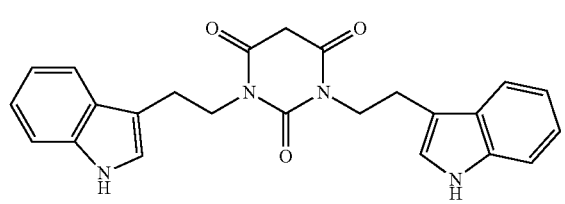
or a pharmaceutically acceptable salt thereof.
In some embodiments, the provided compound has a structure depicted in any one of the following formulae:
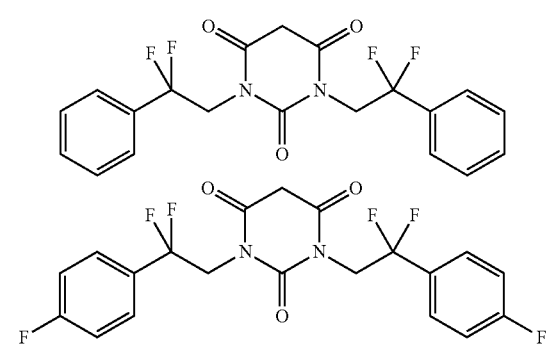
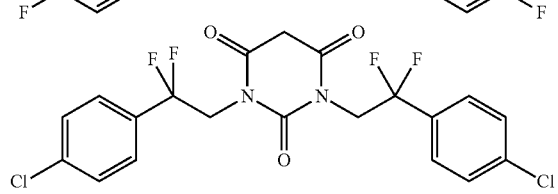
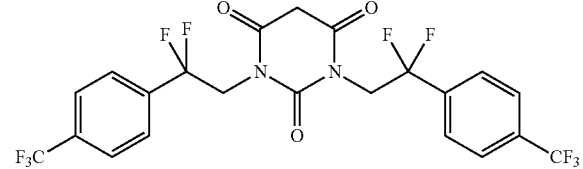
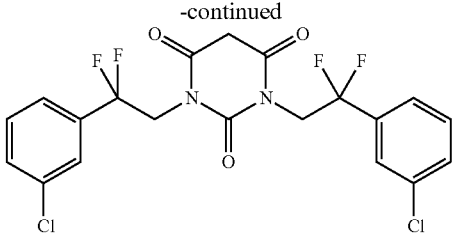
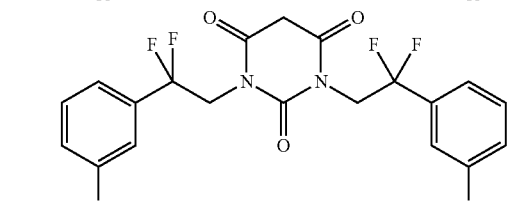
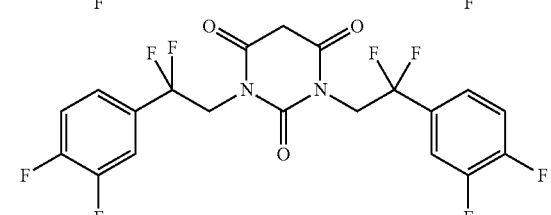
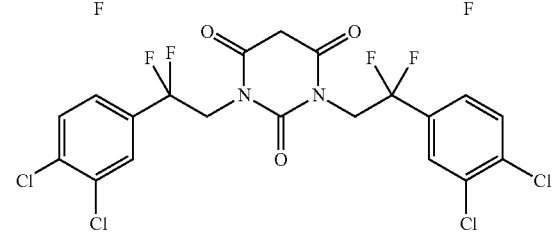
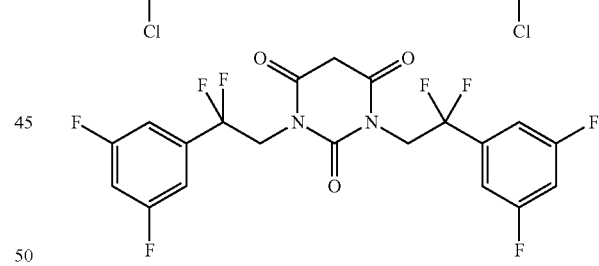
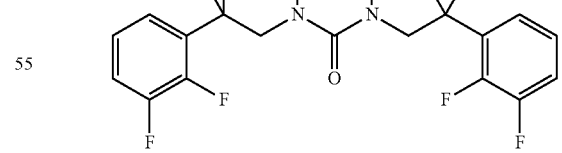
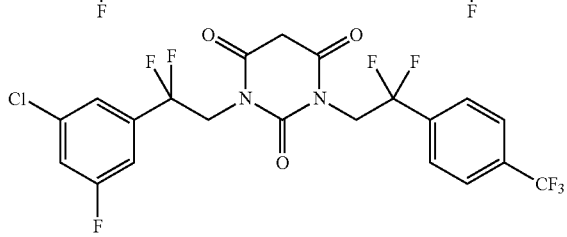

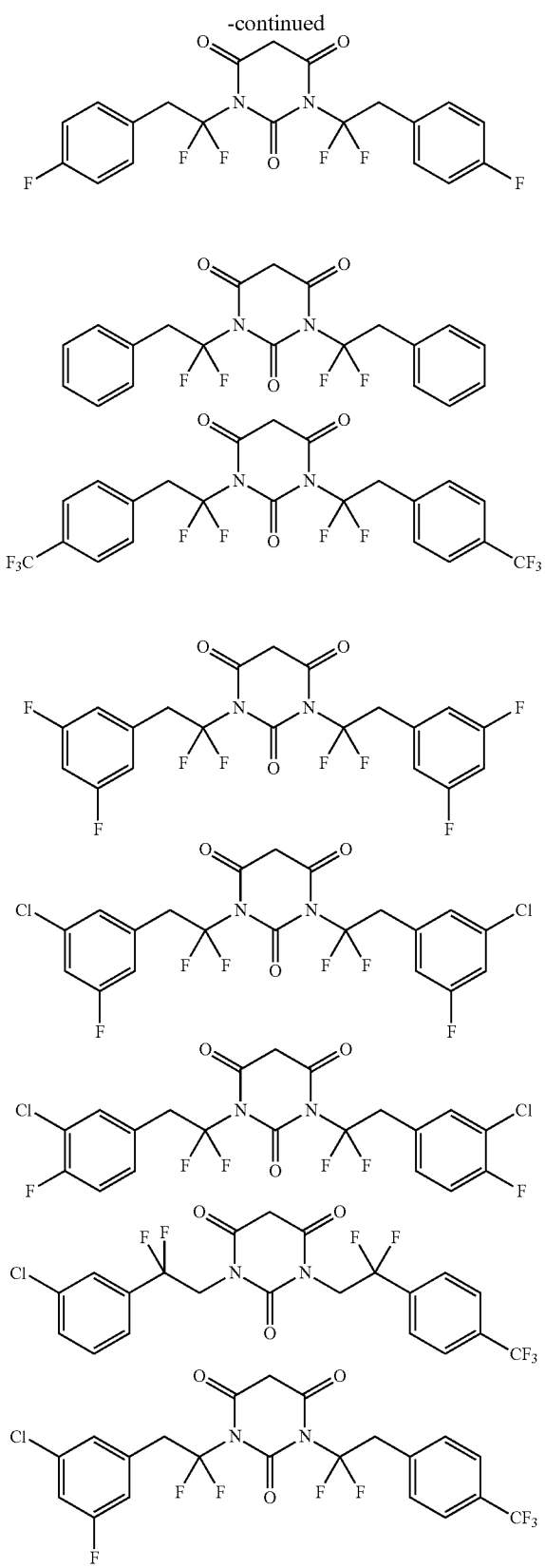
or a pharmaceutically acceptable salt thereof.
In some embodiments, the provided compound has a structure depicted in any one of the following formulae:
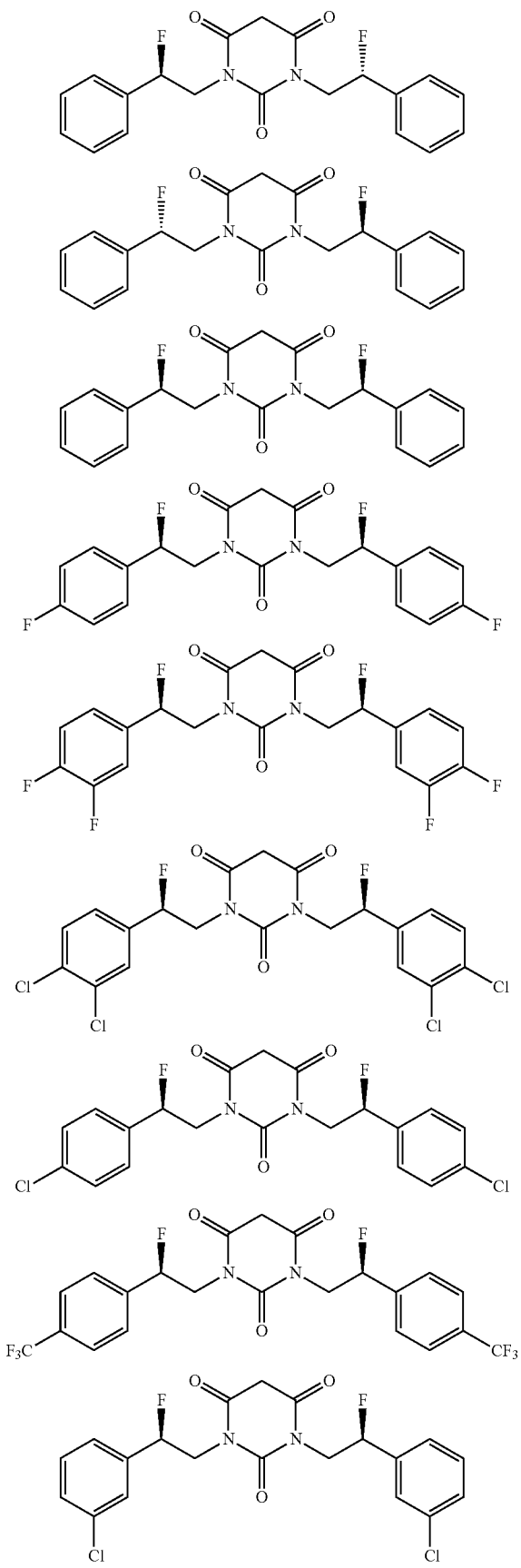

59
-continued

60
-continued

61
-continued
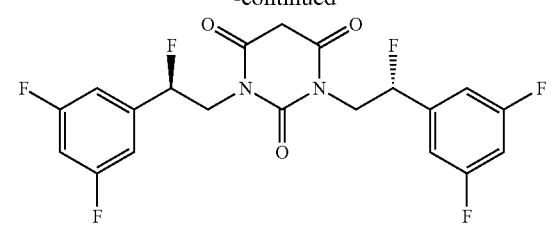
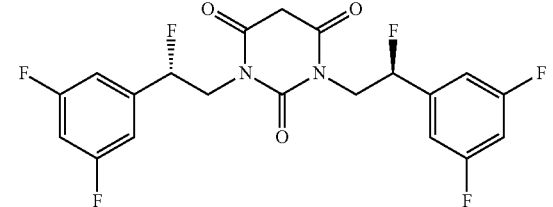
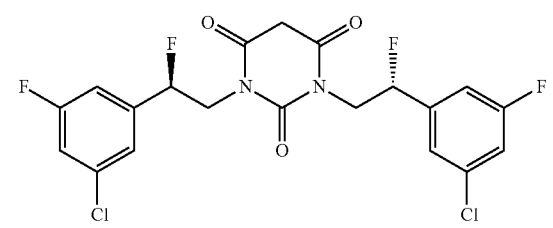
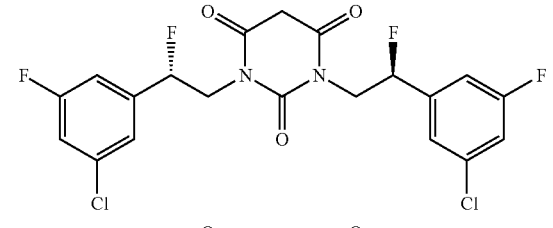
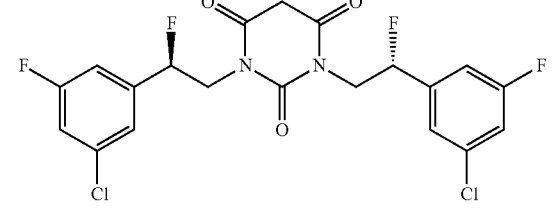
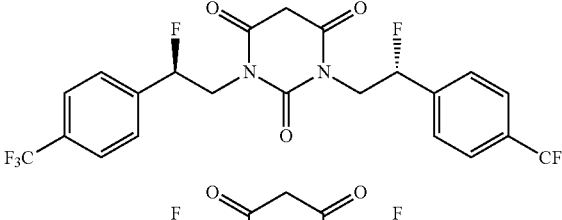
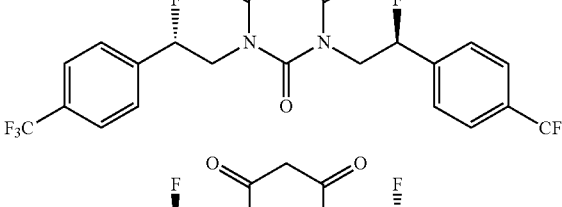
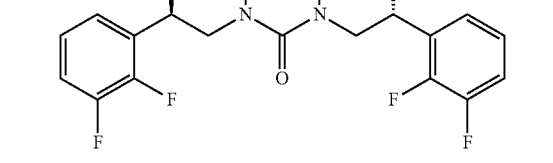
62
-continued
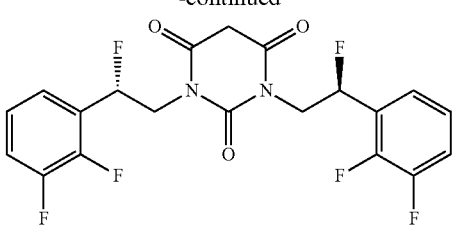
or a pharmaceutically acceptable salt thereof.
In some embodiments, the provided compound has a structure depicted in any one of the following formulae:
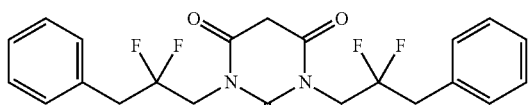
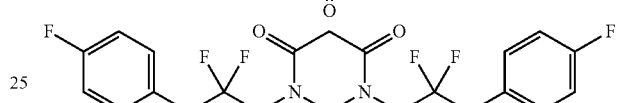
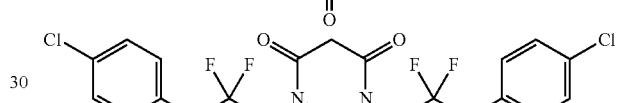
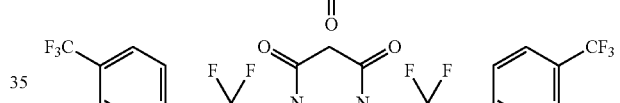
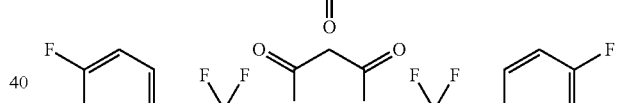
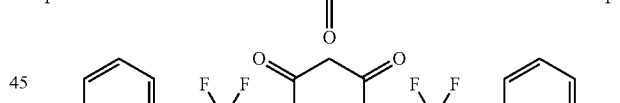
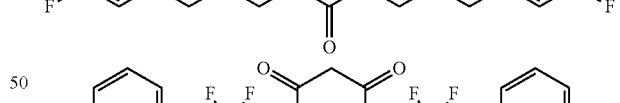
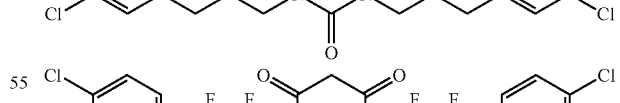
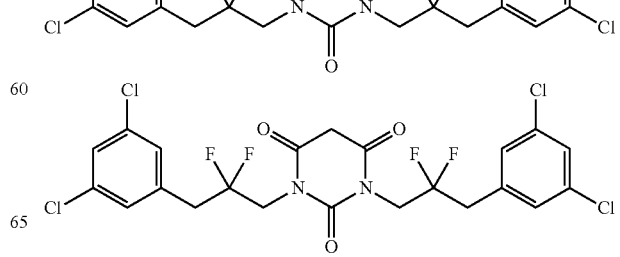

-continued
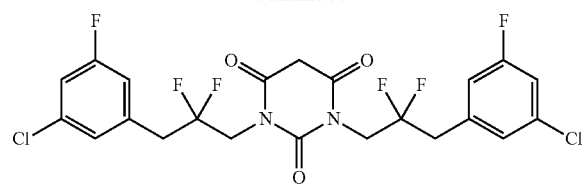
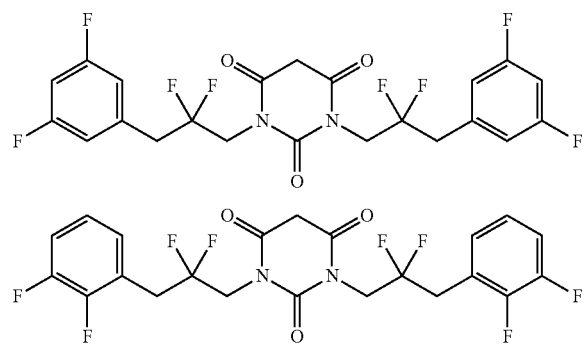
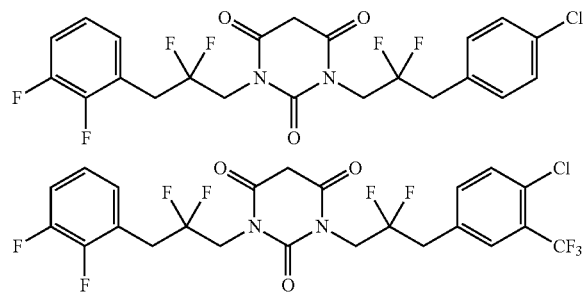
or a pharmaceutically acceptable salt thereof.
In some embodiments, the provided compound has a structure depicted in any one of the following formulae:
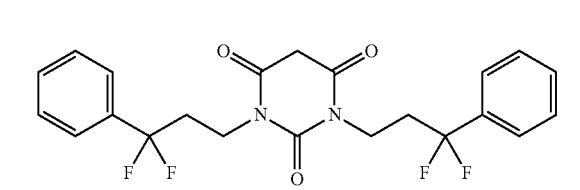
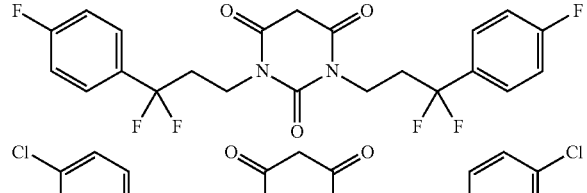
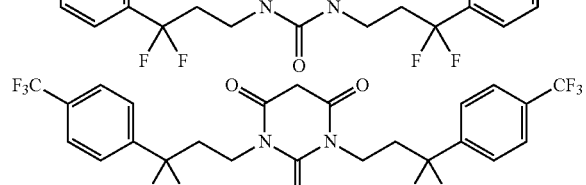
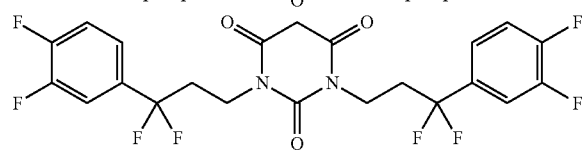
-continued
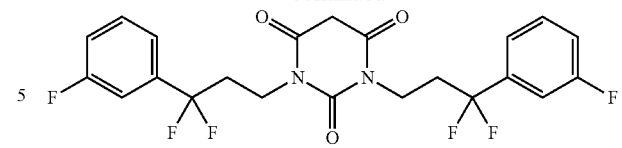
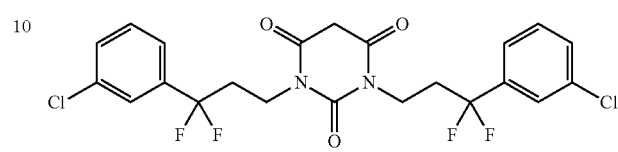
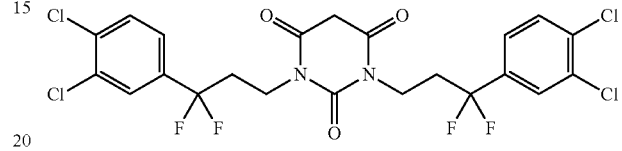
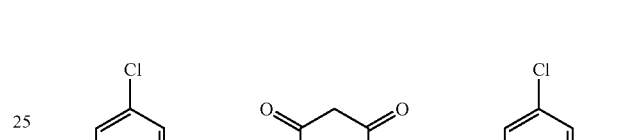
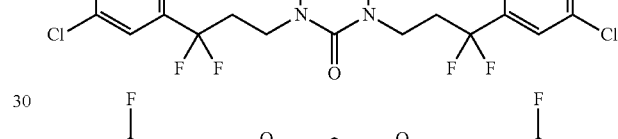
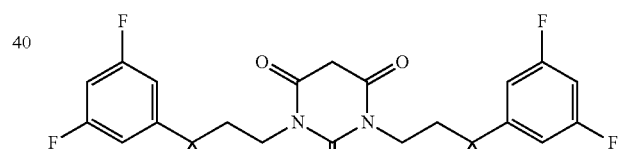
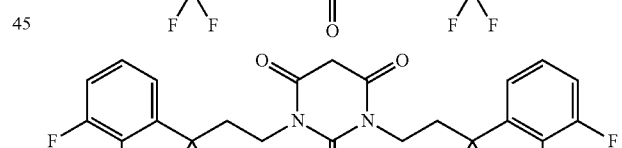
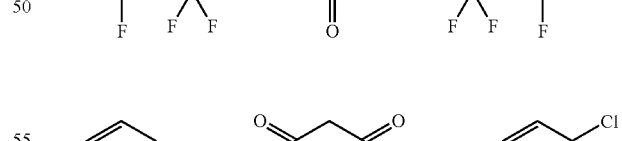
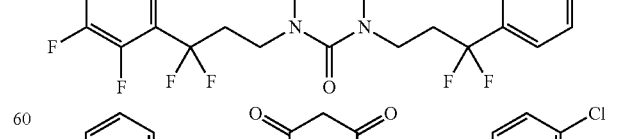
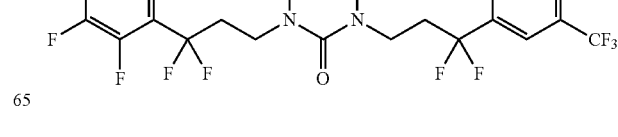
or a pharmaceutically acceptable salt thereof.

In some embodiments, the provided compound has a structure depicted in any one of the following formulae:
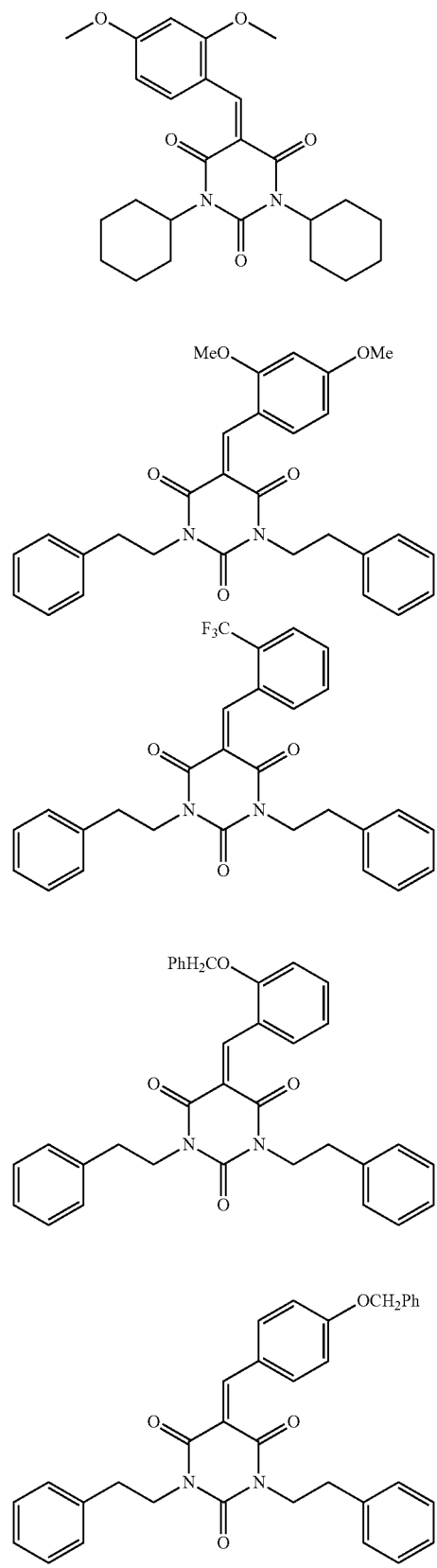
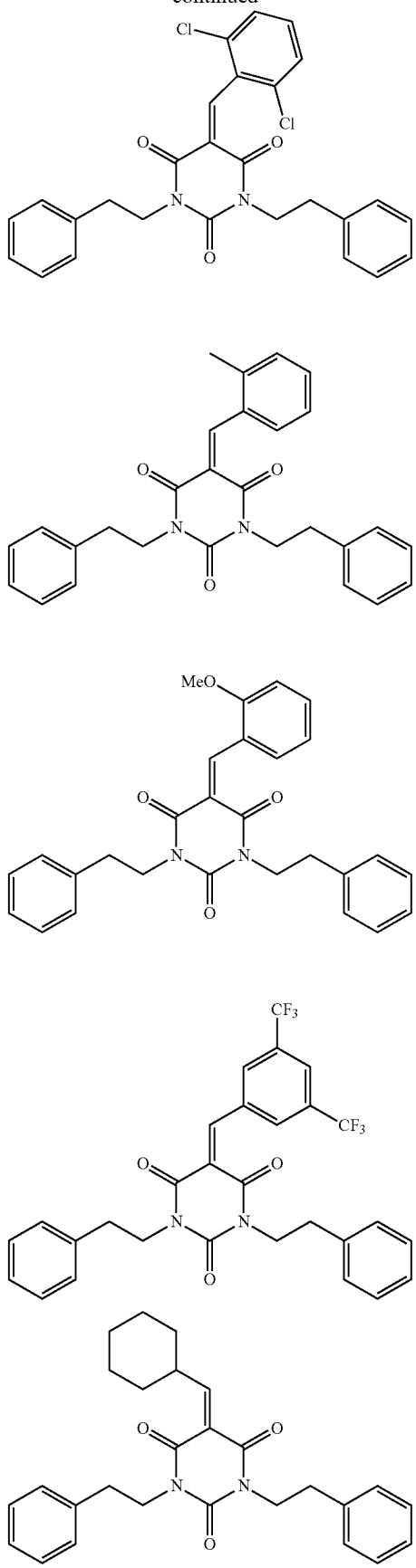

-continued

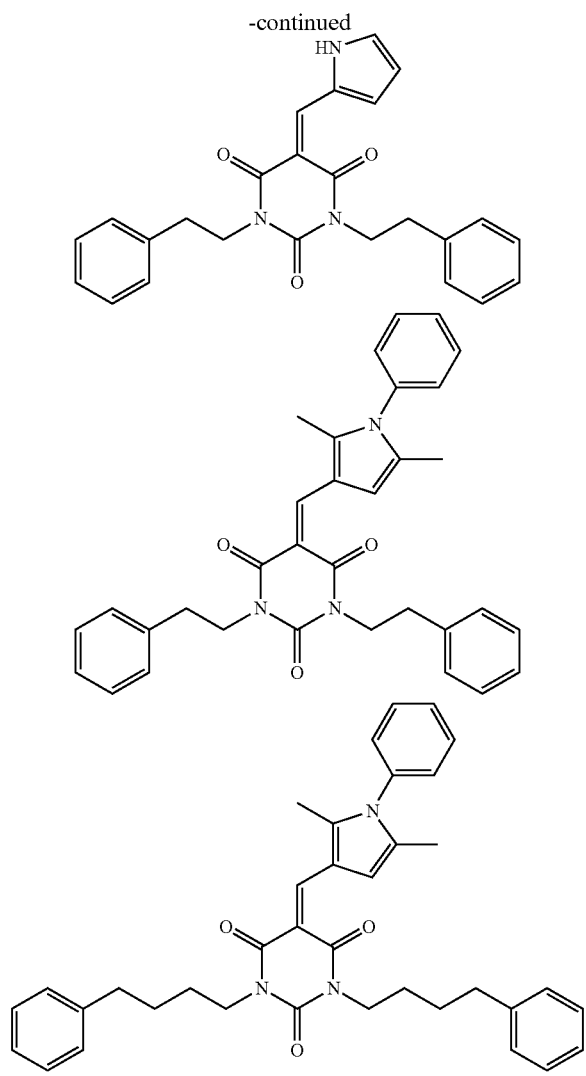

or a pharmaceutically acceptable salt thereof.

In some embodiments, total size of the compound does not exceed about 750 g/mol.

In some embodiments, a PYT compound for use in accordance with the present invention has the structure:

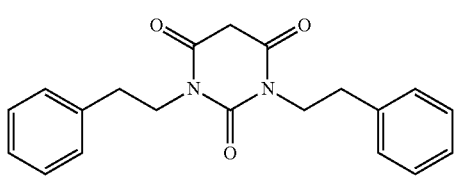 [SMILES: O=C1CC(=O)N(CCc2ccccc2)C(=O)N1CCc1ccccc1]

or a pharmaceutically acceptable salt thereof.

In some embodiments, a PYT compound according to the present invention shows a maximum tolerated dose (e.g., when tested in a model organism such as a mouse) of at least about 50, 60, 70, 80, 90, 100, 110, 120, 130, 140, or 150 mg/kg IP. In some embodiments, a PYT compound according to the present invention shows a maximum tolerated dose of greater than about 150 mg/kg IP. In certain embodiments, a PYT compound according to the present invention shows a maximum tolerated dose of at least about 100 mg/kg IP.

In some embodiments, a PYT compound according to the present invention has a therapeutic index of at least about five. In some embodiments, a PYT compound according to the present invention has a therapeutic index of about 6, 7, 8, 9, 10, 11, 12, 13, 14, 15, 16, 17, 18, 19, or 20. In some embodiments, a PYT compound according to the present invention has a therapeutic index of about 25, 30, 35, 40, 45, or 50. In certain embodiments, a PYT compound according to the present invention has a therapeutic index of about ten.

In some embodiments, a PYT compound according to the present invention is characterized by excellent oral availability. In some embodiments, a PYT compound according to the present invention shows about 70%, 80, or 90% oral availability. In some embodiments, a PYT compound according to the present invention shows about 91%, 92%, 93%, 94%, 95%, 96%, 97%, 98%, or 99% oral availability. In certain embodiments, a PYT compound according to the present invention shows about 100% oral availability.

In some embodiments, a PYT compound according to the present invention is characterized by a metabolic half life of about 24 h. In some embodiments, a PYT compound according to the present invention is characterized by a metabolic half life of less than about 24 h. In some embodiments, a PYT compound according to the present invention is characterized by a metabolic half life of about 12 h. In some embodiments, a PYT compound according to the present invention is characterized by a metabolic half life of about 10 h. In some embodiments, a PYT compound according to the present invention is characterized by a metabolic half life of about 8 h. In some embodiments, a PYT compound according to the present invention is characterized by a metabolic half life of about 2, 3, 4, 5, 6, 7, 8, 9, 10, 11, or 12 h. In some embodiments, a PYT compound according to the present invention is characterized by a metabolic half life of about 20, 30, 40, 50, 60, 70, 80, 90, or 100 minutes. In some embodiments, a PYT compound according to the present invention is characterized by a metabolic half life of at least about 45 minutes.

In some embodiments, a PYT compound according to the present invention shows good blood brain barrier penetration in that a blood:brain concentration ratio of at least about 10:1 is observed. In some embodiments, a PYT compound according to the present invention shows a blood brain barrier penetration in that a blood:brain concentration ratio of about 9:1, 8:1, 7:1, 6:1, 5:1, 4:1, 3:1, 2:1, or 1:1 is observed. In certain embodiments, a blood:brain concentration ratio of about 3:1 is observed.

In some embodiments, a PYT compound according to the present invention is characterized by good tissue penetration such that intraperitoneal administration of 50 mg/kg achieves blood concentrations in the range of about 100, 125, 150, 175 or 200 µM, and/or brain concentrations in the range of 30, 40, 50, 60, or 70 µM (e.g., in a model organism such as a mouse). In some embodiments, intraperitoneal administration of about 60 mg/kg achieves a blood concentration of about 150 micromolar, and/or a brain concentration of about 50 micromolar. In some embodiments, intraperitoneal administration of about 50 mg/kg achieves a blood concentration of about 150 micromolar, and/or a brain concentration of about 50 micromolar. In some embodiments, intraperitoneal administration of about 40 mg/kg achieves a blood concentration of about 150 micromolar, and a brain concentration of about 50 micromolar. In some embodiments, intraperitoneal administration of less than about 40 mg/kg achieves a blood concentration of about 150 micromolar, and/or a brain concentration of about 50 micromolar. In some embodiments, intraperitoneal administration of about 10, 20, 30, 40, 50, 60, 70, 80, 90, or 100 mg/kg achieves a blood concentration of about 150 micromolar, and/or a brain concentration of about 50 micromolar.

In some embodiments, a PYT compound according to the present invention is characterized by good tissue penetration such that oral administration of 50 mg/kg achieves blood concentrations in the range of about 100, 125, 150, 175 or 200 micromolar, and/or brain concentrations in the range of 30, 40, 50, 60, or 70 micromolar (e.g., in a model organism such as a mouse). In some embodiments, oral administration of about 60 mg/kg achieves a blood concentration of about 150 micromolar, and/or a brain concentration of about 50 micromolar. In some embodiments, oral administration of about 50 mg/kg achieves a blood concentration of about 150 micromolar, and/or a brain concentration of about 50 micromolar. In some embodiments, oral administration of about 40 mg/kg achieves a blood concentration of about 150 micromolar, and a brain concentration of about 50 micromolar. In some embodiments, oral administration of less than about 40 mg/kg achieves a blood concentration of about 150 micromolar, and/or a brain concentration of about 50 micromolar. In some embodiments, oral administration of about 10, 20, 30, 40, 50, 60, 70, 80, 90, or 100 mg/kg achieves a blood concentration of about 150 micromolar, and/or a brain concentration of about 50 micromolar.

In some embodiments, a PYT compound according to the present invention exhibits $EC_{50}$ values of less than about 30 µM. In some embodiments, a PYT compound according to the present invention exhibits $EC_{50}$ values of less than about 20 µM. In some embodiments, a PYT compound according to the present invention exhibits $EC_{50}$ values of less than about 10 µM. In some embodiments, a PYT compound according to the present invention exhibits $EC_{50}$ values of about 9, 8, 7, 6, 5, 4, 3, 2, or 1 µM. In certain embodiments, a PYT compound according to the present invention exhibits $EC_{50}$ values of less than about 1 µM. In certain embodiments, a PYT compound according to the present invention exhibits $EC_{50}$ values between 0.5 and 5.0 µM. In certain embodiments, a PYT compound according to the present invention exhibits an $EC_{50}$ value of about 2 µM.

Neurodegenerative Diseases Treated in Accordance with the Present Invention

Imbalances in protein homeostasis are often associated with protein misfolding and/or protein conformational changes that lead to protein aggregation and formation of protein inclusion bodies. Many neurodegenerative diseases, including the polyglutamine (polyQ)-repeat diseases, Alzheimer's disease, Parkinson's disease, prion diseases, and ALS, are characterized by the appearance of damaged and aggregated proteins, including huntingtin, polyQ proteins, amyloid A prion (PrP and Sup35) fibrils, and mutant SOD1 (Taylor et al., *Science.* 2002, 296(5575), 1991-5; Ross, C. A., *Neuron.* 1997, 19(6), 1147-50; Perutz, M. F., *Brain Res Bull.* 1999, 50(5-6), 467; and Kopito et al., *Nat Cell Bio.* 2000, 2(11), E207-9). The fact that such diverse proteins form aggregates in patients with distinct neurological diseases suggests that a common molecular etiology may contribute to the neuropathology in these diseases and that, perhaps, protein misfolding and the subsequent appearance of protein aggregates are early events that play a role in neuronal toxicity in multiple human neurological diseases (Orr, H. T., *Genes Dev.* 2001, 15(8), 925-32; Ikeda et al., *Nat Genet.* 1996, 13(2), 196-202; DiFiglia et al., *Science.* 1997, 277(5334), 1990-3; Davies et al., *Cell.* 1997, 90(3), 537-48; Koo et al., *Proc Natl Acad Sci USA.* 1999, 96(18), 9989-90).

One model for the molecular basis of these neurodegenerative diseases is that insoluble protein aggregates associate and interfere with the activity of other critical soluble cellular proteins, and that loss of function of these diverse proteins has serious negative consequences on cellular function. The affected proteins may include ubiquitin, components of the proteasome, components of the cytoskeleton, transcription factors (TBP (TATA binding protein), EYA (Eyes Absent protein), CBP (CREB binding protein), and molecular chaperones Hsc-70, Hsp-70, Hdj-1, and Hdj-2 (Davies et al., *Cell.* 1997, 90(3), 537-48; Ross, C. A., *Neuron.* 2002, 35(5), 819-22; Cummings et al., *Nat Genet.* 1998, 19(2) 148-54; Perez et al., *J Cell Biol.* 1998, 143(6), 1457-70; Kazantsev et al., *Proc Natl Acad Sci USA.* 1999, 96(20), 11404-9; Jana et al., *Hum Mol Genet.* 2001, 10(10), 1049-59; Nucifora et al., *Science.* 2001, 291(5512) 2423-8; and Suhr et al., *J Cell Biol.* 2001, 153(2), 283-94). Recent studies showed that TBP and CBP are irreversibly sequestered in polyQ/huntington aggregates, while the chaperone Hsp70 is transiently associated with the surface (Chai et al., *Proc Natl Acad Sci USA.* 2002, 99(14), 9310-5; Kim et al., *Nat Cell Biol.* 2002, 4(10), 826-31). Sequestration of CBP into polyglutamine aggregates is linked directly with loss of cellular function in neuronal cells, and overexpression of CBP suppressed polyQ toxicity (Nucifora et al., *Science.* 2001, 291(5512) 2423-8). Furthermore, expression of polyglutamine proteins in *C. elegans* causes other metastable proteins to lose function. Thus, a single aggregation-prone protein may be able to destabilize protein homeostasis in otherwise normal cells (Gidalevitz et al., *Science* 2006, 311(5766) 1471-1474). These studies indicate that the sequestration of essential soluble cellular proteins in insoluble protein aggregates could play a significant role in the neuropathology and neurotoxicity in ALS and related diseases.

It is also possible that the cellular mechanism(s) that remove misfolded or damaged proteins (Morimoto, R. I., *Cell.* 2002, 110(3), 281-4; Horwich et al., *Cell.* 1997, 89(4), 499-510; and Nollen et al., *J Cell Sci.* 2002, 115(Pt 14) 2809-16) are overwhelmed in neurodegenerative diseases due to the presence of abundant protein aggregates. The activity of molecular chaperones is one of the most important mechanisms to prevent and/or rescue protein misfolding and aggregation. Molecular chaperones are a large and diverse protein family which includes Hsp104, Hsp90, Hsp70, dnaJ (Hsp40), immunophilins (Cyp40, FKBP), Hsp60 (chaperonins), the small heat shock proteins, and components of the steroid aporeceptor complex (p23, Hip, Hop, Bag1) (Gething, M. J., *Nature.* 1997, 388(6640) 329, 331; Bakau, B., Amsterdam: Harwood Academic Publishers. 1999, (690). Molecular chaperones ensure proper protein folding by preventing hydrophobic surfaces from interacting with each other, by enhancing protein refolding, and when necessary, by stimulating protein degradation to remove misfolded proteins that tend to aggregate (Horwich et al., *Cell.* 1997, 89(4), 499-510; Bakau, b., Amsterdam: Harwood Academic Publishers. 1999, 690; Schroder et al., *Embo J.* 1993, 12(11), 4137-44; Parsell et al., *Nature* 1994, 372(6505), 475-8; Hartl, F. U., *Nature.* 1996, 381(6583) 571-9; and Morimoto et al., *Nat. Biotechnol.* 1998, 16(9), 833-8). Accordingly, overexpression of molecular chaperones can suppress the toxicity of mutant huntingtin, α-synuclein, and SOD1 (Sakahira at al., *Proc. Natl. Acad. Sci. USA.* 2002, 99 Suppl. 4, 6412-8; Stenoien et al., *Hum. Mol. Genet.* 1999, 8(5), 731-41; Warrick et al., *Nat. Genet.* 1999, 23(4), 425-8; Carmichael et al., *Proc. Natl. Acad. Sci. USA.* 2000, 97(17), 9701-5; Takeuchi et al., *Brain Res.* 2002, 949(1-2), 11-22; Auluck et al., *Science* 2002, 295(5556), 865-8; and Bailey et al., *Hum. Mol Genet.* 2002, 11(5), 515-23). Recently, non-chaperone proteins were identified that also suppress toxicity associated with protein aggregation (Kazemi-Esfarjani et al., *Science* 2000, 287(5459), 1837-40; and Kazemi-Esfarjani et al., *Hum. Mol. Genet.* 2002, 11(21), 2657-72).

The chaperone system is a highly appealing therapeutic target, because multiple small molecular weight modulators of chaperone activity have already been identified, two of which are active in a mouse model of ALS (Westerheide et al., *J. Biol. Chem.* 2005, 280(39), 33097-100; Kieran et al., *Nat. Med.* 2004, 10(4), 402-5; and Traynor et al., *Neurology.* 2006, 67(1), 20-7). Accordingly, recent analyses identified protein folding/misfolding and protein aggregation as a relevant therapeutic target for neurodegenerative diseases (Pasinelli et al., *Nat. Rev. Neurosci.* 2006, 7(9), 710-23; Lansbury et al., *Nature.* 2006, 443(7113), 774-9; Rubinsztein et al., *Nature* 2006, 443(7113), 780-6).

Methods of Using PYT Compounds in Accordance with the Present Invention

The present invention encompasses the recognition that provided PYT compounds can be effective in treating patients with amyotrophic lateral sclerosis (ALS) or other neurodegenerative diseases characterized by the presence of aberrant protein aggregates. Without wishing to be bound by any particular theory or mechanism of action, methods of the invention are useful in inhibiting or reversing abnormal protein aggregation or reducing the toxicity of protein aggregation (e.g., SOD1 or TDP-43). The invention provides methods for treating a subject suffering from or susceptible to ALS or other neurodegenerative disease including the step of administering to the subject a therapeutically effective amount of a provided PYT compound or a pharmaceutical composition thereof. In certain embodiments, the subject is a transgenic mouse. In certain embodiments, the subject is an adult human. In certain embodiments, the ALS being treated is familial ALS. In certain embodiments, the ALS being treated is sporadic ALS.

In some embodiments, the neurodegenerative disease characterized by the presence of aberrant protein aggregates is Parkinson's disease (PD), diffuse Lewy body disease (DLBD), multiple system atrophy (MSA), and pantothenate kinase-associated neurodegeneration (PANK), Huntington's Disease (HD), prion diseases (e.g., Creutzfeldt Jakob disease), Alzheimer's Disease (AD), or frontotemporal lobar degeneration.

In some embodiments, the invention provides a method comprising steps of administering to a subject suffering from or susceptible to ALS an effective amount of a provided PYT compound, such that the severity or incidence of one or more symptoms of ALS is reduced, or its onset is delayed. In some embodiments, a provided PYT compound is administered in the form of a salt or pharmaceutically acceptable composition thereof. In certain embodiments, a provided PYT compound is administered in accordance with the present invention to subjects suffering from or susceptible to a neurodegenerative disease, disorder, or condition in a form or composition and/or according to a regimen useful in the treatment of ALS. In certain embodiments, the subject suffering from or susceptible to ALS is a human from about 40 to about 85 years of age.

In some embodiments, the ALS being treated is characterized by the presence of abnormal protein aggregates such as, for example, SOD1 protein aggregates or TDP-43 protein aggregates. Exemplary such SOD1 protein aggregates include G93A SOD1 and G85R SOD1 protein aggregates. Without wishing to be bound by any particular theory, use of provided PYT compound in the treatment of ALS may reduce or delay the formation of such protein aggregates.

In some embodiments, a provided PYT compound is administered once a day. In some embodiments, a provided PYT compound is administered two, three, four, or five times a day. In some embodiments, a provided PYT compound is administered every other day. In some embodiments, a provided PYT compound is administered every two days. In some embodiments, a provided PYT compound is administered every three days. In some embodiments, a provided PYT compound is administered every four days. In some embodiments, a provided PYT compound is administered every five days. In some embodiments, a provided PYT compound is administered every six days. In some embodiments, a provided PYT compound is administered once a week. In some embodiments, a provided PYT compound is administered at intervals as instructed by a physician for the duration of the life of the subject being treated. In certain embodiments, a provided PYT compound is administered as many times a day as necessary to provide a therapeutically effective amount of a provided PYT compound to treat a subject suffering from or susceptible to ALS.

In some embodiments, the subject suffering from or susceptible to ALS is a mammal. In some embodiments, the subject suffering from or susceptible to ALS is a rodent, such as a rat or mouse, for example, a mouse model of ALS. In certain embodiments, the subject suffering from or susceptible to ALS is a human. In certain embodiments, the human is about 20, 30, 40, 50, 60, 70, 80, 90, or 100 years of age. In certain embodiments, the human is between 40 and 85 years of age.

The efficacy of a provided PYT compound in the treatment of neurodegenerative diseases according to the present invention may be evaluated and followed using any method known in the medical arts. The treatment of ALS may be evaluated, for example, by physical examination, laboratory testing, imaging studies, electrophysiological studies, etc. In some embodiments, the treatment of ALS may be evaluated by monitoring the subject being treated. In some embodiments, the subject is monitored by monitoring motor function. In some embodiments, the subject is monitored by monitoring body weight. In some embodiments, the subject is monitored by monitoring survival time. In some embodiments, the subject is monitored one, two, three, four, or five times a day. In some embodiments, the subject is monitored one, two, three, four or five times a week. In some embodiments, the subject is monitored twice a week. In some embodiments, monitoring is continuous. In some embodiments, monitoring occurs for the duration of the subject's life. In certain embodiments, the subject is monitored one, two, or three times a day by monitoring body weight. In some embodiments, the subject is a human and is monitored using any of the methods known in the medical arts suitable for monitoring humans suffering from or susceptible to a neurodegenerative disease such as ALS. Exemplary such methods of monitoring include monitoring neurological function, respiratory function (e.g., pulmonary function test), muscle strength, speech, swallowing function, etc. In some embodiments, monitoring may comprise checking for signs of toxicity; in certain embodiments, toxicity is measured using any of the methods previously developed to measure toxicity of a provided PYT compound in patients being treated for schizophrenia.

Dosages of a provided PYT compound utilized in accordance with the present invention may vary with the form of administration and/or with the particular subject being treated for ALS. In general, a provided PYT compound is most desirably administered at a concentration level that will afford effective results without causing any harmful or deleterious side-effects. In some embodiments, a provided PYT compound is administered in doses ranging from about 0.5 to about 500 mg/kg/day. In some embodiments, a provided PYT compound is administered in doses ranging from about 5 to about 100 mg/kg/day. In some embodiments, a provided PYT compound is administered in doses ranging from about 10 to about 100 mg/kg/day. In some embodiments, a provided PYT compound is administered in doses ranging from about 20 to about 100 mg/kg/day. In some embodiments, a provided PYT compound is administered in doses ranging from about 30 to about 100 mg/kg/day. In some embodiments, a provided PYT compound is administered in doses ranging from about 40 to about 100 mg/kg/day. In some embodiments, a provided PYT compound is administered in doses ranging from about 50 to about 100 mg/kg/day. In some embodiments, a provided PYT compound is administered in doses ranging from about 60 to about 100 mg/kg/day. In some embodiments, a provided PYT compound is administered in doses ranging from about 70 to about 100 mg/kg/day. In some embodiments, a provided PYT compound is administered in doses ranging from about 80 to about 100 mg/kg/day. In some embodiments, a provided PYT compound is administered in doses ranging from about 90 to about 100 mg/kg/day. In some embodiments, a provided PYT compound is administered in doses of less than about 20 mg/day. In some embodiments, a provided PYT compound is administered in doses ranging from about 1 mg/kg/day to about 50 mg/kg/day. In some embodiments, a provided PYT compound is administered in doses ranging from about 1 mg/kg/day to about 40 mg/kg/day. In some embodiments, a provided PYT compound is administered in doses ranging from about 1 mg/kg to about 30 mg/kg/day. In some embodiments, a provided PYT compound is administered in doses ranging from about 1 mg/kg/day to about 20 mg/kg/day. In some embodiments, a provided PYT compound is administered in doses ranging from about 1 mg/kg/day to about 10 mg/kg/day. In some embodiments, a provided PYT compound is administered in doses ranging from about 10 mg/kg/day to about 50 mg/kg/day. In some embodiments, a provided PYT compound is administered in doses ranging from about 10 mg/kg/day to about 40 mg/k/day. In some embodiments, a provided PYT compound is administered in doses ranging from about 10 mg/kg/day to about 30 mg/kg/day. In some embodiments, a provided PYT compound is administered in doses ranging from about 10 mg/kg/day to about 20 mg/kg/day. In some embodiments, a provided PYT compound is administered in doses ranging from about 20 mg/kg/day to about 50 mg/kg/day. In some embodiments, a provided PYT compound is administered in doses ranging from about 20 mg/kg/day to about 40 mg/kg/day. In some embodiments, a provided PYT compound is administered in doses ranging from about 20 mg/kg/day to about 30 mg/kg/day. In some embodiments, a provided PYT compound is administered in doses ranging about 25 mg/kg/day to about 50 mg/kg/day. In some embodiments, a provided PYT compound is administered in doses ranging about 30 mg/kg/day to about 50 mg/kg/day. In some embodiments, a provided PYT compound is administered in doses ranging from about 30 mg/kg/day to about 40 mg/kg/day. In some embodiments, a provided PYT compound is administered in doses ranging from about 40 mg/kg/day to about 50 mg/kg/day. In some embodiments, a provided PYT compound is administered in doses less than about 10 mg/kg/day. In some embodiments, a provided PYT compound is administered in doses less than about 5 mg/kg/day. In some embodiments, a provided PYT compound is administered in doses less than about 2 mg/kg/day. In some embodiments, a provided PYT compound is administered in doses less than about 1 mg/kg/day. In some embodiments, a provided PYT compound is administered in doses less than about 0.1 mg/kg/day. In some embodiments, a provided PYT compound is administered in doses less than about 0.01 mg/kg/day. In some embodiments, a provided PYT compound is administered in doses less than about 0.001 mg/kg/day. In some embodiments, a provided PYT compound is administered in doses of about 0.1, 0.2, 0.3, 0.4, 0.5, 0.6, 0.7, 0.8, 0.9, or 1.0 mg/kg/day. In some embodiments, a provided PYT compound is administered in doses of about 0.01, 0.02, 0.03, 0.04, 0.05, 0.06, 0.07, 0.08, or 0.09 mg/kg/day. In some embodiments, a provided PYT compound is administered in doses ranging from about 0.1 mg/kg/day to about 1 mg/kg/day. In some embodiments, a provided PYT compound is administered in doses ranging from about 0.01 mg/kg/day to about 0.1 mg/kg/day. In some embodiments, a provided PYT compound is administered in doses ranging from about 0.001 mg/kg/day to about 0.01 mg/kg/day.

In some embodiments, a provided PYT compound is administered systemically in any one of the doses described herein and suitable for the treatment of ALS. Systemic administration may comprise enteral or parenteral administration. In certain embodiments, systemic administration comprises oral administration in solid or solution form in any one of the doses described herein. In certain embodiments, a provided PYT compound is administered parenterally in any one of the doses described herein. In certain embodiments, a provided PYT compound is administered intraperitoneally in any one of the doses described herein and the subject is a mouse or rat with ALS. In some embodiments, a provided PYT compound is administered orally and the subject is a human with ALS.

In some embodiments, the invention provides a method comprising steps of administering to a subject suffering from or susceptible to abnormal protein aggregation an amount of a provided PYT compound sufficient to reduce or delay such abnormal protein aggregation. In certain embodiments, reduction or inhibition of abnormal protein aggregation occurs in vivo in a subject with ALS or another neurodegenerative disease characterized by aberrant protein aggregation (e.g., Huntington's disease, prion disease, or Alzheimer's disease). In some embodiments, the subject is a mammal. In some embodiments, the subject is a mouse or rat. In some embodiments, the subject is a human. In certain embodiments, the human is about 20, 30, 40, 50, 60, 70, 80, 90, or 100 years of age. In some embodiments, abnormal protein aggregation comprises SOD1 protein aggregates. In certain embodiments, abnormal protein aggregation comprises G93A SOD1 protein aggregates. In certain embodiments, abnormal protein aggregation comprises G85R SOD1 protein aggregates. In certain embodiments, abnormal protein aggregation comprises TDP-43 protein aggregates.

In some embodiments, the invention provides a method comprising the steps of administering to a cell in vitro an amount of a provided PYT compound effective to inhibit or reverse the toxic effect of abnormal protein aggregation. In certain embodiments, contact occurs in vitro, and the cell is derived from a mammalian cell line. In certain embodiments, contact occurs in vitro, and the cell is derived from a PC12 cell line. In certain embodiments, PC12 cells may additionally contain a detectable moiety to measure the extent of inhibition of aggregation. In certain embodiments, a detectable moiety is associated with a protein (e.g., a type of SOD1 protein, such as G93A SOD1 and/or G85R SOD1, or a type of TDP-43 protein). In certain embodiments, the detectable moiety is a flourescent moiety (e.g., a YFP tag). In some embodiments, the detectable moiety is a phosphorescent moiety, a radiolabel, or any other detectable moiety known in the art, and may be detected using any of the methods known in the art. In some embodiments, the detectable moiety may be detected using a high content microscopy system to allow for high-throughput screening. In certain embodiments, the detectable moiety allows for the measurement of cell viability.

In some embodiments, the invention provides a method comprising the steps of administering to a cell in vitro an amount of a provided PYT compound effective to protect against aggregated SOD1. In certain embodiments, protection occurs in vitro in a cell culture. In some embodiments, compounds of the invention are contacted with a cell line in vitro and the cell line is a mammalian cell line. In certain embodiments, the cell line is the PC12 cell line. In some embodiments, cells are associate with a detectable moiety such as those described above. In some embodiments, cells contain a protein labeled with a detectable moiety. In certain embodiments, the protein is SOD1 (e.g., G93A SOD1 and/or G85R SOD1) and the detectable moiety is a fluorescent moiety. In certain embodiments, the detectable moiety is a flourescent moiety (e.g., a YFP tag) that may be detected using a high content microscopy system to allow for high-throughput screening. In some embodiments, the detectable moiety is a phosphorescent moiety, an epitope, radiolabel, or any other detectable moiety known in the art, and may be detected using any of the methods known in the art. In certain embodiments, the detectable moiety allows for the measurement of cell viability.

In some embodiments, the invention provides a method comprising the steps of administering to a cell in vitro an amount of a provided PYT compound effective to modulate proteasome function. In certain embodiments, the cell is derived from a mammalian cell line. In some embodiments, the cell is derived from a PC12 cell line or a HeLa cell line. In certain embodiments, the cells contain a detectable moiety to measure the extent to which proteasome activity is inhibited. In certain embodiments, the protein is SOD1 (e.g., G93A SOD1 and/or G85R SOD1) and the detectable moiety is a fluorescent moiety. In certain embodiments, the protein is TDP-43. In certain embodiments, the detectable moiety is a flourescent moiety such as a Ubi-YFP tag. In some embodiments, the detectable moiety is a Ubi-YFP tag and is detectable by fluorescence microscopy. In some embodiments, the detectable moiety is a phosphorescent moiety, an epitope, a radiolabel, or any other detectable moiety known in the art, and may be detected using any of the methods known in the art. In some embodiments, the detectable moiety may be detected using a high content microscopy system to allow for high-throughput screening. In certain embodiments, cell viability is measured.

In some embodiments, the present invention provides systems, methods, and/or reagents to characterize provided PYT compounds and compositions. In some embodiments, the present invention provides assays to identify forms of provided PYT compounds and compositions that protect against protein aggregate-induced cytotoxicity. In certain embodiments, the assays are cell protection assays. Cell protection assays may used to identify provided PYT compounds and compositions that protect cells from the cytotoxic effects of aberrant protein aggregation. In some embodiments, the assays are protein aggregation inhibition assays that are used to identify provided PYT compounds and compositions that inhibit protein aggregation in a cell or in vitro.

In some embodiments, the present invention provides a method of identifying provided PYT compounds and compositions that protect against protein aggregate-induced cytotoxicity comprising contacting a cell expressing SOD1, TDP-43, or another protein susceptible to aggregation with a test compound, incubating the cell with the test compound under suitable conditions for an amount of time sufficient to observe a protective effect against protein aggregate-induced cytotoxicity, and then measuring viability in the cells treated with the test compound. In some embodiments, the extent of protein aggregation-induced cytotoxicity is measured by determining the level of a detectable moiety (e.g., a fluorescent moiety) in the cell.

In certain embodiments, the expressed protein in the cell used in the assay is a mutant SOD1 protein. In certain embodiments, the expressed protein the cell used in the assay is a mutant TDP-43 protein. In some embodiments, the expressed protein is SOD1 protein associated with a detectable moiety. In certain embodiments, the expressed protein is a fluorescently tagged mutant SOD1 protein, and the flourescent moiety is a YFP tag. In some embodiments, the detectable moiety is a phosphorescent moiety, epitope, or radiolabel. In some embodiments, the detectable moiety is any suitable detectable moiety known to those or ordinary skill in the art and may be detected using any method known in the art. In some embodiments, the detectable moiety is a fluorescent tag (e.g., a YFP tag) that can be detected with a high content microscopy system. In some embodiments, the high content microscopy system detects cell viability and facilitates high-throughput screening of a plurality of provided PYT compounds.

Cells may be pre-treated with an agent that modulates the expression of a protein of interest (e.g., SOD1, TDP-43) in the assay. The agent may, for instance, induce the expression of a gene responsible for the protein of interest (e.g., doxycycline-inducible promoter). In some embodiments, cells may also be treated with an agent that modulates proteasome activity. In certain embodiments, the agent may be a proteasome inhibitor (e.g., MG132). In some embodiments, cell viability of cells pre-treated with an agent described herein is measured using methods described above.

In certain embodiments, the time of incubation of a cell with a provided PYT compound or composition ranges from approximately 1 minute to approximately 1 week. In some embodiments, the time of incubation ranges from approximately 5 minutes to approximately 1 week. In some embodiments, the time of incubation ranges from approximately 30 minutes to approximately 2 days. In some embodiments, the time of incubation ranges from approximately 30 minutes to approximately 1 day. In some embodiments, the time of incubation ranges from approximately 1 hour to approximately 1 day. In some embodiments, the time of incubation ranges from approximately 1 hour to approximately 18 hours. In some embodiments, the time of incubation ranges from approximately 1 hour to approximately 12 hours. In some embodiments, the time of incubation ranges from approximately 1 hour to approximately 6 hours. In some embodiments, the time of incubation ranges from approximately 1 hour to approximately 3 hours. In some embodiments, the time of incubation is approximately 6 hours. In some embodiments, the time of incubation is approximately 12 hours. In some embodiments, the time of incubation is approximately 18 hours. In some embodiments, the time of incubation is approximately 24 hours.

In certain embodiments, the temperature during incubation of a cell with a provided PYT compound or composition ranges from approximately 20° C. to approximately 45° C. In certain embodiments, the temperature ranges from approximately 20° C. to approximately 40 OC. In certain embodiments, the temperature ranges from approximately 25° C. to approximately 40° C. In certain embodiments, the temperature ranges from approximately 30° C. to approximately 40° C. In certain embodiments, the temperature is approximately 30° C. In certain embodiments, the temperature is approximately 37° C.

Provided PYT compounds or compositions that are active in the above-mentioned assay could theoretically protect against abnormal protein aggregate-induced cytotoxicity through a number of biological mechanisms. The present invention additionally provides methods to screen for provided PYT compounds or compositions that protect against abnormal protein-aggregate induced cytotoxicity wherein the protein aggregation is inhibited in a non-specific manner.

Provided PYT compounds or compositions which inhibit aberrant protein aggregation can be identified using methods similar to those described above in the aforementioned cytotoxicity assay. In some embodiments, the present invention provides a method of identifying provided PYT compounds or compositions that inhibit aberrant protein aggregation comprising contacting a cell expressing SOD1 or other protein susceptible to aggregation with a provided PYT compound or composition, incubating the cell with the compound or composition under suitable conditions, and then measuring the extent of protein aggregation in the cells treated with the provided PYT compound or composition as compared to a control. In certain embodiments, the extent of inhibition of protein aggregation is measured by staining the protein aggregates with a detectable stain (e.g., Image-iT plasma membrane dye). In some embodiments, the detectable stain is detected using a scanning device (e.g., Cellomics Arrayscan). In certain embodiments, the protein aggregates are detected using any method of detecting protein aggregates known in the art.

Provided PYT compounds and compositions identified using the above-mentioned assays may be further examined using biological assays to guide structure-activity relationship (SAR) analyses of the identified compounds. Biological assays and SAR analyses are known to those of skill in the art.

General Methods of Providing PYT Compounds

Provided compounds may be prepared by methods known to one of ordinary skill in the art and/or by methods illustrated in Schemes 1-3, below. Unless otherwise noted, all variables are as defined above and in classes and subclasses herein.

In the Schemes below, where a particular protecting group, leaving group, or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5th Edition, John Wiley & Sons, 2001, *Comprehensive Organic Transformations*, R. C. Larock, 2nd Edition, John Wiley & Sons, 1999, and *Protecting Groups in Organic Synthesis*, T. W. Greene and P. G. M. Wuts, 3rd edition, John Wiley & Sons, 1999, the entirety of each of which is hereby incorporated herein by reference.

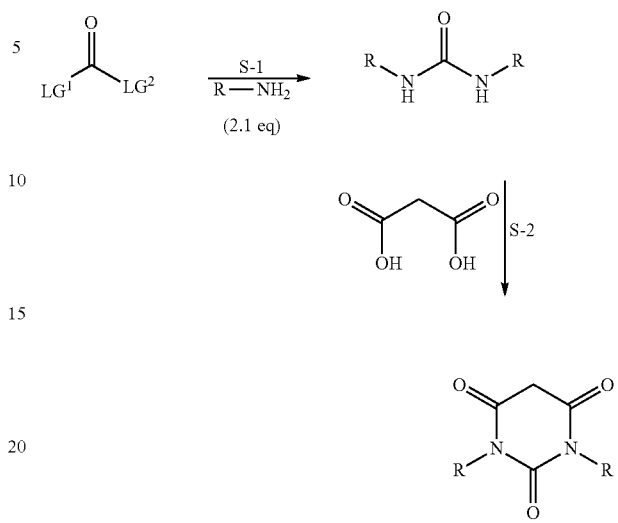

As depicted in Scheme 1 above, provided PYT compounds are synthesized via the di-addition of an amine to an activated carbonyl compound (see step S-1) to furnish a urea-type intermediate. The crude intermediate is subsequently added to a diacid (see step S-2) under acidic conditions (e.g., a mixture of acetic acid and acetic anhydride) to form a PYT compound. Parallel synthesis using the above-described method affords quick access to a variety of PYT compounds.

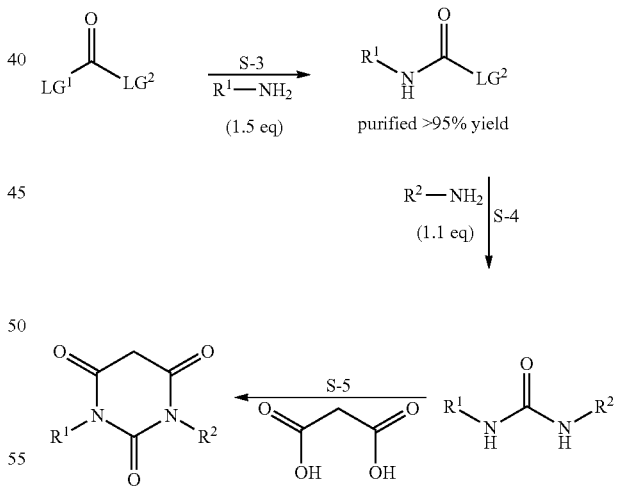

Scheme 2 above illustrates the iterative addition of two different amines to the activated carbonyl group. The mono-addition of a first amine (see step S-3) affords an intermediate that can be purified and subsequently reacted with a second amine (see step S-4) to afford a urea-type mixed intermediate. Addition of a diacid (see step S-5) affords the provided PYT compounds. Parallel synthesis using the above-described method affords quick access to a variety of PYT compounds.

Scheme 3.

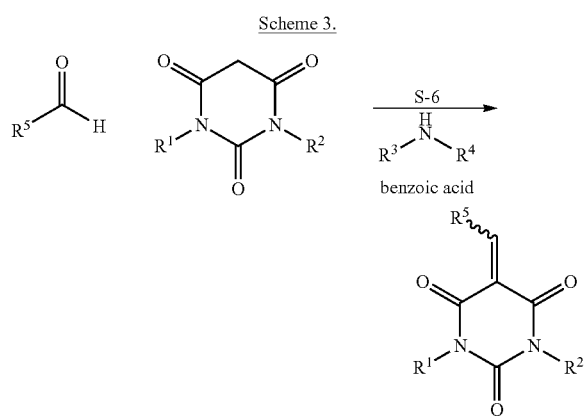

As illustrated in Scheme 3 above, provided PYTs may undergo a Knoevenagel condensation reaction with an aldehyde in the presence of a secondary amine and benzoic acid to afford modified PYTs containing $sp^2$-hybridized moieties.

For each of the aforementioned Schemes, it will be readily apparent to one of ordinary skill in the art that a variety of suitable reagents and reaction conditions may be employed to carry out the described syntheses.

Pharmaceutical Compositions

In another aspect, the present invention provides pharmaceutically compositions, which comprise a therapeutically effective amount of one or more of the inventive compounds, formulated together with one or more pharmaceutically acceptable carriers (additives) and/or diluents. As described in detail, the pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As set out herein, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. See, for example, Berge et al. (1977) "Pharmaceutical Salts", *J. Pharm. Sci.* 66:1-19; incorporated herein by reference.

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, compounds of the present invention may contain one or more acidic functional groups and, thus, may be capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. See, for example, Berge et al., supra.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and nonionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

In certain embodiments, a compound or pharmaceutical preparation is administered orally. In other embodiments, the compound or pharmaceutical preparation is administered intravenously. Alternative routs of administration include sublingual, intramuscular, and transdermal administrations.

When the compounds of the present invention are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

Preparations of compounds described herein may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration," and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level may depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject suffering from or susceptible to a neurodegenerative disease chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. Preferred chronic treatments involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 20 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six, or more sub-doses administered separately at appropriate intervals throughout the day, optionally, in unit dosage forms.

In some embodiments, a PYT compound as described herein may be administered neat. More commonly, however, it will be administered as part of a pharmaceutical formulation (composition) as described above.

Compounds described herein may be formulated for administration in any convenient way for use in human or veterinary medicine, by analogy with other pharmaceuticals.

According to the invention, compounds for treating neurodegenerative diseases, disorders, or conditions can be formulated or administered using methods that help the compounds cross the blood-brain barrier (BBB). The vertebrate brain (and CNS) has a unique capillary system unlike that in any other organ in the body. The unique capillary system has morphologic characteristics which make up the blood-brain barrier (BBB). The blood-brain barrier acts as a system-wide cellular membrane that separates the brain interstitial space from the blood.

Unique morphologic characteristics of the brain capillaries that make up the BBB include: (a) epithelial-like high resistance tight junctions which literally cement all endothelia of brain capillaries together, and (b) scanty pinocytosis or transendothelial channels, which are abundant in endothelia of peripheral organs. Due to the unique characteristics of the blood-brain barrier, hydrophilic drugs and peptides that readily gain access to other tissues in the body are barred from entry into the brain or their rates of entry and/or accumulation in the brain are very low.

In one aspect of the invention, compounds described herein that cross the BBB are particularly useful for treating neurodegenerative diseases. In one embodiment, compounds described herein that cross the BBB are particularly useful for treating amyotrophic lateral sclerosis (ALS). Therefore it will be appreciated by a person of ordinary skill in the art that some of the compounds of the invention might readily cross the BBB. Alternatively, the compounds of the invention can be modified, for example, by the addition of various substitutents that would make them less hydrophilic and allow them to more readily cross the BBB.

Various strategies have been developed for introducing those drugs into the brain which otherwise would not cross the blood-brain barrier. Widely used strategies involve invasive procedures where the drug is delivered directly into the brain. One such procedure is the implantation of a catheter into the ventricular system to bypass the blood-brain barrier and deliver the drug directly to the brain. These procedures have been used in the treatment of brain diseases which have a predilection for the meninges, e.g., leukemic involvement of the brain (U.S. Pat. No. 4,902,505, incorporated herein in its entirety by reference).

Although invasive procedures for the direct delivery of drugs to the brain ventricles have experienced some success, they are limited in that they may only distribute the drug to superficial areas of the brain tissues, and not to the structures deep within the brain. Further, the invasive procedures are potentially harmful to the patient.

Other approaches to circumventing the blood-brain barrier utilize pharmacologic-based procedures involving drug latentiation or the conversion of hydrophilic drugs into lipid-soluble drugs. The majority of the latentiation approaches involve blocking the hydroxyl, carboxyl and primary amine groups on the drug to make it more lipid-soluble and therefore more easily able to cross the blood-brain barrier.

Another approach to increasing the permeability of the BBB to drugs involves the intra-arterial infusion of hypertonic substances which transiently open the blood-brain barrier to allow passage of hydrophilic drugs. However, hypertonic substances are potentially toxic and may damage the blood-brain barrier.

Antibodies are another method for delivery of compositions of the invention. For example, an antibody that is reactive with a transferrin receptor present on a brain capillary endothelial cell, can be conjugated to a neuropharmaceutical agent to produce an antibody-neuropharmaceutical agent conjugate (U.S. Pat. No. 5,004,697, incorporated herein in its entirety by reference). The method is conducted under conditions whereby the antibody binds to the transferrin receptor on the brain capillary endothelial cell and the neuropharmaceutical agent is transferred across the blood brain barrier in a pharmaceutically active form. The uptake or transport of antibodies into the brain can also be greatly increased by cationizing the antibodies to form cationized antibodies having an isoelectric point of between about 8.0 to 11.0 (U.S. Pat. No. 5,527,527, incorporated herein in its entirety by reference).

A ligand-neuropharmaceutical agent fusion protein is another method useful for delivery of compositions to a host (U.S. Pat. No. 5,977,307, incorporated herein in its entirety by reference). The ligand is reactive with a brain capillary endothelial cell receptor. The method is conducted under conditions whereby the ligand binds to the receptor on a brain capillary endothelial cell and the neuropharmaceutical agent is transferred across the blood brain barrier in a pharmaceutically active form. In some embodiments, a ligand-neuropharmaceutical agent fusion protein, which has both ligand binding and neuropharmaceutical characteristics, can be produced as a contiguous protein by using genetic engineering techniques. Gene constructs can be prepared comprising DNA encoding the ligand fused to DNA encoding the protein, polypeptide or peptide to be delivered across the blood brain barrier. The ligand coding sequence and the agent coding sequence are inserted in the expression vectors in a suitable manner for proper expression of the desired fusion protein. The gene fusion is expressed as a contiguous protein molecule containing both a ligand portion and a neuropharmaceutical agent portion.

The permeability of the blood brain barrier can be increased by administering a blood brain barrier agonist, for example bradykinin (U.S. Pat. No. 5,112,596, incorporated herein in its entirety by reference), or polypeptides called receptor mediated permeabilizers (RMP) (U.S. Pat. No. 5,268,164, incorporated herein in its entirety by reference). Exogenous molecules can be administered to the host's bloodstream parenterally by subcutaneous, intravenous or intramuscular injection or by absorption through a bodily tissue, such as the digestive tract, the respiratory system or the skin. The form in which the molecule is administered (e.g., capsule, tablet, solution, emulsion) depends, at least in part, on the route by which it is administered. The administration of the exogenous molecule to the host's bloodstream and the intravenous injection of the agonist of blood-brain barrier permeability can occur simultaneously or sequentially in time. For example, a therapeutic drug can be administered orally in tablet form while the intravenous administration of an agonist of blood-brain barrier permeability is given later (e.g., between 30 minutes later and several hours later). This allows time for the drug to be absorbed in the gastrointestinal tract and taken up by the bloodstream before the agonist is given to increase the permeability of the blood-brain barrier to the drug. On the other hand, an agonist of blood-brain barrier permeability (e.g., bradykinin) can be administered before or at the same time as an intravenous injection of a drug. Thus, the term "co-administration" is used herein to mean that the agonist of blood-brain barrier and the exogenous molecule will be administered at times that will achieve significant concentrations in the blood for producing the simultaneous effects of increasing the permeability of the blood-brain barrier and allowing the maximum passage of the exogenous molecule from the blood to the cells of the central nervous system.

In other embodiments, compounds of the invention can be formulated as a prodrug with a fatty acid carrier (and optionally with another neuroactive drug). The prodrug is stable in the environment of both the stomach and the bloodstream and may be delivered by ingestion. The prodrug passes readily through the blood brain barrier. The prodrug preferably has a brain penetration index of at least two times the brain penetration index of the drug alone. Once in the central nervous system, the prodrug, which preferably is inactive, is hydrolyzed into the fatty acid carrier and the provided PYT compound or analog thereof (and optionally another drug). The carrier preferably is a normal component of the central nervous system and is inactive and harmless. The compound and/or drug, once released from the fatty acid carrier, is active. Preferably, the fatty acid carrier is a partially-saturated straight chain molecule having between about 16 and 26 carbon atoms, and more preferably 20 and 24 carbon atoms. Examples of fatty acid carriers are provided in U.S. Pat. Nos. 4,939,174; 4,933,324; 5,994,932; 6,107,499; 6,258,836; and 6,407,137, the disclosures of which are incorporated herein by reference in their entirety.

The administration of the agents of the present invention may be for either prophylactic or therapeutic purposes. When provided prophylactically, the agent is provided in advance of disease symptoms. The prophylactic administration of the agent serves to prevent or reduce the rate of onset of symptoms of ALS. When provided therapeutically, the agent is provided at (or shortly after) the onset of the appearance of symptoms of actual disease. In some embodiments, the therapeutic administration of the agent serves to reduce the severity and duration of the disease.

The function and advantage of these and other embodiments of the present invention will be more fully understood from the examples described below. The following examples are intended to illustrate the benefits of the present invention, but do not exemplify the full scope of the invention.

EXAMPLES

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims.

Example 1

Assays for Identification of Compounds that Protect Against Mutant SOD1-Induced Cytotoxicity High Throughput Assays Cultured cells are utilized to conduct high throughput assays for compounds that protect against mutant SOD1-induced cytotoxicity. Two assays are used: first, in the cytotoxicity protection assay, compounds are screened for their ability to protect cells from the cytotoxic effects of aggregated mutant SOD1, irrespective of mechanism of drug action. Second, in the protein aggregation assay, compounds are screened for their ability to reduce aggregation of mutant SOD1. The high throughput cytotoxicity protection assay is the primary screen and compounds active in the primary screen (and their analogs) move forward into the secondary screen for protein aggregation.

The high throughput cytotoxicity protection assay was carried out in PC12 cells that express mutant G93A SOD1 as a YFP fusion protein from a doxycycline-inducible promoter (Matsumoto et al., *J. Cell. Biol.* 2005, 171, 75). Several lines of evidence suggest that cytotoxicity of protein aggregates in ALS is due at least in part to inhibition of the proteasome (Bruijin et al. *Annu. Rev. Neurosci.* 2004, 27, 723-729; Cleveland et al. *Nat. Rev. Neurosci.* 2001, 2(11), 806). This idea was tested by examining the sensitivity of PC12 cells to SOD1 aggregates in the presence and absence of proteasome inhibitor MG132. PC12 cells expressing no SOD1, wild type SOD1, G85R SOD1 or G93A SOD1 were grown with or without MG132 (FIG. 1). Cells expressing no SOD1, wild type SOD1 and G85R SOD1 were relatively insensitive to MG132, with an $IC_{50}$ of approximately 400 nM. In contrast, cells expressing G93A SOD1 were approximately 5-fold more sensitive to MG132 ($IC_{50}$~75 nM). In these cells, protein aggregation was detected after 24 h and loss of cell viability was detected at approximately 48 h. Qualitatively similar results were obtained with the structurally distinct proteasome inhibitor bortezomib (Velcade®), suggesting that PC12 cells are indeed susceptible to proteasome inhibition and not some other effect of MG132. The ability of protein aggregates to induce cell death was examined by treating G93A SOD1-expressing cells with MG132 for 24 h, removing the MG132 by washing and assaying cell viability after another 24 h. Because the loss of cell viability was similar following MG132 removal (FIG. 1, part C), it is likely that mutant SOD1 aggregates contribute directly to cytotoxicity in PC12 cells. However, this effect is specific for G93A SOD1 suggesting that this mutant may produce higher levels of a toxic aggregated form of SOD1.

Figure 2A:
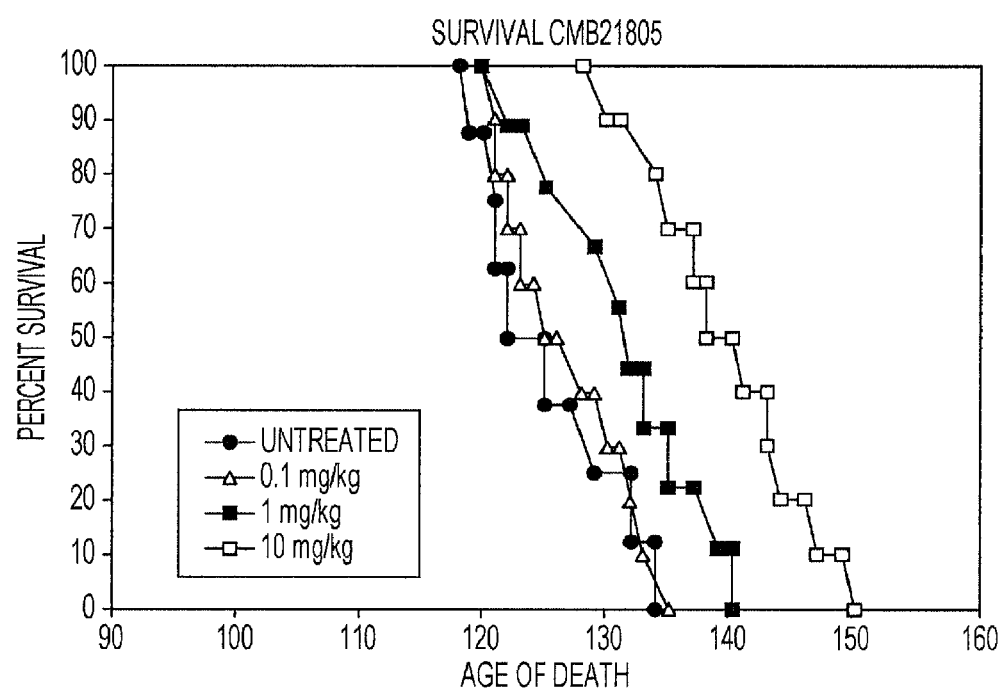
FIG. 2. 2a) Kaplan-Meier curve of CMB-021805 treated G93A SOD1 mice dosed q.d. (once per day) with CMB-021805 at 0.1 mg/kg, 1 mg/kg or 10 mg/kg. 2b) Repeat Kaplan-Meier curve of CMB-021805 treated G93A SOD1 mice dosed q.d. (once per day) at 0.1 mg/kg, 1 mg/kg, 10 mg/kg or 20 mg/kg.; 2c) Second repeat Kaplan-Meier curve of CMB-021805 treated G93A SOD1 mice dosed q.d. (once per day) at 20 mg/kg or 30 mg/kg or b.i.d (twice per day) at 10 mg/kg. The 10 mg/kg q.d., 20 mg/kg q.d. and 10 mg/kg b.i.d. treatments all show statistically significant lifespan extensions.
Figure 2B:
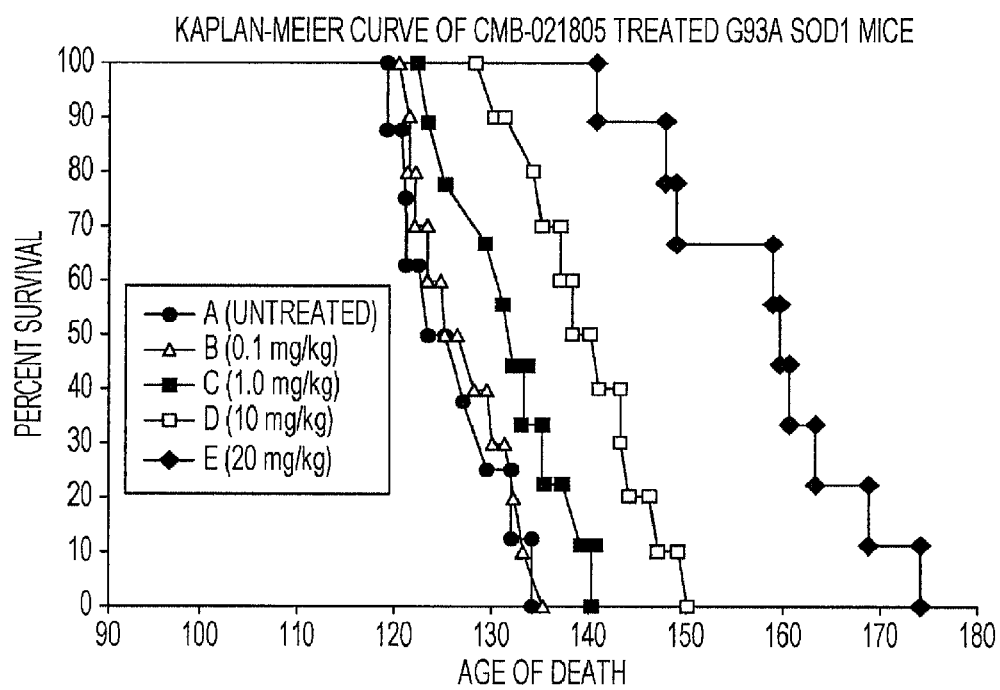
Figure 2C:
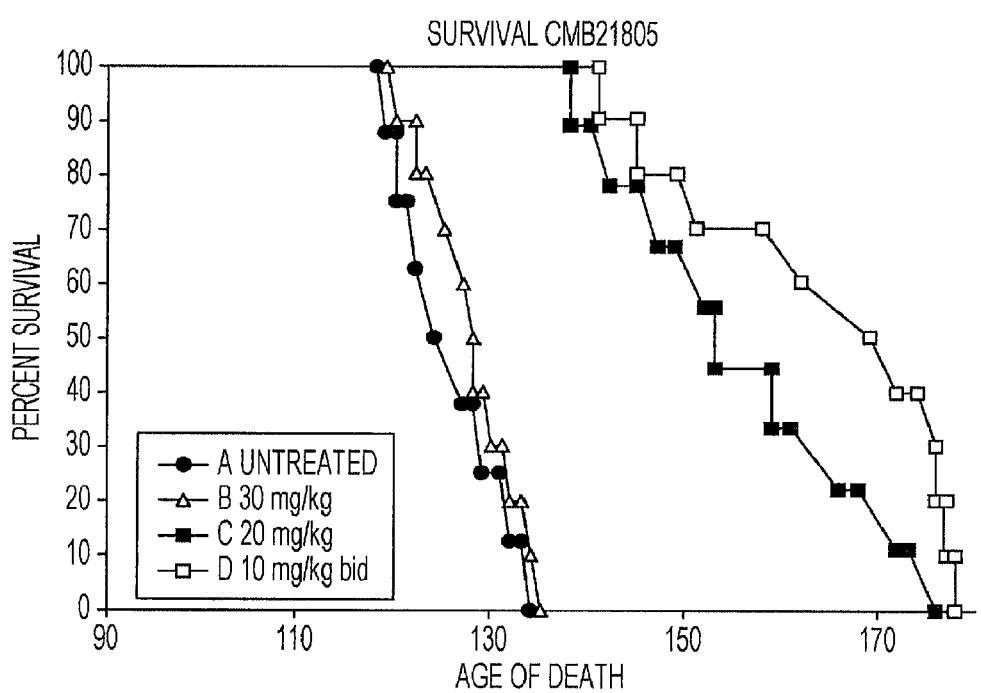

Based on these results, a high throughput screen was developed for compounds that protect against the cytotoxicity of G93A SOD1 protein aggregates using geldanamycin or radicicol as a positive control. PC12 cells expressing G93A SOD1 were treated with 100 nM MG132 with or without co-treatment with geldanamycin or radicicol. The latter compounds inhibit the chaperone HSP90 and induce expression of other chaperones. As anticipated, radicicol reduced formation of protein aggregates and increased cell viability in a dose-dependent manner (FIG. 2). Statistical analysis of the data produced a Z' value of 0.55, which would predict good performance as a positive control in a high throughput screen (Zhang et al. *J. Biomol. Screen* 1999, 4(2), 67-73).

Mutant SOD1 Direct Protein Aggregation Assay.

Compounds that are active in the above assay could theoretically protect against mutant SOD1-induced cytotoxicity through a number of mechanisms, including the following: 1) Compounds could nonspecifically block or reverse protein aggregation via chaperone induction, as observed for radicicol and geldanamycin 2) Compounds could block or reverse the aggregation of a specific aggregated protein form 3) Compounds could interfere with an event downstream of protein aggregation that plays a critical role in mutant SOD1-induced cytotoxicity (e.g., proteasome function). 4) Compounds could act directly on SOD1 in a manner that prevents mutant SOD1 aggregation. These possibilities were tested using an assay that directly measures protein aggregation. In addition, unlike the high throughput cytotoxicity protection assay, the protein aggregation assay is based on G85R SOD1; this broadens the scope of the screening strategy, and should eliminate compounds with highly specific activity (i.e., G93A SOD1 limited) against protein aggregation.

Figure 3:
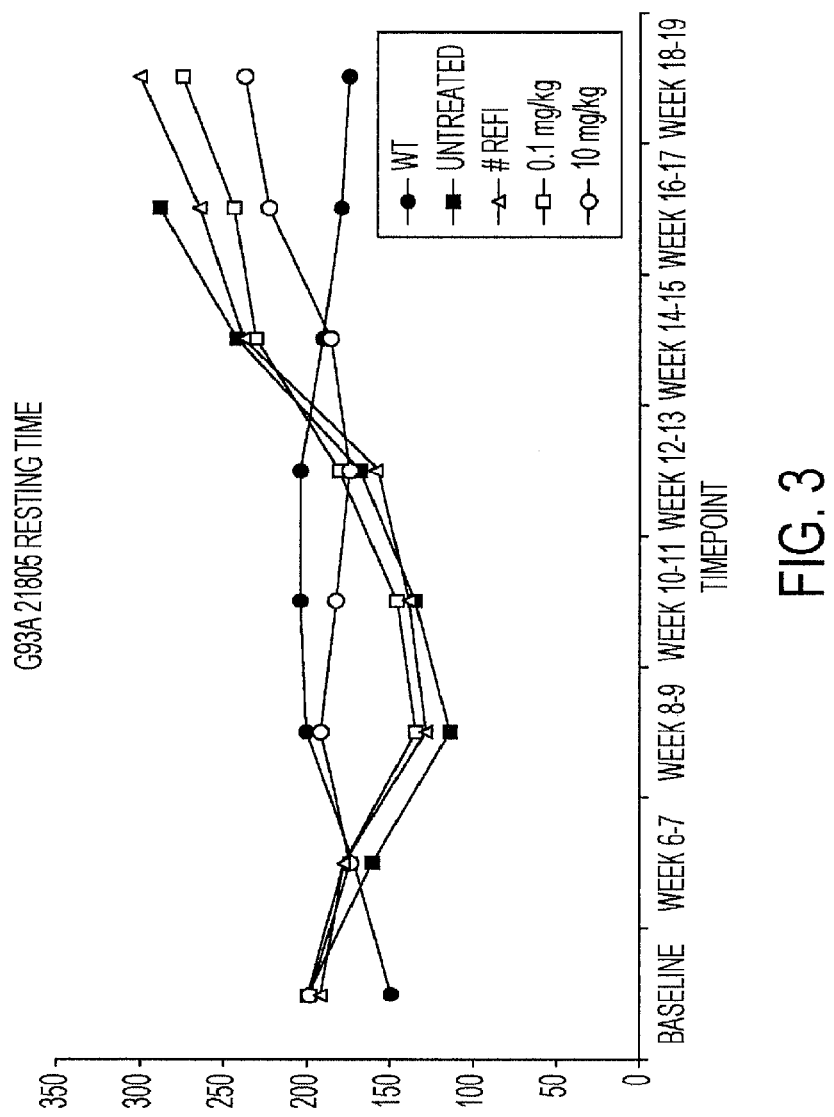
FIG. 3. Effect of CMB-021805 on behavioral parameters: resting time.

In PC12 cells that express wild-type SOD1, SOD1 was diffusely localized throughout the cell (Matsumoto et al. *J. Cell. Biol* 2005, 171(1), 75-85). In contrast, G85R SOD1 showed heterogeneous patterns of localization; in most cells, G85R was diffusely localized throughout the cell, but in ~5% of the cells, G85R SOD1 was localized in large peri-nuclear aggregates. In cells treated with MG132, up to 75% of cells expressing G85R SOD1 contain such protein aggregates (FIG. 3), but no aggregation was observed in cells expressing wild-type SOD1. Cells expressing G93A mutant SOD1 showed an intermediate level of protein aggregation: none of the cells developed protein aggregates in the absence of MG132, and ~75% of the cells had protein aggregates following treatment with MG132 (FIG. 3). Similar effects were observed in cells treated with bortezomib (Velcade®). Therefore, these effects are likely to be due to MG132-induced proteasome inhibition, and not due to an off-target effect of MG132.

Figure 4:
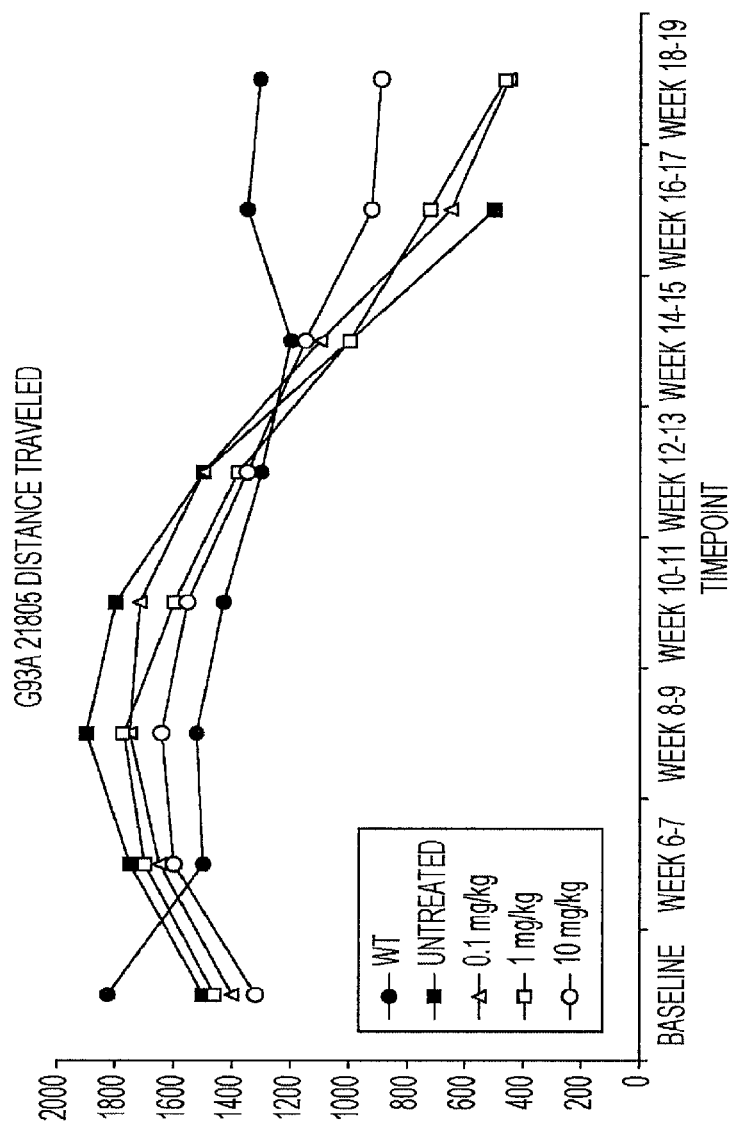
FIG. 4. Effect of CMB-021805 on behavioral parameters: distance traveled.

The sensitivity of this assay was optimized by selecting conditions that maximize the difference between active and inactive samples. The identification of a positive control is a crucial step in assay development. Thus, PC12 cells expressing G85R or G93A mutant SOD1 were treated with MG132 to induce protein aggregation, and then co-treated with candidate chemical suppressors of protein aggregation. Two compounds with similar activity were identified in these experiments: geldanamycin and radicicol. Both compounds induce heat shock transcription factor HSF-1, which in turn induces the heat shock response (FIG. 4). Treatment with radicicol reduced the proportion of cells with aggregates from 75% to 25%, a sufficient difference to allow visual scoring for compounds with efficacy equal to or greater than radicicol.

Figure 5:
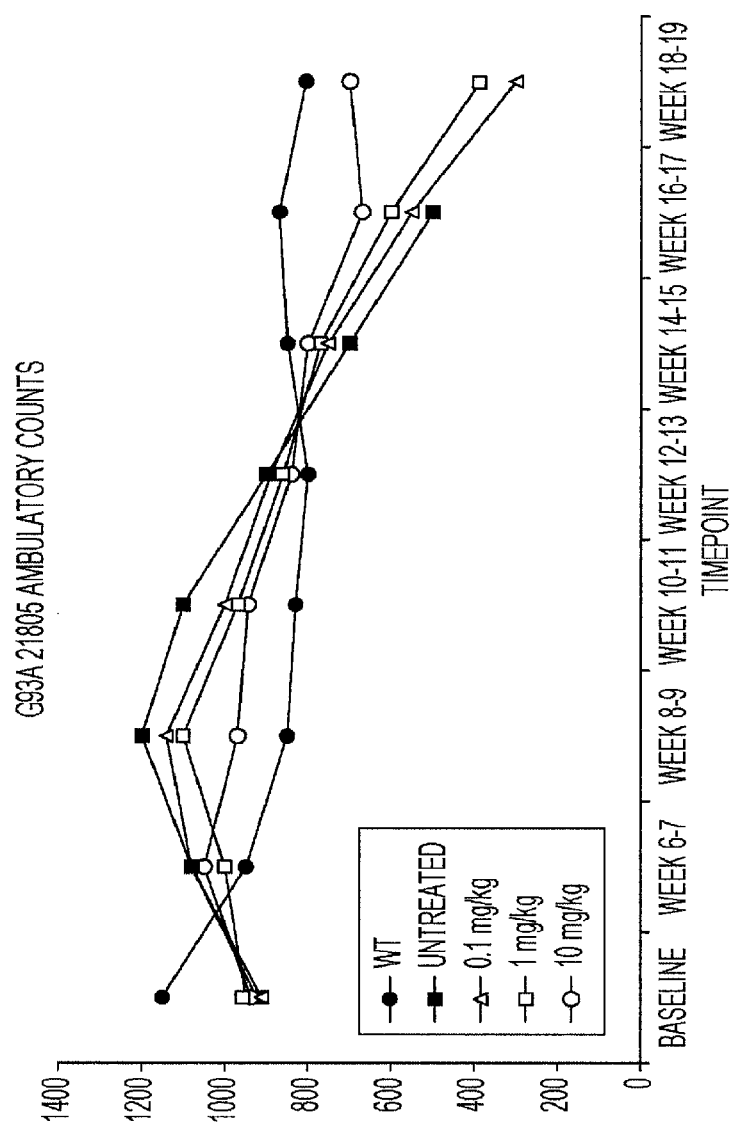
FIG. 5. Effect of CMB-021805 on behavioral parameters: ambulatory counts.
Figure 6:
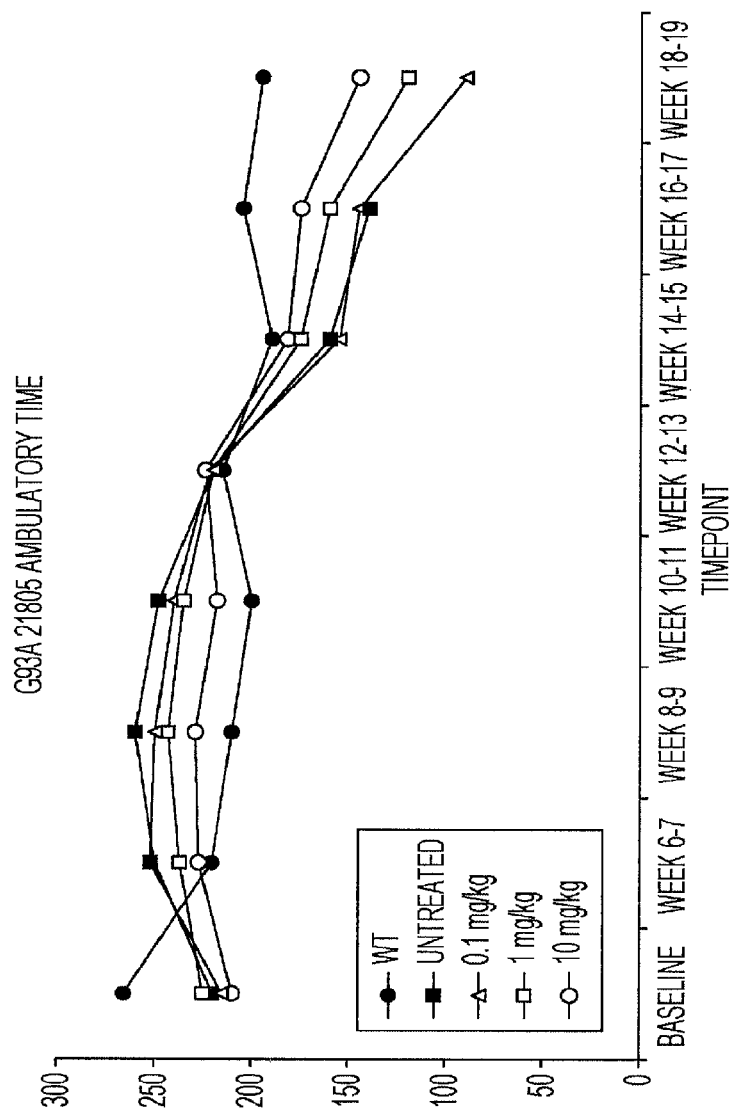
FIG. 6. Effect of CMB-021805 on behavioral parameters: ambulatory time.
Figure 7:
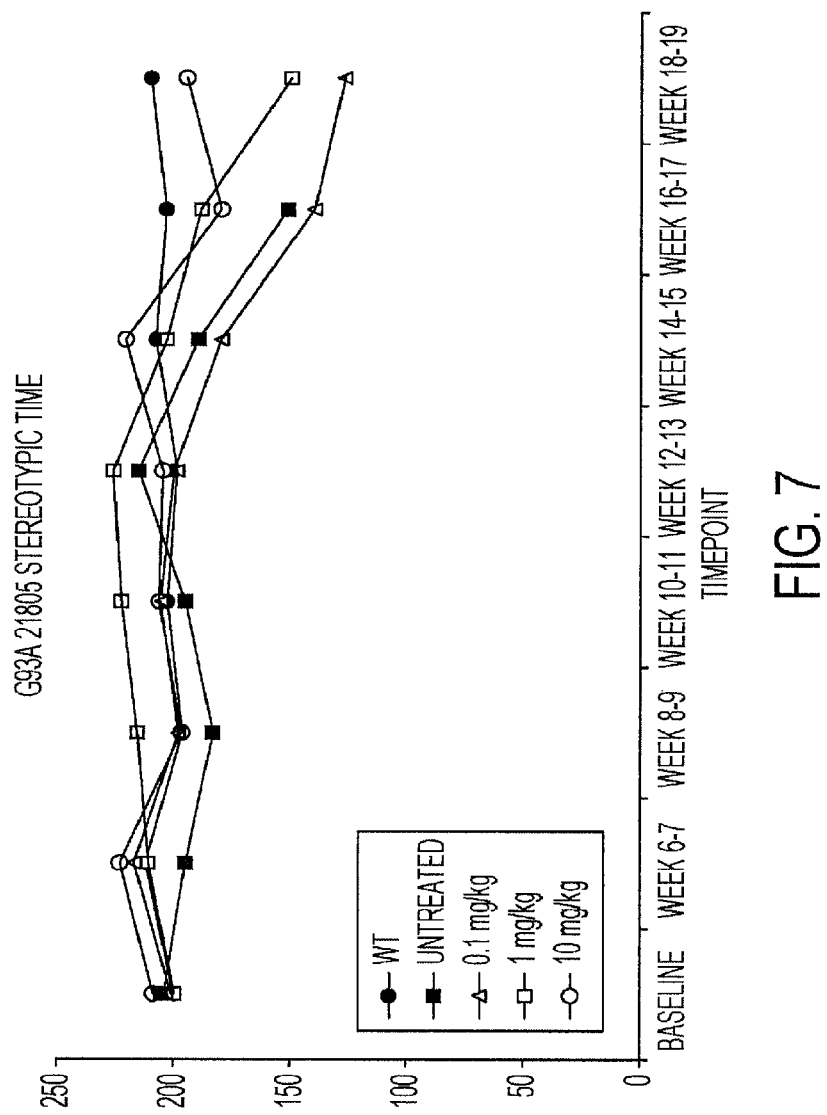
FIG. 7. Effect of CMB-021805 on behavioral parameters: stereotypic time.

To allow this assay to be used in a high-throughput manner, a Cellomics Arrayscan® high content microscopy system was used for screening and quantification. Initial experiments indicated that G85R SOD1 aggregates were more readily recognized by the high content microscopy system and its computer algorithm. Because the most robust high content assays measure events on a per cell basis, it was necessary to select a fluorescent stain that marks whole cells to be used with a compatible stain that marks intracellular structures. On the basis of pilot experiments with a number of vital dyes, an Image-iT conjugated wheat germ agglutinin (WGA) dye from Molecular Probes was selected and a computer algorithm for detecting WGA was developed. As shown in FIG. 5, WGA provided an excellent cellular marker that did not interfere with detection of YFP-tagged SOD1.

Example 2

Identification of Chemical Lead(s) Whose Predicted Pharmacological Properties are Suitable for Testing in Mice The most common and most rigorous approach to determine the toxicity and pharmacological properties of candidate pharmacological compounds relies on in vivo testing in laboratory animals. Because animal testing is both expensive and time consuming, many drug discovery organizations have turned to in vitro methods to analyze the pharmacological properties of compounds during structural optimization. This approach relies on miniaturized predictive in vitro ADMET assays that are amenable to high- to medium-throughput implementation. The need for methods of this type has also been motivated by the switch from animal disease models to target based in vitro methods for lead discovery (Kerns et al. *Curr. Top Med. Chem.* 2002, 2(1), 87-98; Di et al., *Curr. Opin. Chem. Biol.* 2003, 7(3) 402-408; Kassel et al., *Curr. Opin. Chem. Biol.* 2004, 8(3), 339-345). The in vitro ADMET approach is based on the use of a suite of chemical tests (compound integrity, compound solubility, compound aggregation, lipophilicity, pKa) and biological assays (Caco-2 and/or PAMPA assays, cytochrome P450 metabolism and inhibition, cardiac risk, and cytotoxicity) that assess the absorption, distribution, metabolism, excretion, and toxic effects of test compounds. The output from ADMET assays is used to identify and select for compounds with low predicted toxicity and desirable predicted pharmacological properties during SAR-based optimization. Compounds optimized by this approach are selected for analysis in the mouse model of ALS. The following suite of assays are performed:

Cytotoxicity is determined in cultured cells.

Compound Purity:

Each compound is subjected to chemical analysis to confirm molecular weight and determine purity. Only compounds>95% pure are used for further testing. Compounds<80% pure are re-purified and re-tested.

Compound Aggregation:

Aggregation of screening hits is measured using dynamic light scattering.

Solubility:

Because compounds are stored in DMSO, it is necessary to determine aqueous solubility of initial hit compounds and their analogs. High solubility in aqueous solution is necessary for high GI absorption, bioavailability, and for chemical formulation. Compounds should be soluble in aqueous solution at >10 µg/ml. Solubility of >50 µg/ml is preferred.

General Permeability:

High membrane permeability is required for effective GI absorption and optimal bioavailability. Passive permeability is typically assessed in the PAMPA artificial membrane assay (Kansy et al., *J. Med. Chem.* 2002, 45(8), 1712-1722). Cell-based permeability determinations using the Caco-2 cell assay are more resource intensive but more predictive of active transport or efflux in vivo (Artursson et al., *Adv. Drug. Deliv. Rev.* 2001, 46(1-3), 27-43). Caco-2 assays are performed as needed during SAR development. *Blood Brain Barrier*: CNS therapeutics must penetrate the blood-brain barrier (BBB) to achieve in vivo efficacy (Basak et al., *Pharm Res.* 1996, 13(5), 775-778). A QSAR model was developed for predicting in vivo BBB partitioning using the logarithm of the blood-brain concentration ratio as a diagnostic indicator. A 189 compound dataset was constructed from data in the literature (Rose et al., *J. Chem. Inf. Comp. Sci.* 2002, 42(3), 651-656; Pan et al., *J. Chem. Inf. Comp. Sci.* 2004, 44(6), 2083-2098) and compounds in the dataset entered as 2D structural drawings with ISIS/Draw and saved as mol files and converted into 3D structures using the Corina software prior to calculating molecular descriptors using Dragon. A Support Vector Machine (SVM) linear regression algorithm was used to generate & validate the model. The prediction accuracy (Q) for the SVM linear regression training model (n=166) and validation set (n=24) was 86.75 and 86.96%, respectively, confirming the validity of the model. Using this BBB predictive model, the potential of active compounds to cross the BB is appraised early during development. Other BBB predictive models, including a variant of the PAMPA assay developed specifically for this purpose (Di et al., *Eur J Med Chem.* 2003, 38(3), 223-32), is used as needed. Results of these experiments guide synthesis of compounds with appropriate ADME properties for use as CNS therapeutics.

Lipophilicity and pKa:

Lipophilicity is determined via octanol-water partition at pH 7.4 (Hitzel et al., *Pharm Res.* 2000, 17(11), 1389-95) and pKa is determined by capillary electrophoresis and photodiode array detection (Ishihama et al., *J Pharm Sci.* 2002. 91(4), 933-42).

Metabolism (Microsome, S9 Fraction, CYP450):

Liver Cytochrome P450 (CYP450) enzymes are the major route for xenobiotic metabolism and microsomal and hepatocyte stability is the best predictor of pharmacokinetic half-life. Cross-species comparisons of metabolism in liver microsomes can predict potential issues with liver toxicity in humans. Selected active compounds are tested in liver microsomes from efficacy species (mouse), toxicity species (rat, dog, monkey), and humans for metabolic stability.

Drug-Drug Interaction and Cardiac Risk Potential:

Data-mining algorithms and data compiled from the literature, are used to predict whether active compounds are likely to interact with and/or inhibit major Cytochrome P450's (1A2, 2C9. 2 C19, 3A4, 2D6) (Kerns et al., *Curr Top Med Chem.* 2002, 2(1), 87-98). Synthesized compounds are also tested directly for ability to bind and inhibit human CYP P450. If potential problems are indicated by these approaches, analog synthesis is directed towards developing alternative compounds. This approach allows for the assessment of cardiac safety, since hERG inhibition is assessed simultaneously on the same compounds. The hERG assay is done with the fast-patch methodology. hERG ion channel inhibition is implicated in greater than 90% of reported cases of cardiac toxicity, and is a common cause of after market drug failures and withdrawals. Information on hERG inhibition as well as inhibition of five major human CYP450s (1A2, 2C9. 2 C19, 3A4, 2D6) allows for accurate prediction of potential drug-associated cardiac risk.

Plasma Stability:

Plasma stability of active compounds is assessed in efficacy species (mouse), toxicity species (rat, dog, monkey), and human cells.

Plasma Protein Binding:

Plasma protein binding is examined in efficacy species (mouse), toxicity species (rat, dog, monkey), and human cells using ultrafiltration methodology.

The compounds identified were evaluated in the transgenic G93A ALS mouse model. ADME data was used to determine optimal route of administration. $LD_{50}$ and maximally-tolerated dose were determined, and that information was used to design and execute pharmacokinetic studies to assess brain bioavailability, and to guide choice of dosing regimen (i.e., frequency, dose, route). Three-dose basic efficacy studies were performed on compounds demonstrating acceptable tolerability and bioavailability. For compounds that demonstrated efficacy, a more complete preclinical study was performed and the efficacies of the test compound and previously characterized neuroprotective agents were compared. In certain embodiments, this includes further dose optimization, phenotype assessment, comparison with compounds of established efficacy, and analysis of brain tissue in treated animals.

Example 3

Identification and Characterization of Lead PYT Compounds Using in Vitro ADMET Assays and In Vivo Efficacy Studies The present Example describes identification and characterization of PYT compounds, and in particular of PYT compounds that are active in both protection and aggregation assays. Some PYT compounds described herein show $EC_{50}$s below 10, 9, 8, 7, 6, 5, 4, 3, 2, 1 micromolar or less. Some PYT compounds described herein show $EC_{50}$s within the 1-2 micromolar range. Some such PYT compounds described herein show 100% protection. Some such PYT compounds described herein show little or no detectable cytotoxicity at 100 micromolar concentrations.

Of more than 200 PYT compounds tested, the overall activity rate was 16% or greater.

In Vitro ADME Study of PYT Compounds.

CMB-021805 was evaluated for its in vitro ADME properties. The study showed that CMB-021805 has an $EC_{50}$ of 1.6 uM, medium human metabolic potential ($T_{1/2}$=99 min), a medium mouse metabolic potential ($T_{1/2}$=58 min), medium plasma stability ($T_{1/2}$=29 min), high Caco-2 permeability (A-B=39.26 cm/s), and excellent oral absorption. CMB-021805 is non-toxic and well-tolerated at 100 mg/kg.

Preliminary Blood Brain Barrier (BBB) Penetration Experiment.

An in vivo BBB penetration experiment was carried out for the PYT scaffold. CMB-021805 was selected for this experiment. Preliminary data show CMB-021805 has good BBB permeability. The blood-brain ratio of CMB-021805 is about 3:1, which means that within the dose tolerance, enough CMB-021805 is delivered to the brain (FIG. 1).

Procedures

Subjects.

In the Present Study, G93A SOD1 Mice and Littermate Controls were bred from existing colonies at the Bedford VA Medical Hospital. The male G93A SOD1 mice are mated with B6SJL females and the offspring are genotyped by PCR using tail DNA. The number of SOD1 transgenes are assessed periodically by PCR to ensure that transgene copy number does not increase or decrease significantly over the course of time. Mice are housed in micro-isolator cages in complete barrier facilities. A 12 hour light-dark cycle is maintained and animals are given free access to food and water. Control and transgenic mice of the same age (±2 days) and from the same 'f' generation are selected from multiple litters to form experimental cohorts (n=20 per group). Standardized criteria for age and parentage are used for placing individual mice into experimental groups/cohorts. Wild type mice are used for initial toxicity, tolerability, and pharmacokinetic studies and ALS mice are used for one month tolerability studies.

Tolerability, Dosing, and Pharmacokinetics.

The tolerable dose range and LD50 for each test compound was determined in wild type mice by increasing the dose b.i.d. one-fold each injection. The route of administration (p.o. by gavage or i.p.) and starting dose was based on solubility and other output from ADME studies. Initial pharmacokinetic (pK) studies were conducted by giving animals a single dose, sacrificing them after 30 min, 1 h, 2 h, 4 h, 6 h, or 12 h, and dissecting brains and spinal cords and determining drug concentration in the target tissue. Drug steady-state level were determined in animals that have been dosed for 1 week prior to sacrifice. These data were used to optimize the dosing regimen for efficacy studies. Drug doses should achieve a desirable drug concentration in the brain and spinal cord of treated mice. Working doses at least 10-fold lower than the acute tolerability dose are preferable.

Efficacy Studies.

Efficacy was measured using endpoints that clearly indicate neuroprotective function. These include amelioration of degenerative changes in the spinal cord, improved motor function, and prolonged survival. Some mice cohorts were sacrificed at a predetermined time point (120 days) for neuropathological examination, while others were sacrificed at end stage disease using criteria for euthanasia. The latter cohorts were followed temporally for behavioral analyses as well as survival.

Survival.

Mice were observed three times daily (morning, noon, and late afternoon) throughout the experiment. Mice were euthanized when disease progression was sufficiently severe that they were unable to initiate movement and right themselves after gentle prodding for 30 seconds.

Body Weights.

Mice were weighed twice a week at the same time each day. Weight loss is a sensitive measure of disease progression in transgenic G93A SOD1 mice and of toxicity in transgenic and wild type mice.

Motor/Behavioral.

Quantitative methods of testing motor function are used including Rotarod and analysis of open field behavior. Decline of motor function is a sensitive measure of disease onset and progression. Behavioral testing for the transgenic G93A SOD1 mice were performed during the light phase of the diurnal cycle since these mice are sufficiently active during that time. Measurements were made for 30 minutes after 10 minutes of acclimation to the box (Opto-Varimex Unit, Columbus Instruments, Columbus, Ohio, USA). Counts of horizontal and vertical motion activity were monitored and quantitative analysis of locomotor activity (resting and ambulatory times), were assessed. The open field box was cleaned before testing each mouse. Each 30 minutes of testing was analyzed as three periods of 10 minute intervals to study the influence of novelty and measured behavior. Mice were coded and investigators were blinded to the genotype and analysis. Testing started on week 4 and performed every other week until the mice could no longer participate.

Neuropathology.

Selected cohorts (n=10) of treated and untreated G93A SOD1 mice were euthanized at 120 days for isolation and analysis of spinal cord tissue. For this purpose, mice are deeply anesthetized and perfused transcardially with 4% buffered paraformaldehyde at the desired time point. These studies were performed in a blinded manner, to avoid bias in interpretation of the results. Brains were weighed, serially sectioned at 50 pm and stained for quantitative morphology (cresyl violet) to determine gross atrophy and identify ventral neuron loss and astrogliosis. Remaining tissue samples/sections were stored for future use. Stereology was used to quantify gross ventral horn atrophy, neuronal atrophy, and neuronal loss. Remaining tissue samples/sections are stored for prospective mechanistic analyses as necessary.

Analysis.

Data sets were generated and analyzed for each clinical and neuropathological measure. Effects on behavior and neuropathology were compared in treatment and control groups. Dose-dependent effects were assessed in each treatment group using multiple two-sided ANOVA tests. Multiple comparisons in the same subject groups were dealt with post hoc. Kaplan-Meier analysis was used for survival and behavioral function.

Neuronal Quantitation.

Serial lumbar spinal cord tissue sections (n=20) from L3-L5 spinal cord segments were used for gross spinal cord areas and neuronal analysis. Gross areas of the spinal cord sections were quantified from each experimental cohort using NIH Image. From the same sections, the ventral horn was delineated by a line from the central canal laterally and circumscribing the belly of gray matter. Absolute neuronal counts of Nissl-positive neurons were performed in the ventral horns in the lumbar spinal cord. Only those neurons with nuclei were counted. All counts were performed with the experimenter (JM) blinded to treatment conditions. Counts were performed using Image J (NIH) and manually verified and the data represent the average neuronal number from the sections used.

Interpretation.

Compound efficacy is evaluated using behavioral and neuropathological endpoints. Results for the test compound are compared with results from compounds with established efficacy and neuroprotective action in the G93A SOD1 mouse model. These experiments directly test whether PYTs provides therapeutic benefit and, if so, the magnitude of the benefit. Along the way, useful information about solubility, administration, and toxicity are also obtained.

Results:

Behavioral results of Open-Field analysis showed marked significant differences in out come measures between wild type littermate mice and untreated G93A mutant mice (FIGS. 3-6). In comparison to wild type mice, there was significant increase in hyperactivity in the untreated G93A mice in distance traveled, ambulatory counts, and ambulatory time starting at 6 weeks through 12-13 weeks. After the 12-13 week time point, there was a significant reduction in distance traveled, ambulatory counts, and ambulatory time in G93A mice, in comparison to the wild type littermate control mice. Resting time was the mirror antithesis of motor movement measures, with a significant reduction from 6 weeks through 12-13 weeks, with increased resting time after 12-13 weeks. In contrast, treated G93A mice showed motor performance changes in CMB-021805-treated mice at the highest dose (10 mg/kg) administered.

Three different doses (low, medium, and high) of CMB-021805 were tested. Parameters evaluated include (1) distance traveled; (2) resting time; (3) ambulatory count; and (4) ambulatory time. These results are presented in FIGS. 3-7. Overall survival was also assessed (see FIG. 2).

As can be seen with reference to FIGS. 3-7, the low and medium dose (0.1 mg/kg and 1.0 mg/kg) in G93A mice paralleled the untreated G93A mice for distance traveled, resting time, ambulatory count, and ambulatory time over the 6 week to 12-13 week time period. These findings are consistent with a conclusion that the low and medium dose treatment with CMB-021805 had little effect over that time period. After 12-13 weeks, mice treated with the low or medium CMB-021805 dose showed similar results as the untreated G93A mice with respect to distance traveled, resting time, ambulatory counts, ambulatory time, and stereotypic time.

As shown in FIG. 1, survival extension was significant (11.2%) at the highest dose (10 mg/kg) of CMB21805 in the G93A transgenic mice. The remaining doses of CMB21805 (0.1 mg/kg and 1 mg/kg) did not significantly extend the life span of mice (untreated G93A mice: 125.4±4.2 days; 0.1 mg/kg CMB21805-treated G93A mice: 126.5±4.3 days; 1 mg/kg CMB21805-treated G93A mice: 131.2±5.1 days; 10 mg/kg CMB218051-treated G93A mice: 139.4±5.9 days). An even higher dose (20 mg/kg) efficacy animal test is now underway.

Major Metabolites of CMB-021805.

Considering the relatively short mouse metabolic halftime ($T_{1/2}$=58 minutes) studies to determine the major metabolites were completed. As shown in Figure ??, two major MS peaks (m/z=353 and m/z=335) were detected, and the structure of the metabolites were predicted. No other metabolites were observed. The proposed metabolites were of the following structure:

CMB-021805 m/z=337 (M+H)$^+$

Potential Metabolites

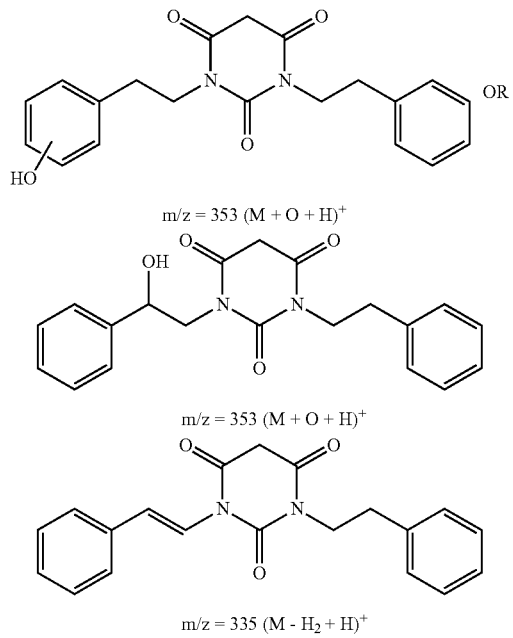

No conclusive evidence for other metabolites was observed.

Example 4

Synthesis of PYT Compounds

PYT (pyrimidine-2,4,6-triones) compounds contain three carbonyl groups and two nitrogen atoms. The $R^3/R^{3'}$ group could be unsubstituted (two hydrogens) or substituted with $sp^2$ hybridized carbons (alkenes groups) to gain activity. If one of $R^3/R^{3'}$ is alkyl, the compounds are usually inactive. When both of $R^1$ and $R^2$ are H, the PYT compounds exhibit weak activity. When $R^1$ and $R^2$ are alkyl chains with 2 more carbons, the compounds typically exhibit good potency. Some compounds with $R^1$ as hydrogen and $R^2$ as alkyl chain (>2 carbons) also exhibit moderate to good potency depending on different $R^3/R^{3'}$ group.

In order to improve the microsome stability of PYT compounds, new analogs based on the structure of CMB- 021805 were synthesized, as shown in the Schemes below. By blocking the potential metabolic pathway, these new analogs may have better potency and much longer metabolic half lives. Potency tests for these compounds are underway.

Parallel synthesis technology was applied to the synthesis of PYT compounds (see Scheme 4, below).

Scheme 4.

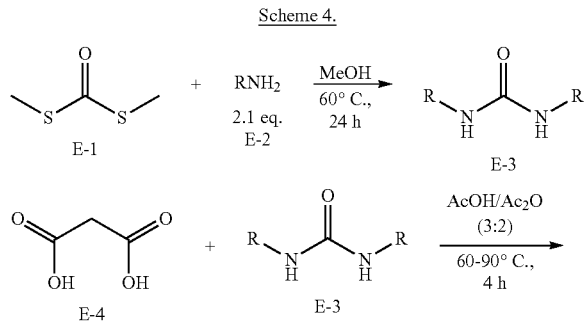

-continued

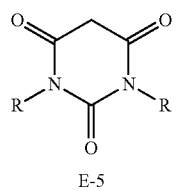

E-5

As shown in Scheme 4, starting from commercially available S,S-dimethyl carbonodithioate E-1 and one or more suitable amines, urea-type intermediates E-3 were synthesized in very high yields. Without any further purification, after removing the solvent under vacuum, the crude urea compound reacted with malonic acid to provide the desired PYT compounds E-5 in moderate to high yields. Most of the final products could be easily recrystallized from ether/hexanes. The reactions were carried out in 10 mL vials for a total of 2 days, and usually 8-12 reactions were set up at the same time on pie blocks with an IKA stir plate. By this method, the synthesis of PYTs proceeded in high yields, with simple purification procedures, good purity, varieties of structures, and ease for SAR studies.

Scheme 5.

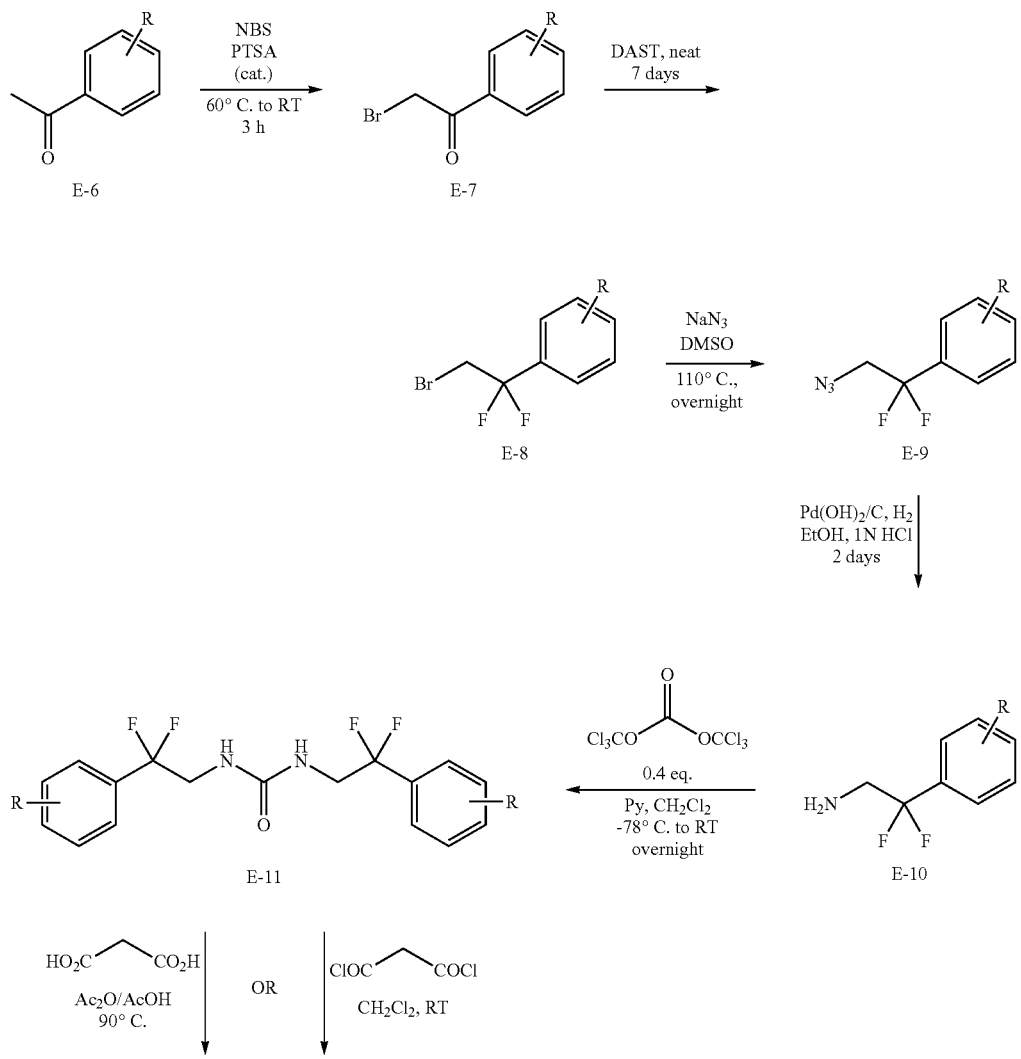

-continued

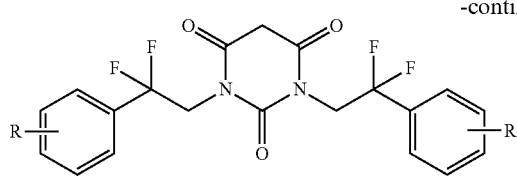

E-12

Scheme 5 (above) depicts the synthesis of fluorinated PYT compound E-12. E-6 was halogenated (using, e.g., n-bromosuccinimide (NBS)) in the presence of a catalyst (e.g., PTSA) to provide alpha-halo compound E-7. Exposure of E-7 to a suitable fluorinating reagent (e.g., diethylaminosulfur trifluoride (DAST)) afforded gem-difluoro compound E-8. The alpha halide moiety of E-8 could then be displaced using an azide salt (e.g., sodium azide) to afford compound E-9. Reduction of the azide group of E-9 using a suitable reducing agent (e.g., Pd(OH)$_2$/C) under acidic conditions provided the corresponding amine salt E-10. Addition of a suitably activated carbonate (e.g., bis(trichloromethyl)carbonate) to amine E-10 under basic conditions produced urea E-11, which could then react with malonic acid, or a derivative thereof, to generate PYT compound E-12. Exemplary compounds generated using the above synthetic route are shown below in Table 1, below.

TABLE 1

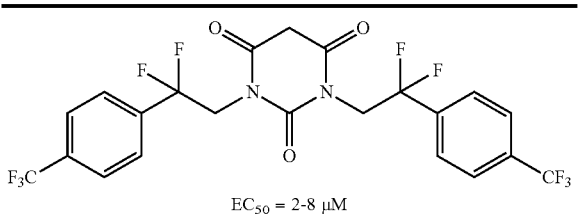

EC$_{50}$ = 2-8 μM

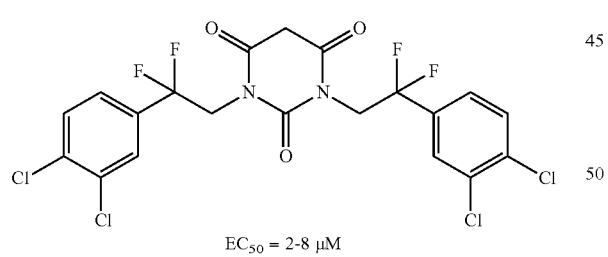

EC$_{50}$ = 2-8 μM

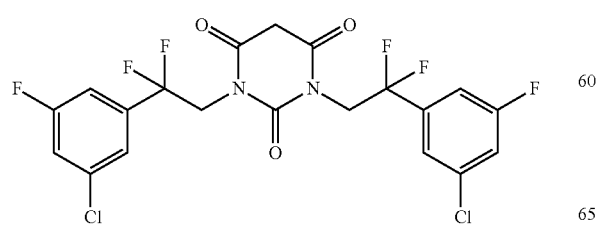

TABLE 1-continued

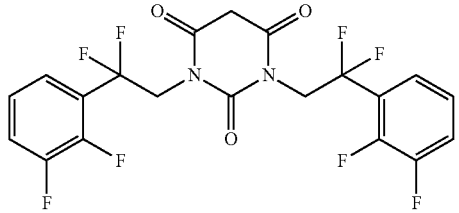 [SMILES: O=C1CC(=O)N(CC(F)(F)c2cccc(F)c2F)C(=O)N1CC(F)(F)c1cccc(F)c1F]

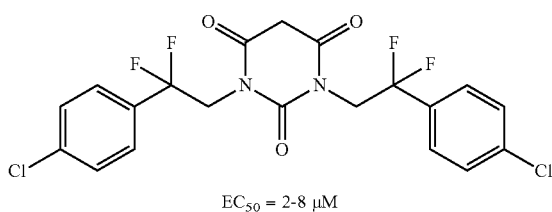

EC$_{50}$ = 2-8 μM

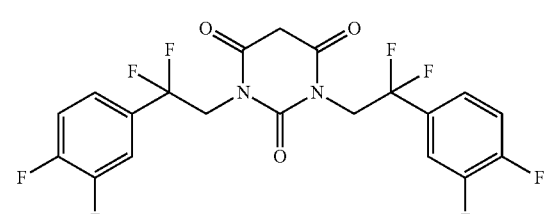

EC$_{50}$ = 2-8 μM

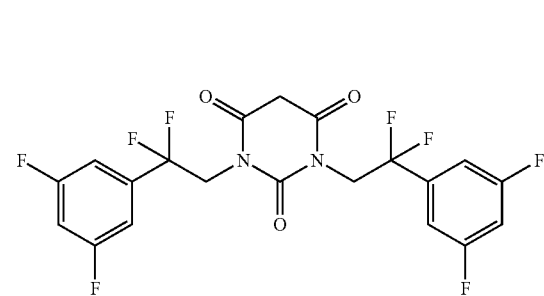 [SMILES: O=C1CC(=O)N(CC(F)(F)c2cc(F)cc(F)c2)C(=O)N1CC(F)(F)c1cc(F)cc(F)c1]

Scheme 6

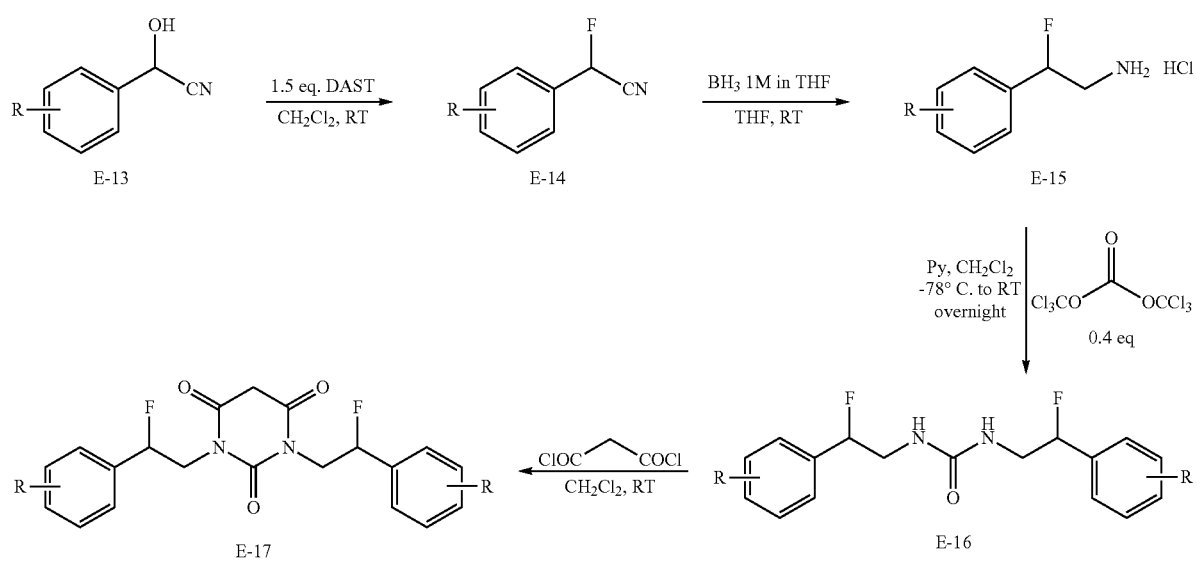

Scheme 6 (above) depicts the synthesis of fluorinated PYT compound E-16. Exposure of E-13 to a suitable fluorinating reagent (e.g., (DAST)) afforded monofluorinated compound E-14. The nitrile moiety of E-14 was reduced using a suitable reducing agent (e.g., borane) to afford the corresponding amine E-15. Addition of E-15 to a suitably activated carbonate (e.g., bis(trichloromethyl)carbonate) under basic conditions produced urea E-16, which was then reacted with malonic acid, or a derivative thereof, to generate PYT compound E-17.

-continued

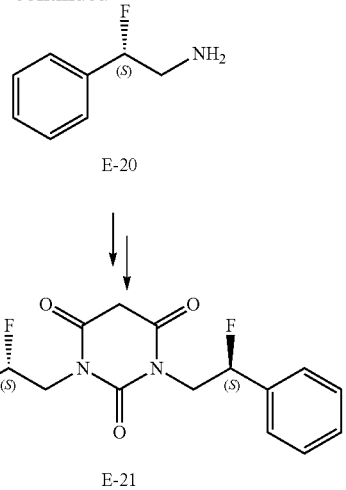

Scheme 7.

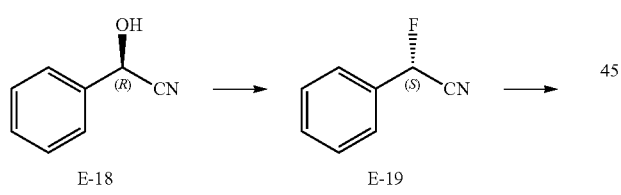

Scheme 7, above, depicts the exemplary synthesis of E-21 starting with a single enantiomer of 2-hydroxy-2-phenylacetonitrile E-18 using the above-described procedure. One of skill in the art would understand that use of the opposite enantiomer (i.e., the (S)-enantiomer) is also contemplated.

Scheme 8.

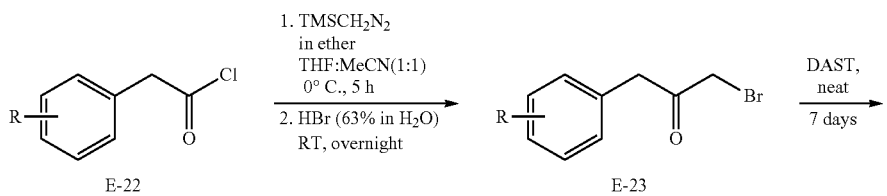

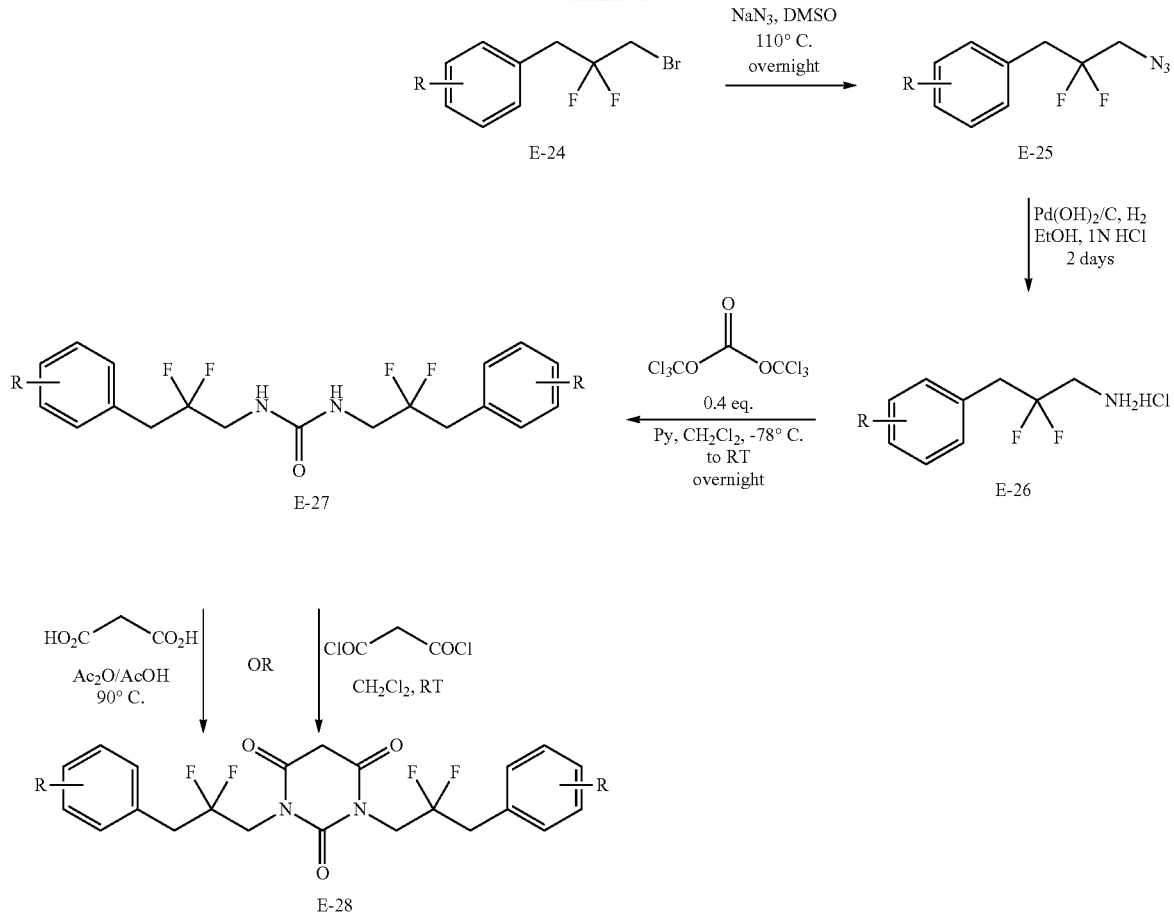

Scheme 8 (above) depicts the synthesis of fluorinated PYT compound E-28. Exposure of acid chloride E-22 to trimethylsilyldiazomethane in ether, followed by treatment with aqueous HBr at room temperature overnight afforded bromide E-23. E-23 was fluorinated using a suitable fluorinating reagent (e.g., DAST) to afford the corresponding gem-difluoro derivative E-24. Addition of sodium azide to E-24 produced azide E-25, which was reduced under acidic conditions generate the corresponding amine salt E-26. Addition of E-26 to a suitably activated carbonate (e.g., bis(trichloromethyl)carbonate) under basic conditions produced urea E-27, which was then reacted with malonic acid, or a derivative thereof, to generate PYT compound E-28.

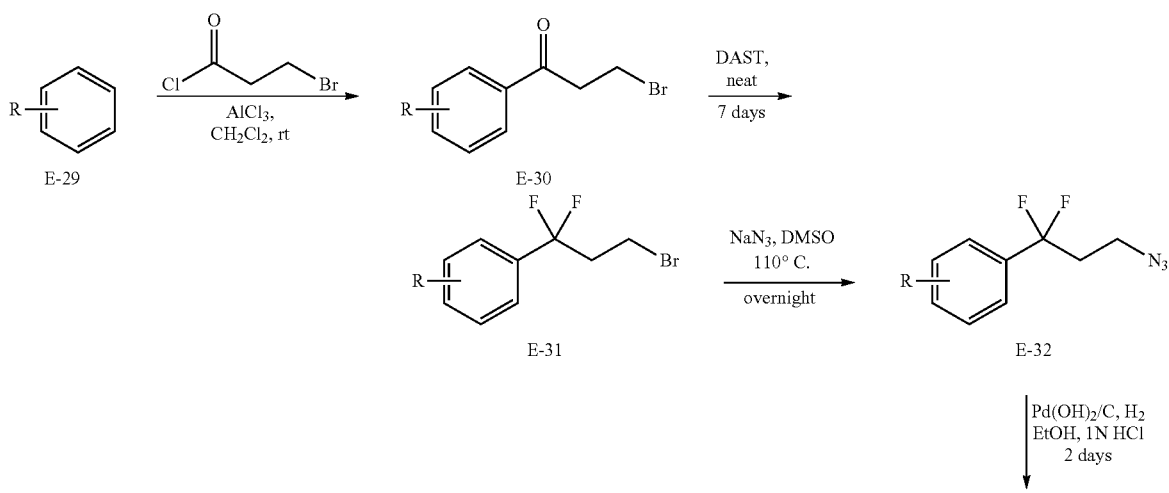

-continued

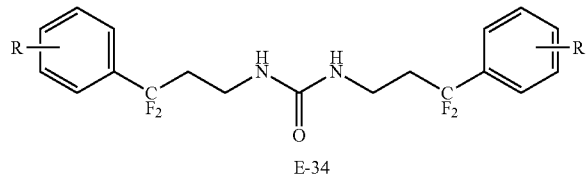
E-34

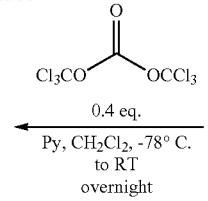

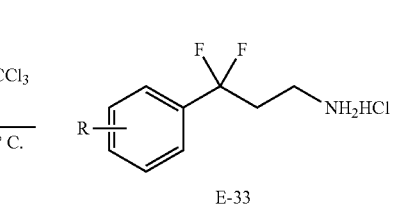
E-33

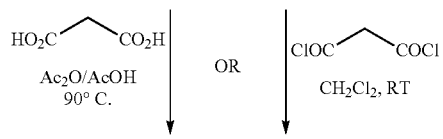

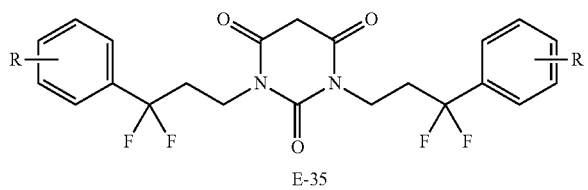
E-35

Scheme 9 (above) depicts the synthesis of fluorinated PYT compound E-35. Friedel-Crafts acylation of E-29 using 3-bromopropanoyl chloride and aluminum trichloride produced ketone E-30. E-30 was fluorinated using a suitable fluorinating reagent (e.g., DAST) to afford the corresponding gem-difluoro derivative E-31. Addition of sodium azide to E-31 produced azide E-32, which was reduced under acidic conditions to generate the corresponding amine salt E-33. Addition of E-33 to a suitably activated carbonate (e.g., bis(trichloromethyl)carbonate) under basic conditions produced urea E-34, which was then reacted with malonic acid, or a derivative thereof, to generate PYT compound E-35.

Scheme 10.

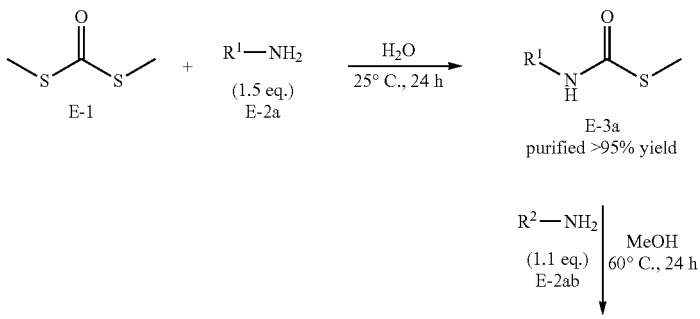

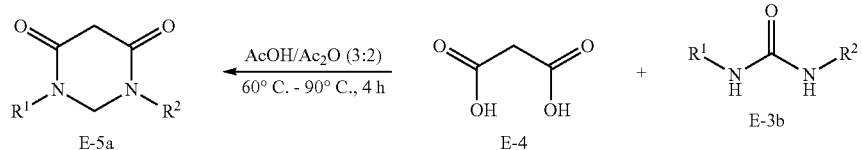

Scheme 10 depicts a synthetic route designed to access PYTs with different $R^1$ and $R^2$ groups. By changing parameters such as the reaction solvent, temperature, and the amount of starting material, a precursor to the urea compound could be obtained in high yields after purification, and this reaction was amenable to scale-up. This precursor could react with a second amine to provide the desired urea intermediate with different $R^1$ and $R^2$ groups. Using standard parallel synthesis procedures, PYT compounds with different $R^1$ and $R^2$ group were generated.

Further modifications on the $R^3/R^{3'}$ position of PYT were executed. However, when a methyl group (sp$^3$) was introduced at the $R^3/R^{3'}$ position, the compounds showed no potency at all. In certain instances, an sp$^2$-hybridized blocking group is needed at the $R^3/R^{3'}$ position to maintain the potency of the PYTs, although it does not necessarily increase the potency as desired.

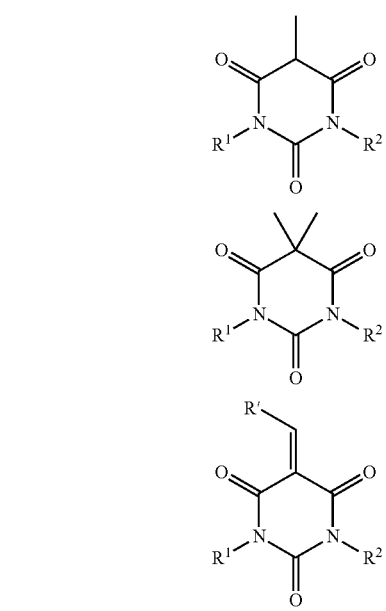

Scheme 11.

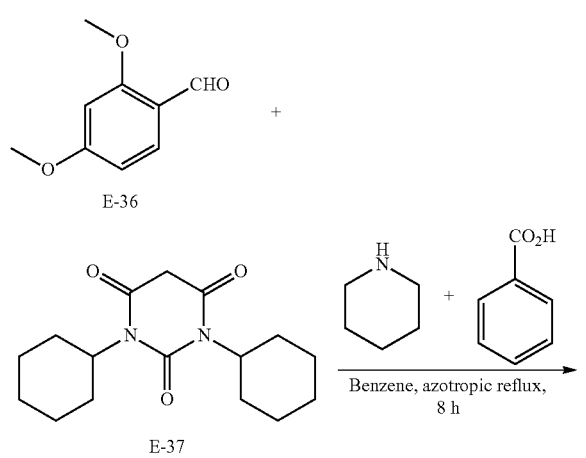

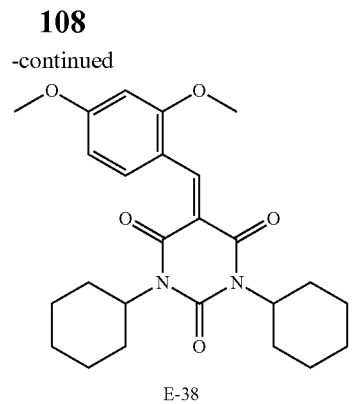

E-38

Scheme 11, above, depicts the introduction of an sp$^2$-hybridized group to the PYT ring at the $R^3/R^{3'}$ position via a Knoevenagel condensation reaction. Specifically, benzaldehyde E-36 reacts with PYT compound E-37 in the presence of piperidine and benzoic acid to provide modified PYT compound E-38. One of skill in the art would understand that a range of suitably functionalized benzaldehydes can be employed in this reaction to afford modified PYT compounds of varying structures.

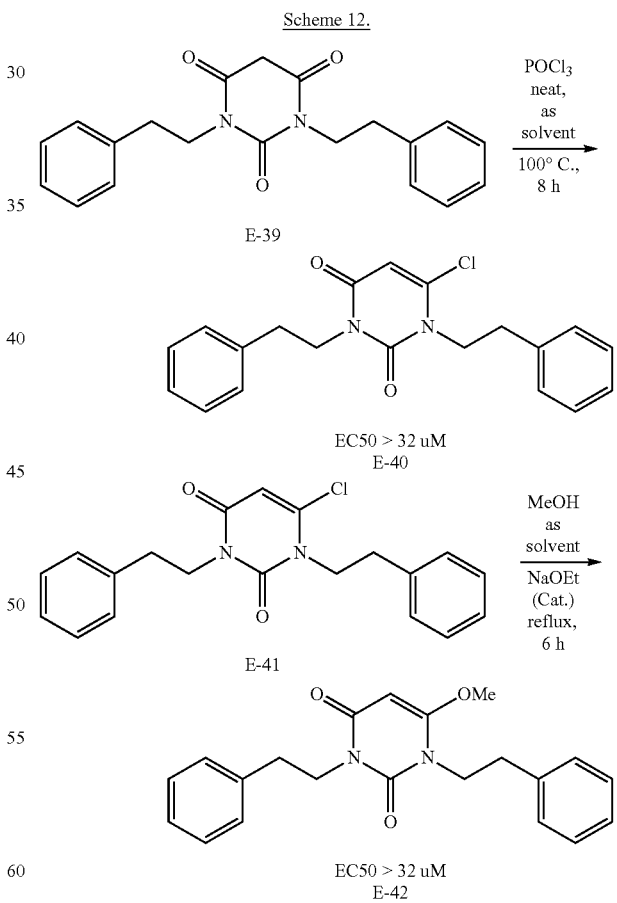

As shown in Scheme 12, above, attempts to modify the PYT ring to enol forms were successfully performed. Unfortunately, the enol forms of PYT compounds were not potent at all.

X-Ray Analysis of PYT Core

Figure 8:
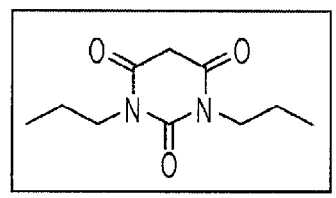
FIG. 8. X-ray analysis of PYT core.
Figure 8:
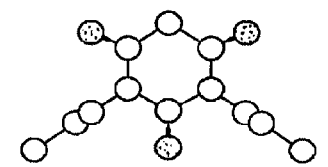
Figure 8:
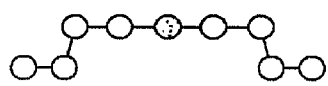
Figure 9:
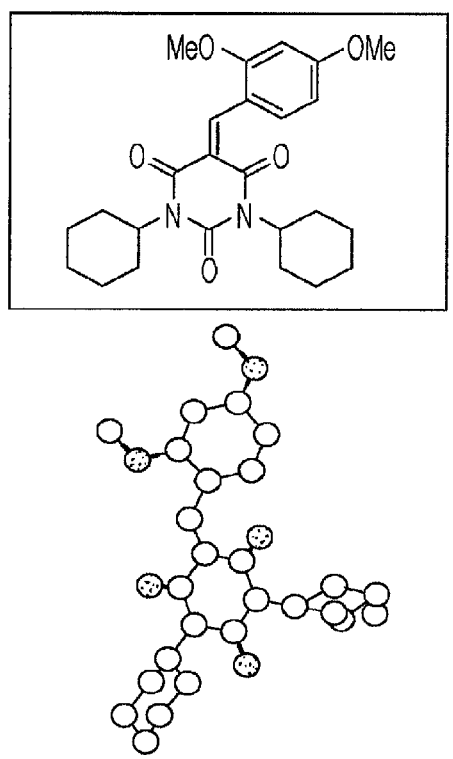
FIG. 9. X-ray analysis of PYT compounds with $sp^2$ substituted group.

Studies on the structure of PYT compounds were carried out. In order to get a clear vision of the structure of the PYT core (the six membered ring), several X-ray quality crystals were obtained for different PYTs. As shown in FIG. 8, the six membered ring of PYT core is very flat, which is quite similar to a benzene ring. The two side chains are pointing to the same side of the core. Even for the PYT compounds with $sp^2$ substituted groups on the $CH_2$ group of the six membered ring, the PYT core is still very flat (FIG. 9). The two side chains are also pointing to the same side.

EQUIVALENTS

Having described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound of Formula I:

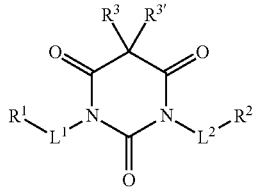

I or a pharmaceutically acceptable salt thereof, wherein:
$L^1$ is $(C(R)_2)_n$— and wherein n is 2 to 5;
$R^1$ is phenyl, wherein $R^1$ is optionally substituted with p occurrences of $R^a$, wherein p is 0 to 2, inclusive;
each $R^a$ is independently selected from the group consisting of —R, —OR, —CN, —$NO_2$, —SR, —S(O)R, —$SO_2R$, —C(O)R, —$CO_2R$, —C(O)N(R)$_2$, —NRC(O)R, —NRC(O)N(R)$_2$, —$NRSO_2R$, and —N(R)$_2$, or wherein $R^a$ is an optionally substituted 5-6 membered monocyclic saturated, partially saturated, or aromatic ring having 1-4 heteroatoms independently selected from nitrogen, oxygen, or sulfur, or an optionally substituted 8-10 membered saturated, partially saturated, or aromatic bicyclic ring having 0-4 heteroatoms independently selected from nitrogen, oxygen, or sulfur;
each R is independently hydrogen, halogen, optionally substituted $C_{1-6}$ aliphatic, optionally substituted phenyl, optionally substituted benzyl, or two R on the same nitrogen are taken together to form a 5-6 membered saturated, partially saturated, or aromatic ring having 1-3 heteroatoms independently selected from nitrogen, oxygen, and sulfur;
except for $L^1$ and $L^2$, where each R is independently hydrogen, halogen, optionally substituted phenyl, optionally substituted benzyl, or two R on the same nitrogen are taken together to form a 5-6 membered saturated, partially saturated, or aromatic ring having 1-3 heteroatoms independently selected from nitrogen, oxygen, and sulfur, and except for $R^d$ where $R^c$ is phenyl and each R is independently hydrogen, optionally substituted phenyl, optionally substituted benzyl, or two R on the same nitrogen are taken together to form a 5-6 membered saturated, partially saturated, or aromatic ring having 1-3 heteroatoms independently selected from nitrogen, oxygen, and sulfur
$L^2$ is —$(C(R)_2)_m$— and wherein m is 2 to 5;
$R^2$ is phenyl wherein $R^2$ is optionally substituted with q occurrences of $R^b$, wherein q is 0 to 2;
each $R^b$ is independently selected from the group consisting of —R, —OR, —CN, —$NO_2$, —SR, —S(O)R, —$SO_2R$, —C(O)R, —$CO_2R$, —C(O)N(R)$_2$, —NRC(O)R, —NRC(O)N(R)$_2$, —$NRSO_2R$, and —N(R)$_2$, or wherein $R^b$ is an optionally substituted 5-6 membered monocyclic saturated, partially saturated, or aromatic ring having 1-4 heteroatoms independently selected from nitrogen, oxygen, or sulfur, or an optionally substituted 8-10 membered saturated, partially saturated, or aromatic bicyclic ring having 0-4 heteroatoms independently selected from nitrogen, oxygen, or sulfur;
$R^3$ and $R^{3'}$ are independently hydrogen or halogen, or $R^3$ and $R^{3'}$ are taken together to form a $C_1$ alkenylene optionally substituted with one or two $R^c$ groups;
each $R^c$ is independently —R, —OR, —CN, —$NO_2$, —SR, —S(O)R, —$SO_2R$, —C(O)R, —$CO_2R$, —C(O)N(R)$_2$, —NRC(O)R, —NRC(O)N(R)$_2$, or —$NRSO_2R$, or wherein $R^c$ is phenyl, a 5-6 membered monocyclic saturated, partially saturated, or aromatic ring having 1-4 heteroatoms independently selected from nitrogen, oxygen, or sulfur, or an 8-10 membered saturated, partially saturated, or aromatic bicyclic ring having 0-4 heteroatoms independently selected from nitrogen, oxygen, or sulfur, and wherein $R^c$ is optionally substituted with t occurrences of $R^d$, wherein t is 0 to 5, inclusive; and each $R^d$ is independently —R, —OR, —CN, —C(R)$_3$, —NO$_2$, —SR, —S(O)R, —SO$_2$R, —C(O)R, —CO$_2$R, —C(O)N(R)$_2$, —NRC(O)R, —NRC(O)N(R)$_2$, —NRSO$_2$R, or —N(R)$_2$; providing said compound is not

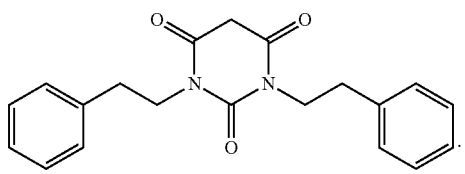 [SMILES: O=C1CC(=O)N(CCc2ccccc2)C(=O)N1CCc1ccccc1]

2. The compound according to claim 1, wherein said $L^1$ at least one R is independently halogen.
3. The compound according to claim 2, wherein at least one R is independently fluorine.
4. The compound according to claim 1, wherein $R^1$ is phenyl optionally substituted with $R^a$.
5. The compound according to claim 4, wherein at least one $R^a$ is independently halogen.
6. The compound according to claim 1, wherein said $L^2$ at least one R is independently halogen.
7. The compound according to claim 6, wherein at least one R is independently fluorine.
8. The compound according to claim 1, wherein $R^2$ is phenyl optionally substituted with $R^b$.
9. The compound according to claim 8, wherein at least one $R^b$ is independently halogen.
10. The compound according to claim 1, wherein at least one of $R^3$ or $R^{3'}$ is hydrogen.
11. The compound according to claim 1, wherein at least one of $R^3$ or $R^{3'}$ is fluorine.
12. The compound according to claim 1, of the following formula:

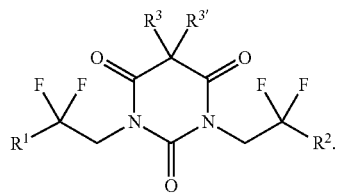

13. The compound according to claim 1, of the following formula:

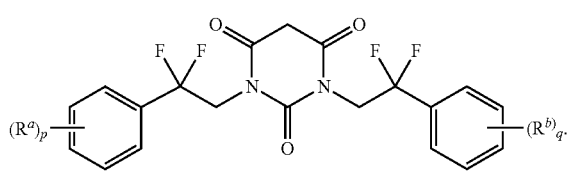

14. The compound according to claim 13, wherein at least one $R^a$ is independently a halogen.
15. The compound according to claim 13, wherein at least one $R^b$ is independently a halogen.
16. The compound according to claim 1, wherein $R^3$ and $R^{3'}$ are taken together to form a $C_1$ alkenylene optionally substituted with one or two $R^c$ groups.

17. The compound according to claim 1, of the formula:

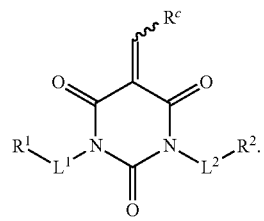

18. The compound according to claim 1, of the formula:

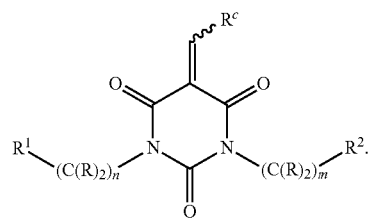

19. The compound according to claim 1, of the formula:

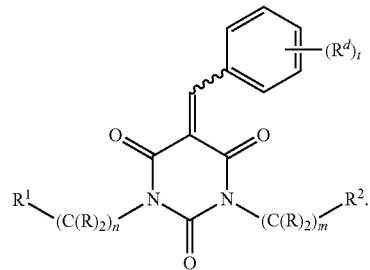

20. The compound according to claim 19, of the formula:

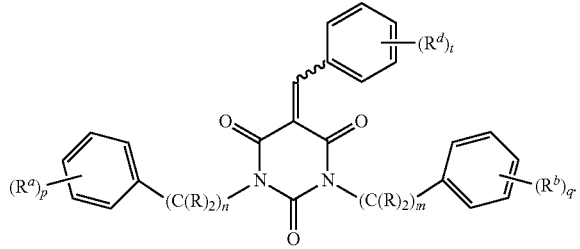

21. The compound according to claim 1, of any one of the following formulae:

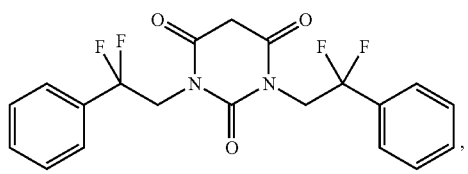

-continued
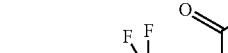

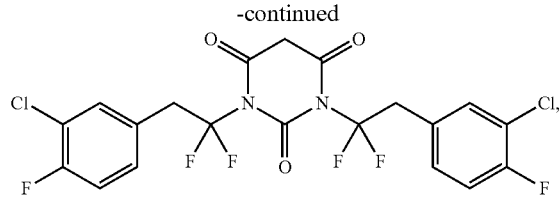
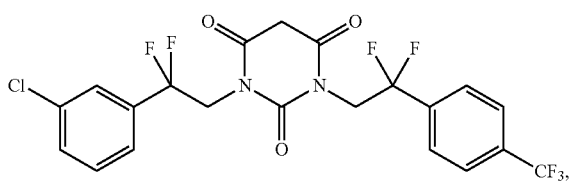
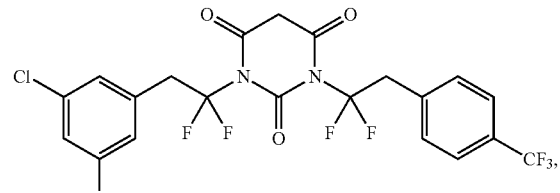
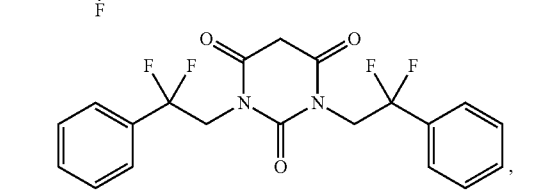
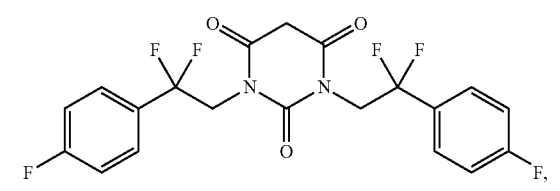
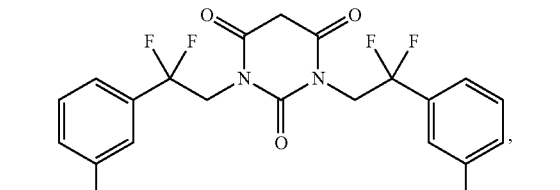
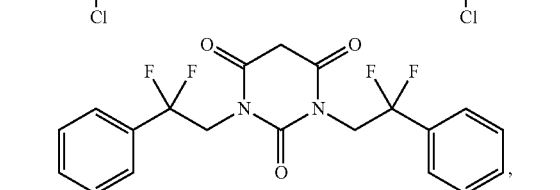
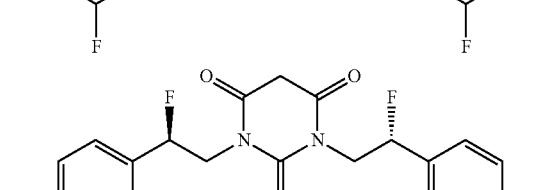
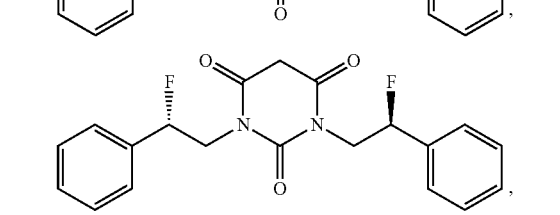
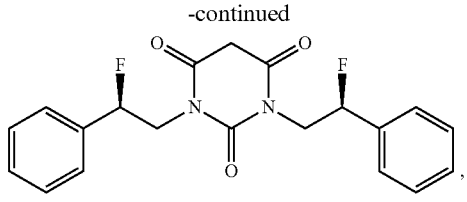
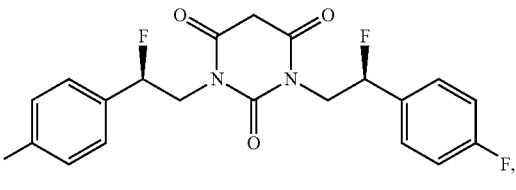
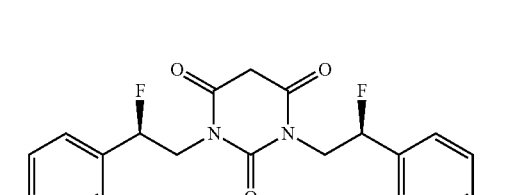
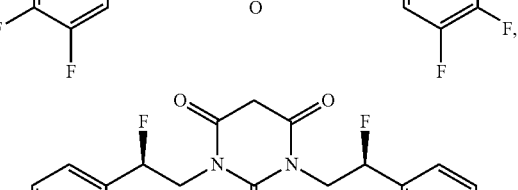
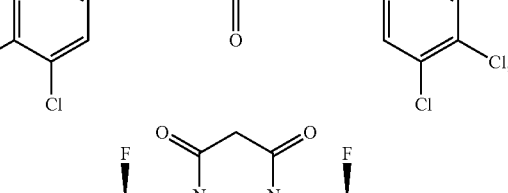
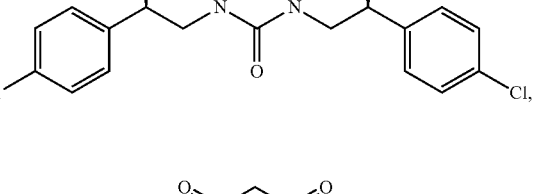
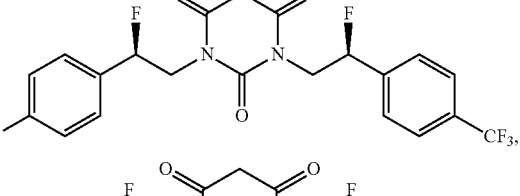
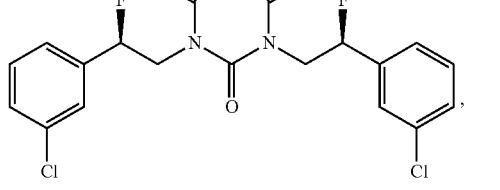
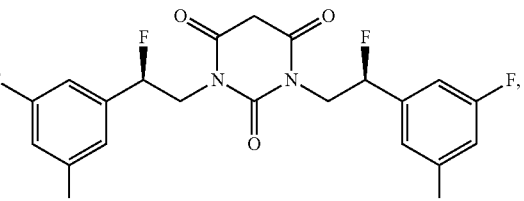

117
-continued
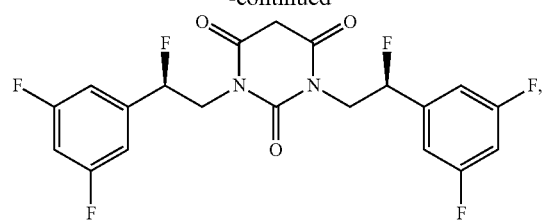
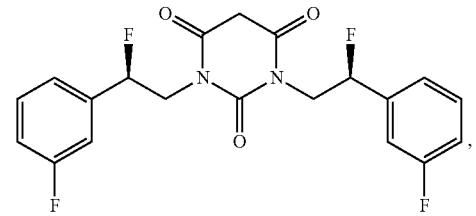
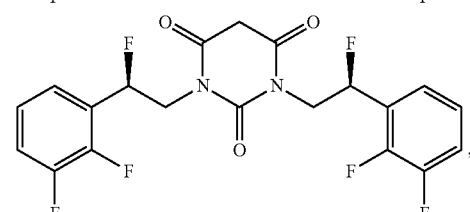
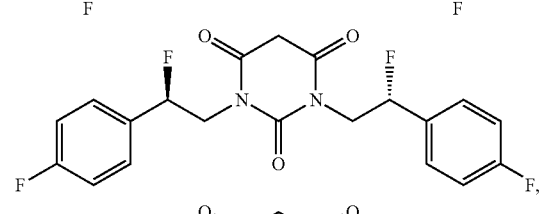
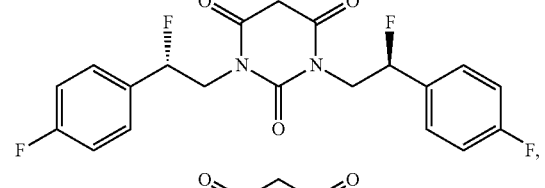
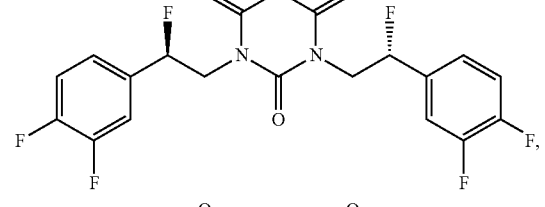
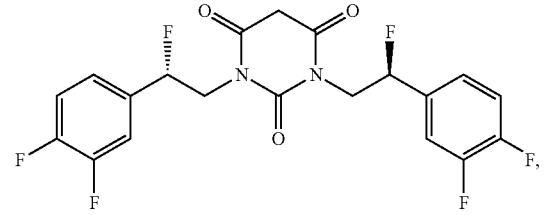
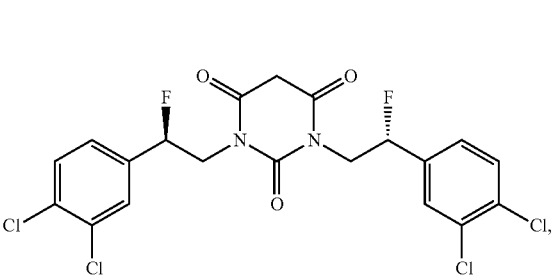
118
-continued
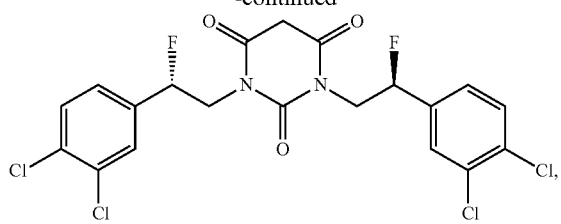
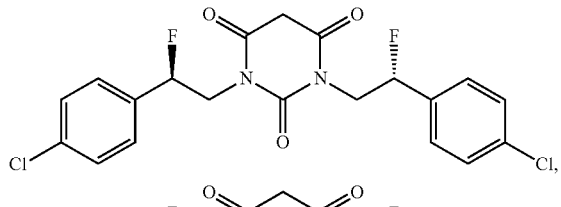
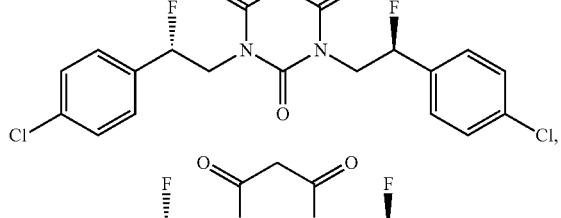
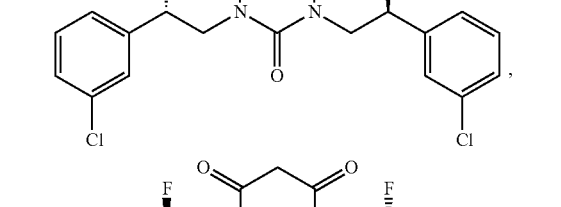
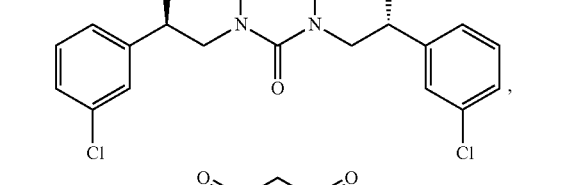
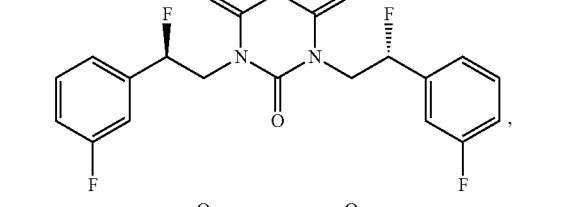
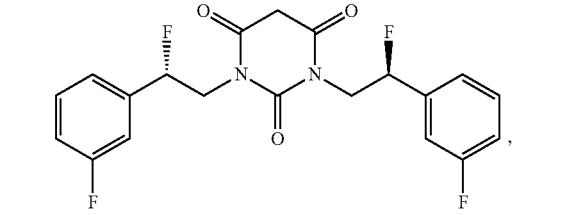
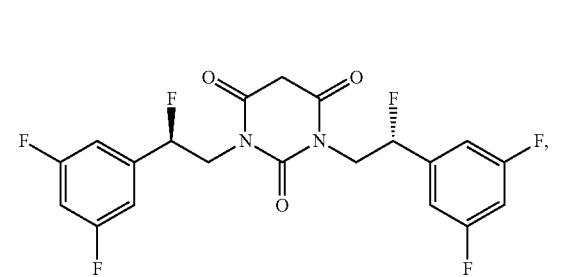

119
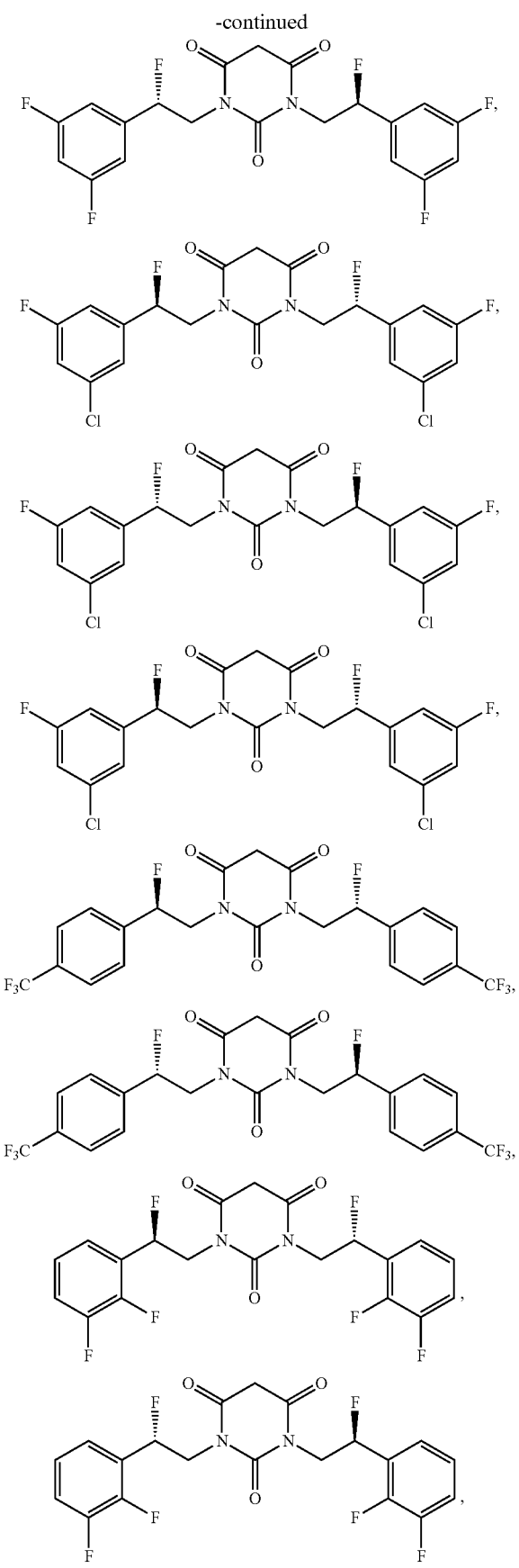
120
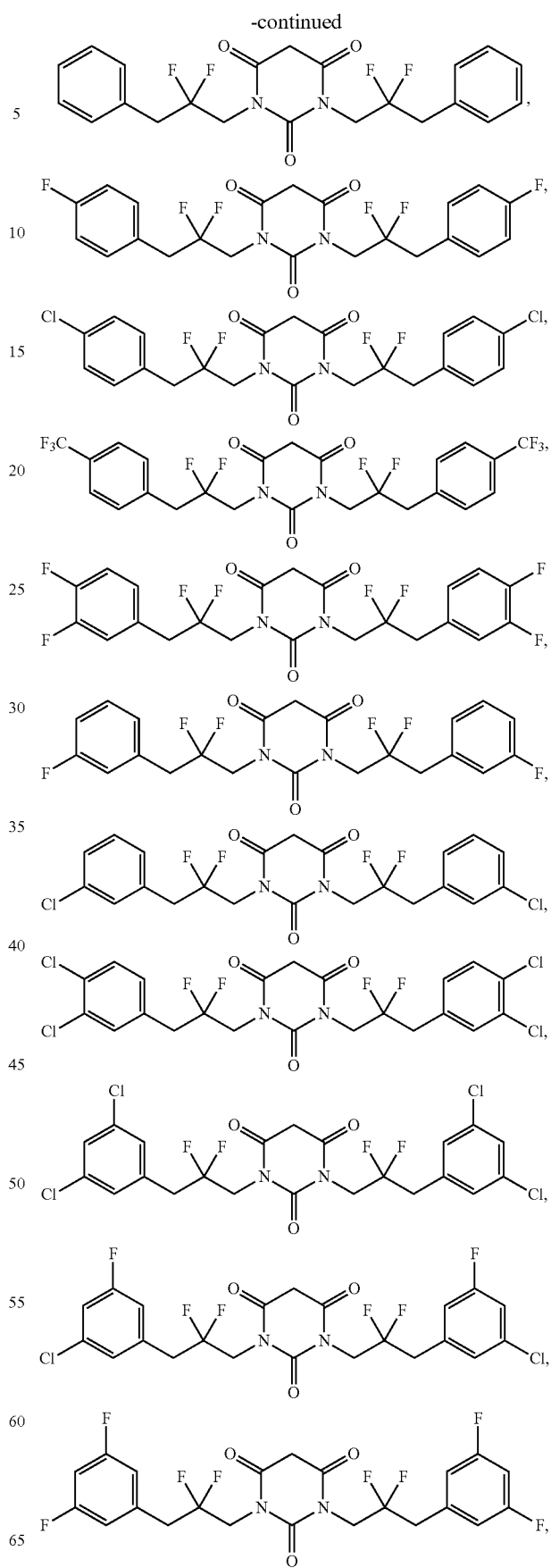

121
-continued
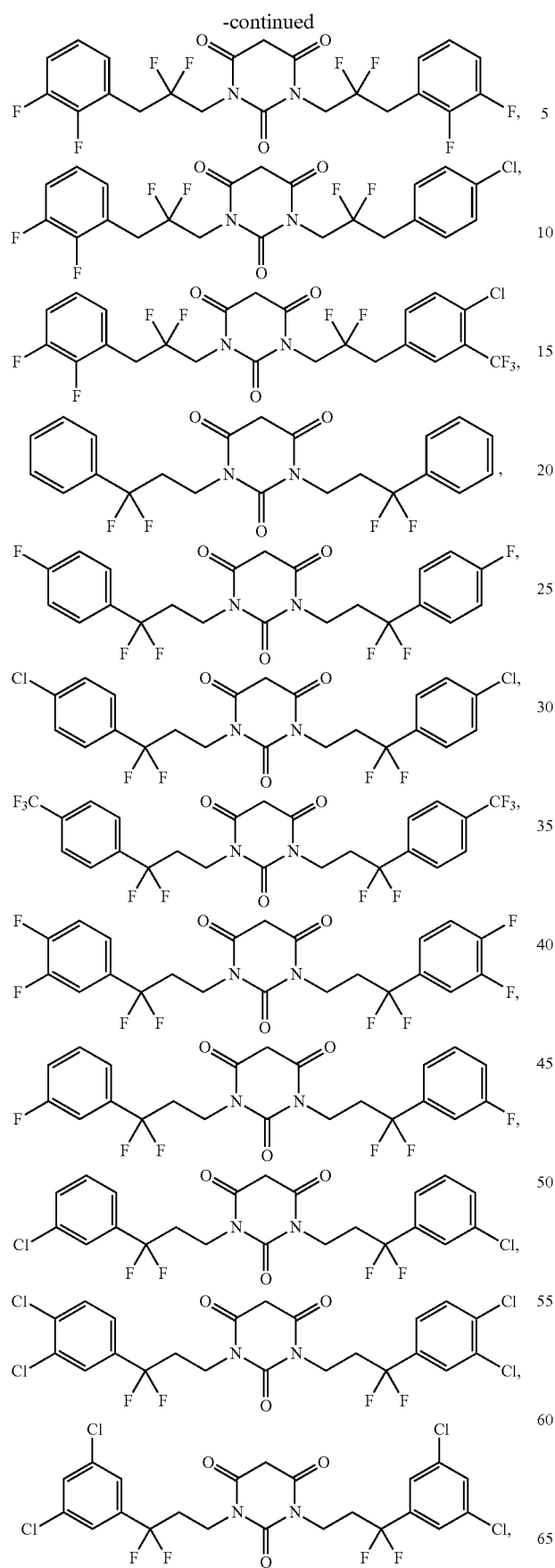
122
-continued
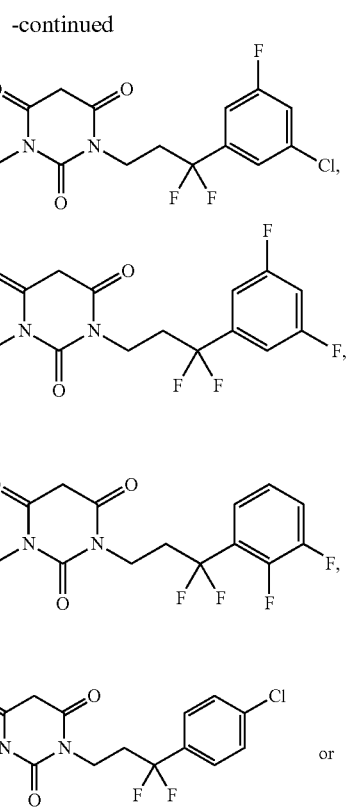
22. The compound according to claim 1, of any one of the following formulae:
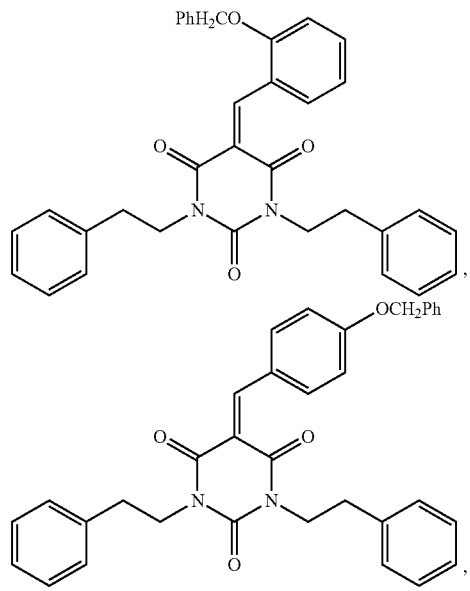

123
-continued
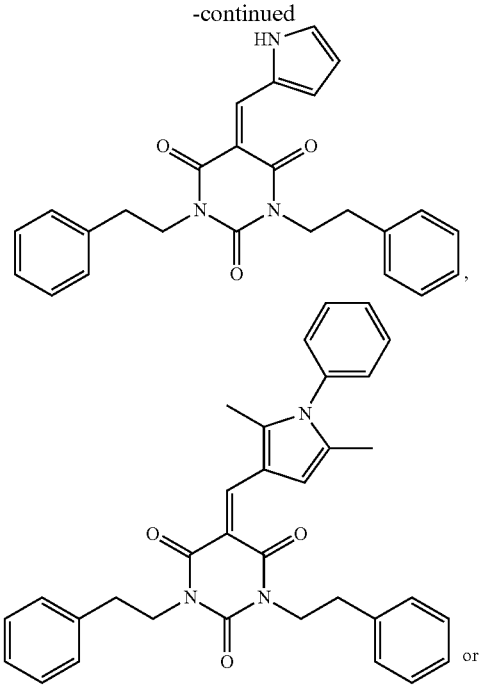
124
-continued
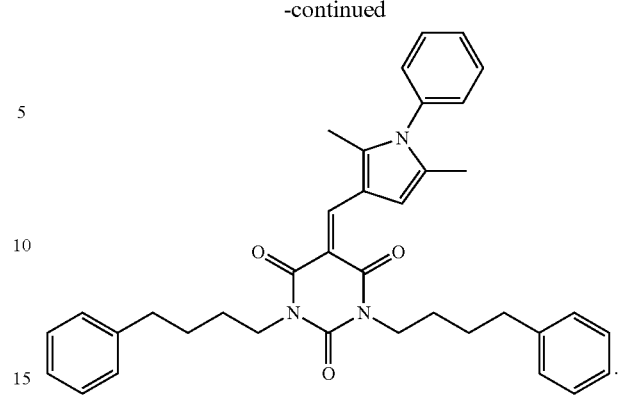
23. A pharmaceutical composition comprising:
   a compound of claim 1, and a pharmaceutically acceptable excipient.
* * * * *